United States Patent
Yoon et al.

(10) Patent No.: US 10,787,641 B2
(45) Date of Patent: Sep. 29, 2020

(54) THERAPEUTIC USE OF CD31 EXPRESSING CELLS

(71) Applicant: Emory University, Atlanta, GA (US)

(72) Inventors: Young-sup Yoon, Atlanta, GA (US); Hyun-Jai Cho, Seoul (KR)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 15/334,541

(22) Filed: Oct. 26, 2016

(65) Prior Publication Data

US 2017/0107489 A1 Apr. 20, 2017

Related U.S. Application Data

(63) Continuation of application No. 14/256,183, filed on Apr. 18, 2014, now abandoned, which is a continuation of application No. 12/447,180, filed as application No. PCT/US2007/022948 on Oct. 29, 2007, now Pat. No. 8,747,905.

(60) Provisional application No. 60/855,998, filed on Oct. 31, 2006, provisional application No. 60/854,957, filed on Oct. 27, 2006.

(51) Int. Cl.
| | |
|---|---|
| *C12N 15/85* | (2006.01) |
| *C12N 5/078* | (2010.01) |
| *C12N 5/0789* | (2010.01) |
| *C12N 5/071* | (2010.01) |
| *C12N 5/00* | (2006.01) |
| *A61K 35/12* | (2015.01) |

(52) U.S. Cl.
CPC ......... *C12N 5/0634* (2013.01); *C12N 5/0081* (2013.01); *C12N 5/0087* (2013.01); *C12N 5/0647* (2013.01); *C12N 5/0692* (2013.01); *A61K 2035/124* (2013.01); *C12N 2500/38* (2013.01); *C12N 2501/105* (2013.01); *C12N 2501/11* (2013.01); *C12N 2501/115* (2013.01); *C12N 2501/165* (2013.01)

(58) Field of Classification Search
None
See application file for complete search history.

(56) References Cited

U.S. PATENT DOCUMENTS

| | | | | |
|---|---|---|---|---|
| 6,306,575 | B1 * | 10/2001 | Thomas | C07K 16/18 424/138.1 |
| 8,747,905 | B2 | 6/2014 | Yoon | |
| 8,796,020 | B2 | 8/2014 | Song | |
| 8,883,499 | B2 * | 11/2014 | Hedrick | A61B 17/00 424/93.7 |
| 2004/0126879 | A1 | 7/2004 | Schneider | |
| 2005/0208025 | A1 * | 9/2005 | Fleming | C12N 5/0647 424/93.7 |
| 2005/0260175 | A1 | 11/2005 | Hedrick | |

FOREIGN PATENT DOCUMENTS

| | | | |
|---|---|---|---|
| WO | 2006031467 | | 3/2006 |
| WO | WO 2006031467 | * | 3/2006 |
| WO | WO2007037561 | * | 4/2007 |

OTHER PUBLICATIONS

Kang et al ( British J of haematol, 2001, v.113, pp. 962-969.*
Loomans et al ( Arteriosclerosis, 2006,v.26, pp. 1760-1767).*
Asahara et al., Isolation of Putative Progenitor Endothelial Cells for Angiogenesis, Science 275, 964 (1997).
Cho et al. Abstract 1074: Bone Marrow-derived CD31+ Cells have Angiogenic-vasculogenic Properties and are Effective for Repairing Ischemic Cardiovascular Disease, Circulation. 2006;114:II_198.
Cochlovius et al. Thereapeutic Antibodies, Mod. Drug Discovery, 2003, 33-38-22.
Davies et al. Transplantation of Specific Human Astrocytes Promotes Functional Recovery after Spinal Cord Injury, PLoS ONE 6(3): e17328.
Feldman et al. Anti-TNF[alpha] Therapy Is Useful in Rheumatoid Arthritis and Crohn's Disease: Analysis of the Mechanism of Action Predicts Utility in Other Diseases, Transplantation Proceedings, 30, 4126-4127 (1998).
Jeong et al. Dual Angiogenic and Neurotrophic Effects of Bone Marrow-Derived Endothelial Progenitor Cells on Diabetic Neuropathy, Circulation 2009, 119:699-708.
Kim et al. CD31+ Cells Represent Highly Angiogenic and Vasculogenic Cells in Bone Marrow: Novel Role of Nonendothelial CD31+ Cells in Neovascularization and Their Therapeutic Effects on Ischemic Vascular Disease, Circ Res. 2010;107:602-614.
Kim et al. Human Peripheral Blood-Derived CD31+ Cells Have Robust Angiogenic and Vasculogenic Properties and Are Effective for Treating Ischemic Vascular Disease J Am Coll Cardiol. 2010, 56(7):593-607.
Mestas et al. Of Mice and Not Men: Differences between Mouse and Human Immunology, J Immunol, 2004; 172:2731-2738.
Mi et al. Induction of Astrocyte Differentiation by Endothelial Cells, The Journal of Neuroscience, 2001, 21(5):1538-1547.
Newman, The role of PECAM-1 in vascular cell biology, Ann N Y Acad Sci. 1994, 714:165-74.
Oh et al. Cardiac progenitor cells from adult myocardium: Homing, differentiation, and fusion after infarction, PNAS, 2003,vol. 100, No. 21, 2313-12318.
Yoon email to Donna Tu <donna.tu@heart.org> APS.24.2. Stem Cells and Myocardial Regeneration Tuesday, Nov. 14, 2006, 9:00 am-5:00 pm McCormick Place, Hall A2.
Yoon Rule 132 Declaration in U.S. Appl. No. 12/447,180 dated Sep. 16, 2013.
Yu et al. Vascular Endothelial Growth Factor Mediates Corneal Nerve Repair, Invest Ophthalmol Vis Sci. 2008, 49(9):3870-8.
Guo et al. CD34—Hematopoietic Stem Cells: Current Concepts and Controversies, Stem Cells, 2003, 21:15-20.
Kawamoto et al. Intramyocardial Transplantation of Autologous Endothelial Progenitor Cells for Therapeutic Neovascularization of Myocardial Ischemia, Circulation. 2003, 107:461-468.

(Continued)

*Primary Examiner* — Michail A Belyavskyi
(74) *Attorney, Agent, or Firm* — Emory Patent Group

(57) ABSTRACT

The present invention features compositions and methods related to the isolation, culture and therapeutic use of CD31-expressing cells.

2 Claims, 47 Drawing Sheets

(56) References Cited

OTHER PUBLICATIONS

Kim et al. Advances in bone marrow-derived cell therapy: CD31—expressing cells as next generation cardiovascular cell therapy, Regen Med. 2011, 6(3): 335-349.

Kim et al. Cardiovascular repair with bone marrow-derived cells, Blood Res 2013;48:76-86.

Kim et al. Cultured Human Bone Marrow-Derived CD31+ Cells Are Effective for Cardiac and Vascular Repair Through Enhanced Angiogenic, Adhesion, and Anti-Inflammatory Effects, J Am Coll Cardiol. 2014, 64(16): 1681-1694.

Lee et al. Revisiting cardiovascular regeneration with bone marrow-derived angiogenic and vasculogenic cells, British Journal of Pharmacology (2013) 169 290-303.

Lee et al. Enhanced Therapeutic Neovascularization by CD31-Expressing Cells and Embryonic Stem Cell-Derived Endothelial Cells Engineered with Chitosan Hydrogel Containing VEGF-Releasing Microtubes, Biomaterials. 2015, 63: 158-167.

Stockinger et al. Phenotype of human T cells expressing CD31, a molecule of the immunoglobulin supergene family. Immunology, 1992, 75(1):53-8.

Yoder et al. Human Endothelial Progenitor Cells, Cold Spring Harb Perspect Med, 2012, 2:a006692.

\* cited by examiner

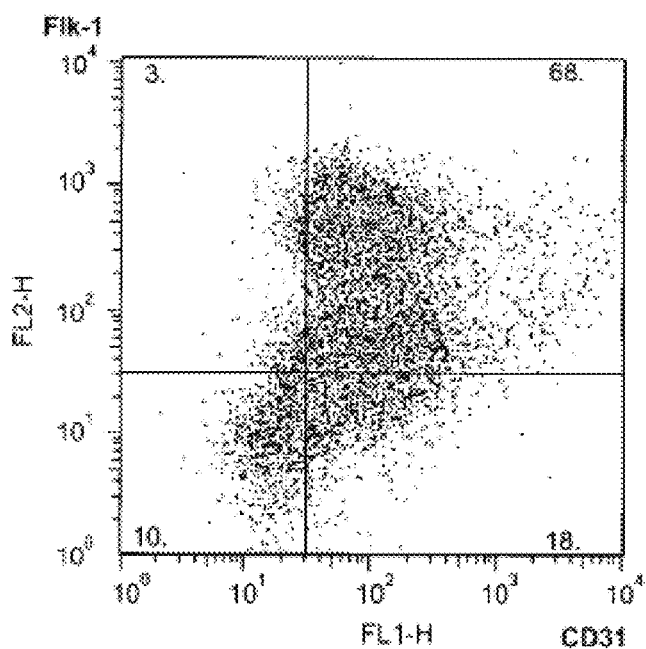
FIG. 1L
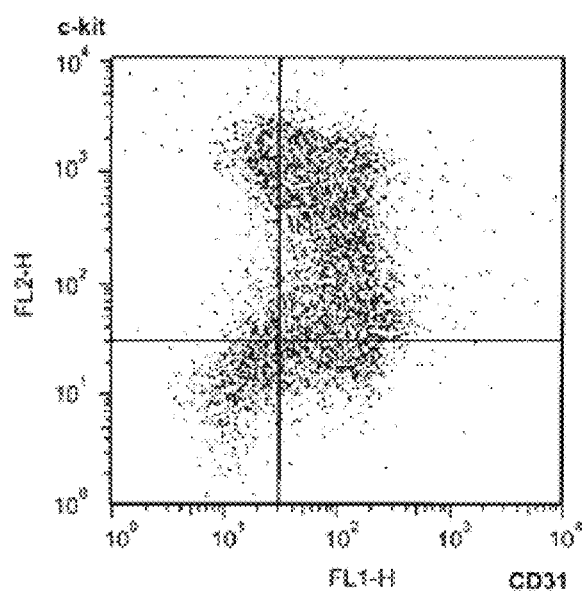 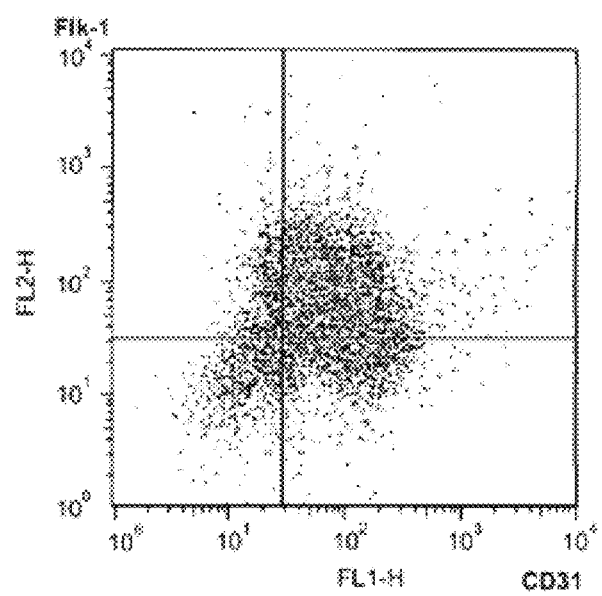
FIG. 1M				FIG. 1N

FIG. 3AFIG. 3B

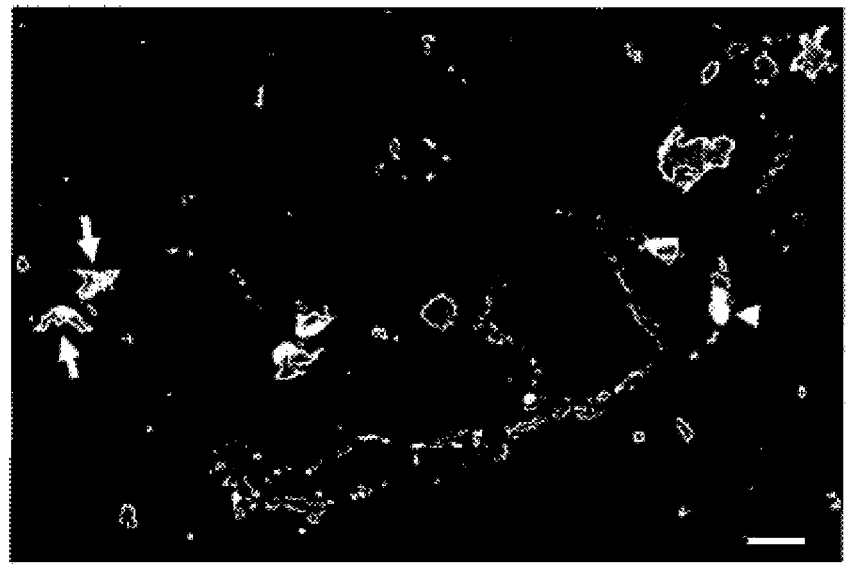
FIG. 11A
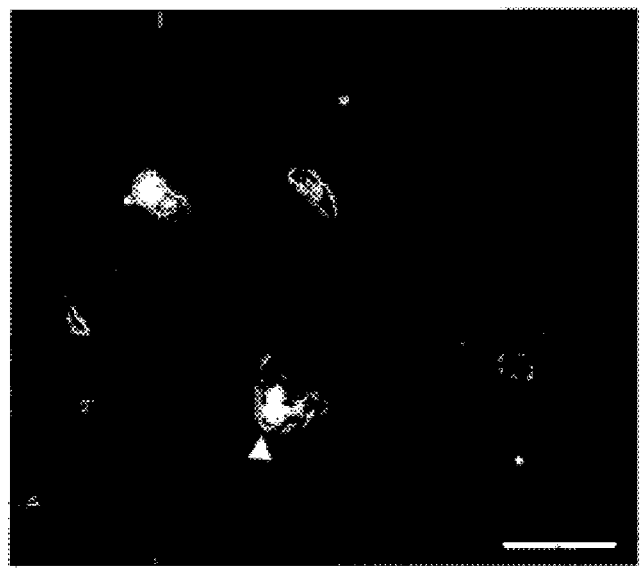 
FIG. 11B  FIG. 11C

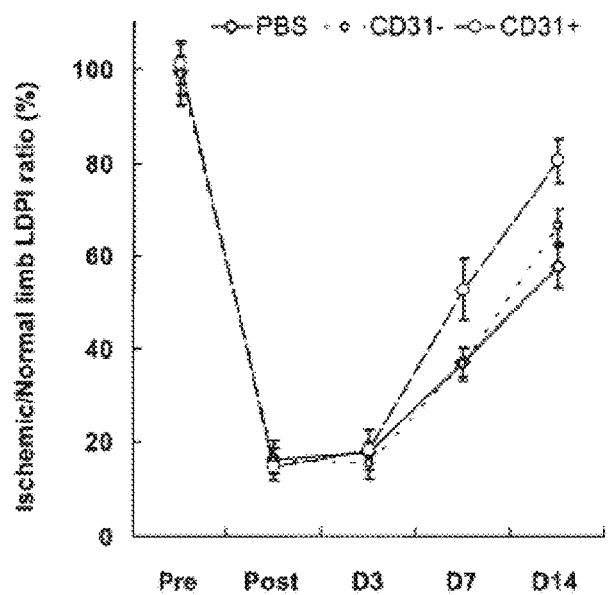
FIG. 14D
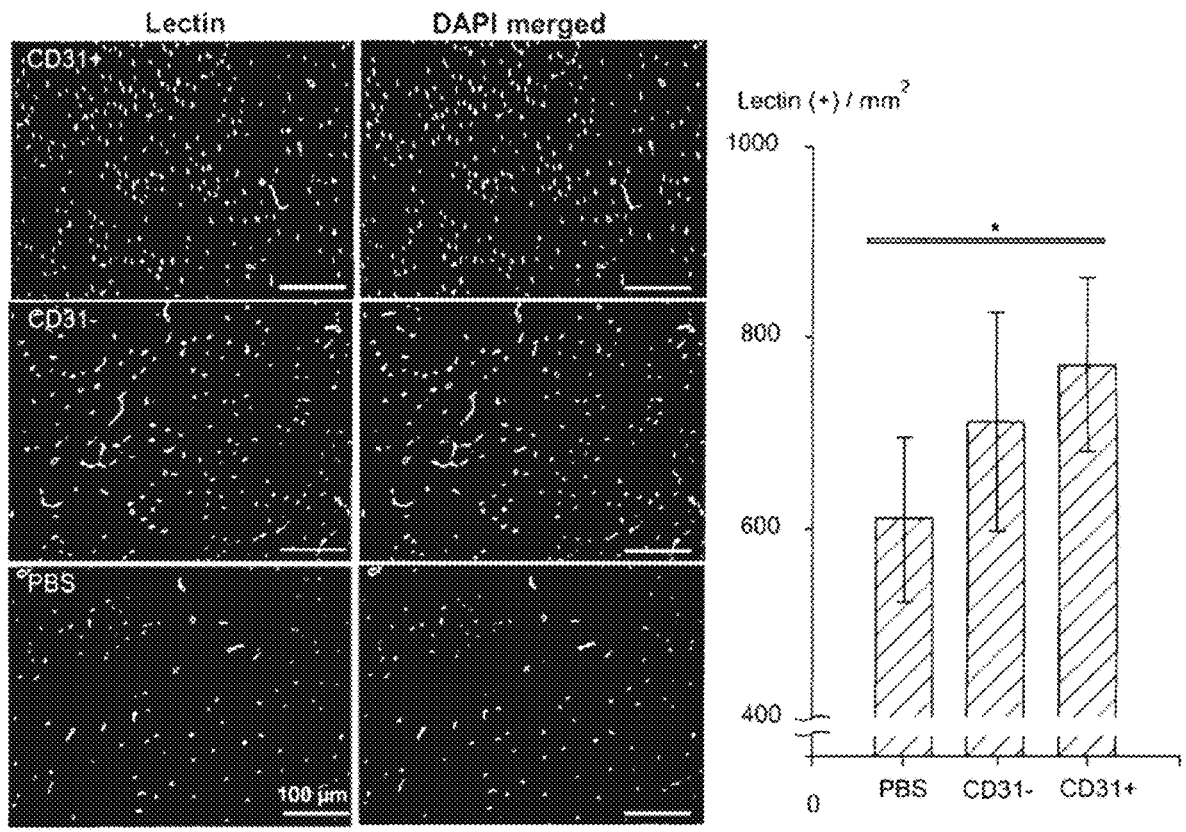
FIG. 15A
FIG. 15B

Day 1

Day 5 vWF, D8

ILB4, ac-DiI-LDL, D8

VE-CAD, D9

VEGFR-2, D9

CD31, D9

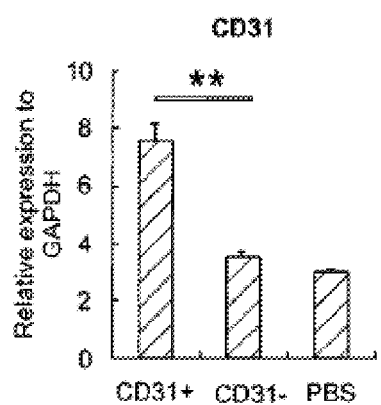
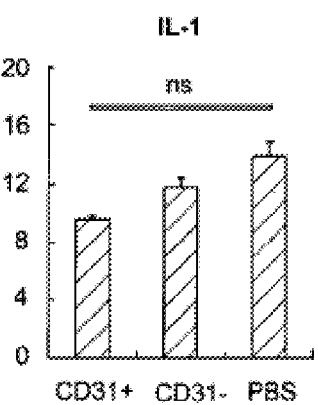
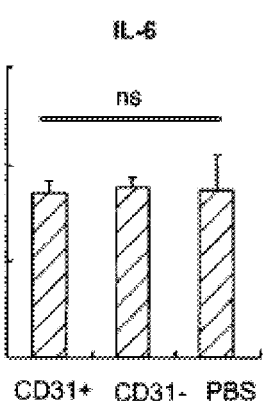
FIG. 24G  FIG. 24H  FIG. 24I
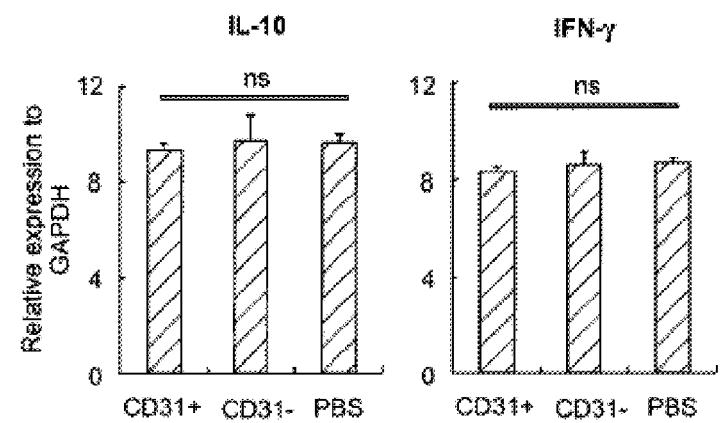
FIG. 24J  FIG. 24K

THERAPEUTIC USE OF CD31 EXPRESSING CELLS

CROSS-REFERENCE TO RELATED APPLICATIONS

This application is a continuation of U.S. application Ser. No. 14/256,183 filed Apr. 18, 2014, now abandoned, which is a continuation of U.S. application Ser. No. 12/447,180 filed Nov. 30, 2009 that granted as U.S. Pat. No. 8,747,905 on Jun. 10, 2014, which is the National Stage of International Application No. PCT/US2007/022948 filed Oct. 29, 2007, which claims the benefit of priority to U.S. Provisional Application No. 60/854,957 filed Oct. 27, 2006 and U.S. Provisional Application No. 60/855,998 filed Oct. 31, 2006. The entirety of each of these applications is hereby incorporated by reference for all purposes.

STATEMENT REGARDING FEDERALLY FUNDED RESEARCH

This invention was made with government support under Grant No. 1RO1 HL 079137 from the National Institutes of Health. The Government has certain rights in the invention.

BACKGROUND OF THE INVENTION

Despite many breakthroughs in cardiovascular medicine, the treatment of ischemic cardiovascular diseases remains among the most prominent health challenges worldwide. The identification of adult stem or progenitor cells capable of contributing to tissue regeneration has raised the possibility that cell therapy could be employed for repair of ischemic damaged tissues. Current investigations have suggested bone marrow (BM) cells as a potential source for adult stem or progenitor cells. BM-derived stem cells appear to have the capacity to repopulate many nonhematopoietic tissues, such as vessel and muscle. The promising results from initial experimental studies on BM-derived stem cells have already promoted the initiation of clinical trials for the treatment of acute myocardial infarction, ischemic cardiomyopathy, and limb ischemia. Yet knowledge relating to adult stem cells populations is incomplete. One of the most important and unresolved issues in cell therapy is the selection of ideal cells for regeneration. Even though various kinds of stem or progenitor cells have been proposed and shown to be effective for cardiovascular regeneration, each cell type has its own pitfalls. For example, unfractionated whole BM cells may encounter unexpected and potentially serious adverse effects, such as intramyocardial calcification. $CD34^+$ cells or $c-kit^+$ cells exist in low numbers in BM (less than 1%), therefore, the mobilization process is required to obtain sufficient numbers of cells to be used for cell therapy. Endothelial progenitor cells or mesenchymal stem cells are culture expandable cells, that require large amounts of serum for culture and need from days to months to be prepared for clinical use. Better methods for selecting, isolating, and culturing stem cells for use in regenerative medicine are urgently required.

SUMMARY OF THE INVENTION

As described below, the present invention features compositions and methods related to the isolation, culture and therapeutic use of CD31-expressing cells.

In one aspect, the invention generally features a method of repairing or regenerating a tissue in a subject in need thereof. The method involves contacting the tissue with a $CD31^+$ cell, thereby repairing or regenerating the tissue.

In another aspect, the invention provides a method for increasing angiogenesis in a subject in need thereof. The method involves contacting the tissue with a $CD31^+$ cell, thereby repairing or regenerating the tissue.

In another aspect, the invention features a method for ameliorating ischemia-related tissue damage in a subject in need thereof, the method involves administering to the subject a $CD31^+$ cell having the potential to differentiate into an endothelial cell; increasing angiogenesis and increasing secretion of a paracrine factor or cytokine in a tissue of the subject, thereby ameliorating ischemia in the subject. In various embodiments, the ischemia-related tissue damage is associated with heart failure, myocardial infarction, limb ischemia, stroke, transient ischemia, or reperfusion injury.

In yet another aspect, the invention features a method for ameliorating a neuropathy in a subject in need thereof. The method involves administering to the subject a $CD31^+$ cell having the potential to differentiate into an endothelial cell; and increasing angiogenesis in a neural tissue of the subject, thereby ameliorating a neuropathy in the subject.

In yet another aspect, the invention features a method for ameliorating heart failure in a subject in need thereof. The method involves administering to a cardiac tissue a $CD31^+$ cell; and increasing angiogenesis in the cardiac tissue, thereby ameliorating heart failure in the subject.

In yet another aspect, the invention features a method for ameliorating liver or renal failure in a subject in need thereof. The method involves administering to a liver or renal tissue a $CD31^+$ cell; and engrafting the $CD31^+$ cell into the liver or renal tissue, thereby ameliorating liver or renal failure in the subject. In various embodiments of the above aspects, the cell is locally or systemically administered. In other embodiments of the above aspects, the cell is integrated into the tissue.

In yet another aspect, the invention features a method for identifying a multipotent stem cell. The method involves identifying a cell that expresses $CD31^+$, and isolating the cell. In one embodiment, the identification step involves an immunoassay.

In yet another aspect, the invention features a packaged pharmaceutical containing a therapeutically effective amount of a $CD31^+$ cell, and instructions for use in treating a subject having a condition characterized by excess cell death. In one embodiment, the composition further contains a therapeutic polypeptide.

In yet another aspect, the invention features a packaged pharmaceutical containing a therapeutically effective amount of a $CD31^+$ cell having the potential to differentiate into an endothelial cell, and instructions for use in treating or preventing an ischemic disease in a subject. In one embodiment, the cell is genetically modified.

In yet another aspect, the invention features a method for identifying an agent useful for enhancing the transdifferentiation of a $CD31^+$ cell, the method involving contacting a $CD31^+$ cell with an agent; and measuring an increase in the expression of a protein not expressed in an untreated $CD31^+$ control cell, where an increase in protein expression in the treated cell, as compared to the untreated cell identifies the agent as useful for transdifferentiating the $CD31^+$ cell. In one embodiment, the protein is insulin. In another embodiment, the protein is an endothelial cell marker, a liver cell marker, or a renal cell marker.

In yet another aspect, the invention features a method for culturing a CD31-expressing multipotent stem cell.

In another aspect, the invention provides a method for ameliorating ischemia related tissue damage in a subject in need thereof, the method involving administering to the subject a CD31+ cell; and increasing secretion of a paracrine factor or cytokine in a tissue of the subject, thereby ameliorating ischemia related tissue damage in the subject.

In yet another aspect, the invention provides a method for ameliorating heart failure in a subject in need thereof, the method involving administering to a cardiac tissue a CD31+ cell; and increasing secretion of a paracrine factor or cytokine in the cardiac tissue, thereby ameliorating heart failure in the subject.

In yet another aspect, the invention provides a method for increasing wound healing in a tissue of subject in need thereof, the method comprising: administering to said tissue a CD31+ cell thereby increasing wound healing.

In still another aspect, the invention provides a method for increasing wound healing in a tissue of a subject in need thereof, the method involving administering to said tissue a CD31+ cell; and increasing angiogenesis thereby increasing wound healing.

In still another aspect, the invention provides a method for increasing wound healing in a tissue of a subject in need thereof, the method involving administering to said tissue a CD31+ cell; and increasing secretion of a paracrine factor or cytokine in said tissue, thereby increasing wound healing in the subject.

In still another aspect, the invention provides a method for increasing wound healing in a tissue of a subject in need thereof, the method involving administering to said tissue a CD31+ cell; and engrafting the CD31+ cell into the tissue, thereby increasing wound healing.

In yet another aspect, the invention provides a method for treating a hematologic disease in a subject in need thereof, the method involving administering to said tissue a CD31+ Lin-cell thereby treating said hematologic disease (e.g., leukemia, lymphoma, myelodysplastic syndrome, pancytopenia, anemia, thrombocytopenia, leucopenia).

In yet another aspect, the invention provides a method for identifying a multipotent stem cell, the method comprising: identifying a cell that expresses CD31+.

In another aspect, the invention provides a method for identifying a multipotent stem cell, the method involving identifying a cell that expresses CD31+ and does not express Lin.

In yet another aspect, the invention provides a method of isolating a multipotent stem cell the method involving isolating a CD31+ cell; and selecting said CD31+ cell.

In another aspect, the invention provides a method of isolating a multipotent stem cell the method involving isolating a CD31+lin− cell; and selecting said CD31+lin− cell.

In yet another aspect, the invention provides a method for culturing a CD31+ cell involving isolating stem cells from bone marrow, peripheral blood or umbilical cord blood; identifying a CD31+ cell; and expanding said CD31+ cell.

In another aspect, the invention provides a method for culturing a CD31+lin− cell involving isolating stem cells from bone marrow, peripheral blood or umbilical cord blood; identifying a CD31+lin− cell; and expanding said CD31+lin− cell.

In another aspect, the invention provides a method of repairing or regenerating a tissue in a subject in need thereof, the method involving isolating a CD31+ cell from bone marrow, peripheral blood or cord blood; expanding said CD31+ cell in vitro to obtain a cell population enriched in bone marrow-derived stem or progenitor cells; and administering said CD31+ cell to said subject thereby repairing or regenerating said tissue.

In still another aspect, the invention provides a method for increasing angiogenesis in a subject in need thereof, the method involving isolating a CD31+ cell from bone marrow, peripheral blood or cord blood; expanding said CD31+ cell in vitro to obtain a cell population enriched in bone marrow-derived stem or progenitor cells; and administering said CD31+ cell to said subject thereby increasing angiogenesis.

In still another aspect, the invention provides a method of ameliorating ischemia related tissue damage in a subject in need thereof, the method involving isolating a CD31+ cell from bone marrow, peripheral blood or cord blood; expanding said CD31+ cell in vitro to obtain a cell population enriched in bone marrow-derived stem or progenitor cells; administering said CD31+ cell to said subject; and increasing angiogenesis in a tissue of said subject, thereby ameliorating ischemia in said subject.

In still another aspect, the invention provides a method of ameliorating ischemia related tissue damage in a subject in need thereof, the method involving isolating a CD31+ cell from bone marrow, peripheral blood or cord blood; expanding said CD31+ cell in vitro to obtain a cell population enriched in bone marrow-derived stem or progenitor cells; administering said CD31$^{30}$ cell to said subject; and increasing secretion of a paracrine factor or cytokine in a tissue of said subject, thereby ameliorating ischemia in said subject.

In still another aspect, the invention provides a method of ameliorating a neuropathy in a subject in need thereof, the method involving isolating a CD31+ cell from bone marrow, peripheral blood or cord blood; expanding said CD31+ cell in vitro to obtain a cell population enriched in bone marrow-derived stem or progenitor cells; administering said CD31+ cell to said subject; and increasing angiogenesis in a neural tissue of said subject, thereby ameliorating a neuropathy in said subject.

In still another aspect, the invention provides a method of ameliorating a neuropathy in a subject in need thereof, the method involving isolating a CD31+ cell from bone marrow, peripheral blood or cord blood; expanding said CD31+ cell in vitro to obtain a cell population enriched in bone marrow-derived stem or progenitor cells; administering said CD31+ cell to said subject; and increasing secretion of a paracrine factor or a cytokine in a neural tissue of said subject, thereby ameliorating a neuropathy in said subject.

In still another aspect, the invention provides a method of ameliorating heart failure in a subject in need thereof, the method involving isolating a CD31+ cell from bone marrow, peripheral blood or cord blood; expanding said CD31+ cell in vitro to obtain a cell population enriched in bone marrow-derived stem or progenitor cells; administering said CD31+ cell to cardiac tissue of said subject; and increasing angiogenesis in said cardiac tissue, thereby ameliorating heart failure in the subject.

In another aspect, the invention provides a method of ameliorating heart failure in a subject in need thereof, the method involving isolating a CD31+ cell from bone marrow, peripheral blood or cord blood; expanding said CD31+ cell in vitro to obtain a cell population enriched in bone marrow-derived stem or progenitor cells; administering said CD31+ cell to cardiac tissue of said subject; and increasing secretion of a paracrine factor or cytokine in said cardiac tissue, thereby ameliorating heart failure in the subject.

In another aspect, the invention provides a method of ameliorating heart failure in a subject in need thereof, the method involving isolating a CD31+ cell from bone marrow, peripheral blood or cord blood; expanding said CD31+ cell in vitro to obtain a cell population enriched in bone marrow-derived stem or progenitor cells; administering said CD31+ cell to cardiac tissue of said subject; and increasing myogenesis in said cardiac tissue, thereby ameliorating heart failure in the subject.

In another aspect, the invention provides a method of ameliorating liver or renal failure in a subject in need thereof, the method involving isolating a CD31+ cell from bone marrow, peripheral blood or cord blood; expanding said CD31+ cell in vitro to obtain a cell population enriched in bone marrow-derived stem or progenitor cells; administering said CD31+ cell to the liver or renal tissue of said subject; and engrafting the CD31+ cell into the liver or renal tissue, thereby ameliorating liver or renal failure in the subject.

In another aspect, the invention provides a method for increasing wound healing in a tissue of subject in need thereof, the method involving isolating a CD31+ cell from bone marrow, peripheral blood or cord blood; expanding said CD31+ cell in vitro to obtain a cell population enriched in bone marrow-derived stem or progenitor cells; and administering to said tissue a CD31+ cell thereby increasing wound healing.

In another aspect, the invention provides a method for increasing wound healing in a tissue of subject in need thereof, the method involving isolating a CD31+ cell from bone marrow, peripheral blood or cord blood; expanding said CD31+ cell in vitro to obtain a cell population enriched in bone marrow-derived stem or progenitor cells; administering to said tissue a CD31+ cell thereby increasing angiogenesis thereby increasing wound healing.

In another aspect, the invention provides a method for increasing wound healing in a tissue of subject in need thereof, the method involving isolating a CD31+ cell from bone marrow, peripheral blood or cord blood; expanding said CD31+ cell in vitro to obtain a cell population enriched in bone marrow-derived stem or progenitor cells; and administering to said tissue a CD31+ cell thereby increasing secretion of a paracrine factor or cytokine in said tissue, thereby increasing wound healing in the subject.

In yet another aspect, the invention provides a method for increasing wound healing in a tissue of a subject in need thereof, the method involving isolating a CD31+ cell from bone marrow, peripheral blood or cord blood; expanding said CD31+ cell in vitro to obtain a cell population enriched in bone marrow-derived stem or progenitor cells; and administering to said tissue a CD31+ cell; and engrafting the CD31+ cell into the tissue, thereby increasing wound healing.

In yet another aspect, the invention provides a method for treating a hematologic disease in a tissue of a subject in need thereof, the method involving isolating a CD31+ lin− cell from bone marrow, peripheral blood or cord blood; expanding said CD31+lin− cell in vitro to obtain a cell population enriched in bone marrow-derived stem or progenitor cells; and administering to said tissue a CD31+lin− cell; and thereby treating said hematologic disease.

In yet another aspect, the invention provides an isolated CD31+, lin− cell or a pharmaceutical composition comprising and isolated CD31+Lin− cell, for example, an isolated CD31+Lin− cell obtained by the method of a previous aspect.

In various embodiments of the above aspects, the tissue is a muscle tissue, cardiac tissue, neural tissue, liver tissue, pancreatic tissue, bone tissue, cartilage, renal tissue, or a tissue characterized by excess cell death. In other embodiments of any of the above aspects, the subject has or has a propensity to develop myocardial infarction, congestive heart failure, peripheral vascular obstructive disease, ischemia, limb ischemia, stroke, transient ischemia, reperfusion injury, peripheral neuropathy, toxic neuropathy, diabetic dementia, or autonomic neuropathy, liver failure, renal failure, diabetes, rheumatoid arthritis, osteoarthritis, and osteoporosis. In other embodiments of the above aspects, the cell is integrated into the vasculature of the tissue. In still other embodiments of the above aspects, the CD31+ cell is isolated and expanded in vitro to obtain a cell population enriched in bone marrow-derived stem or progenitor cells prior to being administered to the host subject. In still other embodiments of the above aspects, the cell is genetically modified. In still other embodiments of the above aspects, the cell is an endothelial progenitor cell (EPC). In other embodiments of the above aspects, the cell is isolated from the bone marrow of a donor subject. If desired, the donor and the subject receiving the cell are the same individual. In other embodiments of the above aspects, the cell is a human multipotent stem cell that expresses a normal, increased, or reduced levels of a marker selected from any one or more of: CD90, CD117, CD34, CD113, FLK-1, tie-2, Oct 4, GATA-4, NKx2.5, Rex-1, CD 105, CD 117, CD 133, MHC class I receptor and MHC class II receptor, as compared to a CD31− cell. In still other embodiments, the cell expresses or expresses altered levels of at least two, three, four, or all markers. In still other embodiments, the method of the invention further involves administering to the subject a therapeutic polypeptide or a nucleic acid encoding a therapeutic polypeptide. In still other embodiments, the cell is locally or systemically administered. In various embodiments of any of the above aspects, the subject has or has a propensity to develop any one or more of myocardial infarction, congestive heart failure, peripheral vascular obstructive disease, ischemia, limb ischemia, stroke, transient ischemia, reperfusion injury, peripheral neuropathy, diabetic neuropathy, toxic neuropathy, diabetic dementia, or autonomic neuropathy, spinal cord injury, leukemia, lymphoma, myelodysplastic syndrome, pancytopenia, anemia, thrombocytopenia, leukopenia, liver failure, renal failure, diabetes, rheumatoid arthritis, osteoarthritis, skin wound, diabetic foot or ulcer, gangrene, diabetic wound and osteoporosis. In various embodiments of the above aspects, the CD31+ cell is lineage depleted; is isolated from bone marrow, peripheral blood or umbilical cord blood of a donor subject (e.g., a mammal, such as a human). In various embodiments of the above aspects, the cell expresses at least one of Sca-1 or c-kit; does not express Lin. In various embodiments of the above aspects, the identification step involves an immunoassay. In various embodiments of the above aspects, the protein is a cardiomyogenic marker or neural marker.

Other features and advantages of the invention will be apparent from the detailed description, and from the claims.

Definitions

By "platelet/endothelial cell adhesion molecule (CD31) polypeptide" is meant a protein or fragment thereof having at least 85% identity to the amino acid sequence provided at NP_000433 that acts as a marker for cells having hemangioblastic activity.

By "CD31 nucleic acid sequence" is meant a polynucleotide encoding a CD31 protein.

By "CD31+ cell" is meant a cell that expresses a detectable level of CD31 polypeptide, polynucleotide, or fragment thereof. A CD31+ cell of the invention has hemangioblastic activity. A CD31+ cell according to the invention includes cells that have the potential to give rise to angioblasts or hematopoietic cells. A CD31+ cell according to the invention also includes cells that have the potential to differentiate into endothelial cells. In one embodiment, a CD31+ cell expresses a normal level or an altered (increased or decreased) level as compared to a CD31− cell of at least one of the following markers: CD90, CD117, CD34, CD113, FLK-1, tie-2, Oct 4, GATA-4, NKx2.5, Rex-1, CD105, CD 117, CD133, MHC class I receptor and MHC class II receptor. In another embodiment, a CD31+ cell expresses at least one of Sca-1 or c-Kit. In another embodiment, a CD31+ cell is Lin−. The invention encompasses CD31+ cells derived from sources including but not limited to peripheral blood, including umbilical cord blood, for example human umbilical cord blood, bone marrow and hematopoietic stem cells. The invention also encompasses CD31+ cells from mammals and, in particular, humans.

By "stem cell" is meant an undifferentiated cell which is capable of essentially unlimited propagation either in vivo or ex vivo and capable of differentiation to other cell types. This can be to certain differentiated, committed, immature, progenitor, or mature cell types present in the tissue from which it was isolated, or dramatically differentiated cell types, such as for example the erythrocytes and lymphocytes that derive from a common precursor cell, or even to cell types at any stage in a tissue completely different from the tissue from which the stem cell is obtained. For example, blood stem cells may become brain cells or liver cells, neural stem cells can become blood cells, such that stem cells are pluripotential, and given the appropriate signals from their environment, they can differentiate into any tissue in the body.

By "hemangioblastic activity" is meant having the potential to give rise to angioblasts, endothelial cells and hematopoietic cells. By "having the potential to give rise to angioblasts and hematopoietic cells" is meant having the ability to produce one or more cells having an angioblastic and/or hematopoietic phenotype under the appropriate in vitro or in vivo culture or implantation conditions.

By "angioblast" is meant a cell derived from a hemangioblast from which blood vessel growth originates during angiogenesis or vasculogenesis. An angioblast can be an endothelial cell precursor. In one embodiment, an "angioblast" expresses at least one of Flk-1 or CD34.

By "hematopoietic cell" is meant a stem cell which gives rise to all the blood cell types including myeloid (monocytes and macrophages, neutrophils, basophils, eosinophils, erythrocytes, megakaryocytes/platelets, dendritic cells) and lymphoid lineages (T-cells, B-cells, NK-cells). The hematopoietic tissue contains cells with long term and short term regeneration capacities and committed multipotent, oligopotent and unipotent progenitors.

By "transdifferentiation" is meant an alteration in a cell such that the transdifferentiated cell expresses a detectable level of at least one protein of interest not typically expressed in the cell.

By "a cell having the potential to differentiate into an endothelial cell" is meant any cell that can when cultured or implanted under suitable conditions give rise to cells having an endothelial cell phenotype, expressing one or more endothelial cell markers, or having an endothelial cell function. The term "a cell having the potential to differentiate into an endothelial cell" includes but is not limited to multipotent stem cells, endothelial progenitor cells, mesenchymal stem cells, mononuclear cells, or progenitors or progeny thereof. In one embodiment, a "cell having the potential to differentiate into an endothelial cell" expresses at least one of a cytokine including but not limited to VEGF, IGF-1 and bFGF.

A "cell having the potential to differentiate into an endothelial cell" differentiates into an endothelial cell that expresses one or more endothelial cell markers including but not limited to KDR, endothelial nitric oxidase synthase, VE-Cadherin, CD34, FLK-1, Tie2, CD31, VonWillebrand Factor, CD136 or Factor 8.

An "endothelial cell" according to the invention may perform an endothelial cell function including but not limited to uptake of DiI-acetylated low-density lipoprotein (DiI-acLDL) and binding of lectin.

By "repair" as it refers to a tissue or organ is meant ameliorate damage or disease in a tissue or organ.

By "regenerate" is meant capable of contributing at least one cell to the repair of de novo construction of a tissue or organ.

By "ameliorate" is meant decrease, suppress, attenuate, diminish, arrest, or stabilize the development or progression of a disease.

By "decrease" is meant any negative change. Exemplary decreases include 5%, 10%, 20%, 25%, 30%, 40%, or 50%, 60%, 70%, 80%, 90%, or even by as much as 100% compared to a control. Exemplary decreases also include at least 1-fold (for example, 1, 2, 3, 4, 5, 6, 7, 8, 9, 10, 20, 30, 40, 50, 60, 70, 80, 90, 100, 1000, 10,000-fold or more).

By "angiogenesis" is meant the growth of new blood vessels. Such growth may originate from an existing blood vessel or by the development of new blood vessels originating from stem cells, angioblasts, or other precursor cells. These stem cells can be recruited from bone marrow endogenously or implanted therapeutically. Methods for measuring angiogenesis are standard, and are described, for example, in Jain et al. (Nat. Rev. Cancer 2: 266-276, 2002). Angiogenesis can be assayed by measuring the number of non- branching blood vessel segments (number of segments per unit area), the functional vascular density (total length of perfused blood vessel per unit area), the vessel diameter, or the vessel volume density (total of calculated blood vessel volume based on length and diameter of each segment per unit area). Methods for measuring angiogenesis are standard in the art and are described, for example, in Jain et al., (Nat. Rev. Cancer 2: 266-276, 2002).

By "derived from" is meant the process of obtaining a progeny cell. "Derived from" also means obtained from a specified source.

By "engraft" is meant the process of cellular contact and incorporation into an existing tissue of interest (e.g., a blood vessel or microvasculature) in vivo.

By "genetically modified" is meant comprising a heterologous polynucleotide, such as an expression vector.

By "increase in angiogenesis" is meant a positive change in blood vessel formation as measured by standard assays, such as those described herein. Desirably, an agent that modulates blood vessel formation will increase blood vessel formation (e. g., angiogenesis, vasculogenesis, formation of an immature blood vessel network, blood vessel remodeling, blood vessel stabilization, blood vessel maturation, blood vessel differentiation, or establishment of a functional blood vessel network) in a neural tissue or organ or microvascular scaffold.

By "increase" is meant any positive change. Exemplary increases include 5%, 10%, 20%, 25%, 30%, 40%, or 50%, 60%, 70%, 80%, 90%, or even by as much as 100%, 150%, or 200% compared to a control. Exemplary increases also include at least 1-fold (for example, 1, 2, 3, 4, 5, 6, 7, 8, 9, 10, 20, 30, 40, 50, 60, 70, 80, 90, 100, 1000, 10,000-fold or more).

By "integrated" is meant incorporated into a tissue.

A method of "administration" useful according to the invention includes but is not limited to topical application, intravenous drip or injection, subcutaneous, intramuscular, intraperitoneal, intracranial and spinal injection, ingestion via the oral route, inhalation, trans-epithelial diffusion (such as via a drug-impregnated, adhesive patch) or by the use of an implantable, time-release drug delivery device, which may comprise a reservoir of exogenously-produced agent or may, instead, comprise cells that produce and secrete the therapeutic agent. Additional methods of administration are provided hereinbelow.

By "locally administered" is meant provided to a cell, extracellular space, tissue, organ, or circulatory vessel supplying such a cell, tissue, or organ, under conditions suitable to achieve a therapeutic effect. Typically, a cell of the invention that is "locally administered" is injected into the tissue or nearby tissue which is in need of $CD31^+$ cells for treatment, a muscle tissue comprising a neuron under conditions that provide for an increase in angiogenesis or vascularity in the neuron.

By "marker" is meant any protein or polynucleotide having an alteration in expression level or activity as compared to an appropriate control or reference that is associated with a disease or disorder.

By "pluripotent stem cell" or "multipotent stem cell" is meant a cell having the potential to differentiate into more than one cell type. Exemplary cell types include, but are not limited to, endothelial cells, smooth muscle cells, and muscle cells.

By "paracrine", as it refers to secretion, is meant secretion of various biological factors. Biological factors subject to secretion include but are not limited to cytokines and growth factors.

By "neuropathy" is meant any pathology that disrupts neural function.

By "neural function" is meant any function of the nervous system, e.g. neural signaling, neural conductance, sensorimotor function or cognitive function.

By "reference" is meant a standard or control condition. A "control subject" means a subject that is not diagnosed with, is not suspected of having, and does not have a propensity to develop a disease of interest. A "control tissue" means a tissue derived from a control subject.

By "positioned for expression" is meant that the polynucleotide of the invention (e.g., a DNA molecule) is positioned adjacent to a DNA sequence which directs transcription and, for proteins, translation of the sequence (i.e., facilitates the production of, for example, a recombinant polypeptide of the invention, or an RNA molecule).

By "propensity" is meant at risk for developing pathology. Such risk can be genetic, environmental, or behavioral.

By "expansion" is meant the propagation of a cell or cells prior to or following terminal differentiation. A cell is "expanded" when it is propagated in culture and gives rise by cell division to other cells and/or progenitor cells. Expansion of cells may occur spontaneously as cells proliferate in a culture or it may require certain growth conditions, such as a minimum cell density, cell confluence on the culture vessel surface, or the addition of chemical factors such as growth factors, differentiation factors, or signaling factors.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "isolation phenotype" is meant the structural and/or functional characteristics of a stem cell upon isolation.

By "expansion phenotype" is meant the structural and/or functional characteristics of a stem cell during or following expansion. The expansion phenotype can be identical to the isolation phenotype, or alternatively, the expansion phenotype can be more differentiated than the isolation phenotype. In one embodiment, the expansion or isolation phenotype is characterized by an alteration in the expression of a marker.

By "differentiation" is meant the developmental process of commitment to a particular cell fate. Differentiation to a particular cell fate typically includes the acquisition of characteristic markers, phenotypes, or functions (e.g., endothelial cell markers or functions).

By "isolated" is meant separated from the molecular and/or cellular components that naturally accompany the cell, polypeptide, or polynucleotide. "Isolating" a cell refers to the process of removing a cell from a sample and separating away other cells which are not the desired cell type. An isolated cell will be generally free from contamination by other cell types. Isolated cells will generally be at least 30%, 40%, 50%, 60%, 70%, 80%, 85%, 90%, 98% or 99% pure. The purity of isolated cells can also be about 50 to about 55%, about 55 to about 60%, and about 65 to about 70%. More desirably, the purity is about 70 to about 75%, about 75 to about 80%, about 80 to about 85%; and still more desirably the purity is about 85 to about 90%, about 90 to about 95%, and about 95 to about 100%.

By "mesenchymal stem cell" is meant a cell derived from the mesodermal layer that is pluripotent and can develop into a connective or supporting tissue, smooth muscle, vascular endothelium, or blood cells.

As used herein, the terms "prevent," "preventing," "prevention," "prophylactic treatment" and the like refer to decreasing the probability of developing a disorder or condition in a subject, who does not have, but is at risk of or susceptible to developing a disorder or condition.

By "progenitor cell" is meant a multipotent stem cell that is capable of generating (e.g., by differentiation or division) a differentiated cell. An endothelial progenitor cell that is capable of generating an endothelial cell may express this capability when grown under appropriate in vitro or in vivo conditions, such as those described herein.

By "stem cell" is meant a cell capable of giving rise to one or more cell types.

By "differentiated cell" is meant a cell that expresses one or more markers characteristic of a particular differentiated cell type or exhibits at least one biological function associated with a differentiated cell type.

By "progeny" is meant a cell derived from a multipotent stem cell of the invention. Progeny include without limitation progenitor cells, differentiated cells, and terminally differentiated cells.

By "tissue" is meant a collection of cells having a similar morphology and function.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated. Additionally, by "treating" is meant preventing disease (for example a disease including but not limited to myocardial infarction, congestive heart failure, peripheral vascular obstructive disease, ischemia, limb ischemia, stroke, transient ischemia, reperfusion injury, peripheral neuropathy, toxic neuropathy, diabetic dementia, or autonomic neuropathy, liver failure, renal failure, diabetes, rheumatoid arthritis, osteoarthritis, and osteoporosis in a subject at risk thereof.

As used herein, "diagnosis" refers to a process of determining if an individual is afflicted with a disease or ailment, for example myocardial infarction, congestive heart failure, peripheral vascular obstructive disease, ischemia, limb ischemia, stroke, transient ischemia, reperfusion injury, peripheral neuropathy, toxic neuropathy, diabetic dementia, or autonomic neuropathy, liver failure, renal failure, diabetes, rheumatoid arthritis, osteoarthritis, and osteoporosis.

By "therapeutic polypeptide" means a protein or analog thereof that has the potential of positively affecting the function of an organism. A therapeutic polypeptide may decrease, suppress, attenuate, diminish, arrest, or stabilize the development or progression of disease, disorder, in an organism. In various embodiments, therapeutic polypeptides (e.g., angiogenic factors, neurotrophic factors, pleiotrophic factors) support neuronal or endothelial cell survival, growth, or proliferation.

By "therapeutically effective amount" is meant the amount required to ameliorate the symptoms of a disease relative to an untreated patient. The effective amount of active compound(s) used to practice the present invention for therapeutic treatment of a neuropathy varies depending upon the manner of administration, the age, body weight, and general health of the subject. Ultimately, the attending physician or veterinarian will decide the appropriate amount and dosage regimen. Such amount is referred to as an "effective" amount.

By "agent" is meant a polypeptide, polynucleotide or small compound. Polypeptide agents include growth factors, cytokines, hormones or small molecules, or to genetically-encoded products that modulate cell function (e.g., induce cell fate, increase expansion, inhibit or promote cell growth and survival). For example, "expansion agents" are agents that increase proliferation and/or survival of stem cells. "Differentiation agents" are agents that induce differentiation into committed cell lineages.

By "subject" is meant any warm-blooded animal including but not limited to a human, cow, horse, pig, sheep, goat, bird, mouse, rat, dog, cat, monkey, baboon, or the like.

By "subject in need" is meant a warm-blooded animal that is diagnosed with a disease, for example including but not limited to myocardial infarction, congestive heart failure, peripheral vascular obstructive disease, ischemia, limb ischemia, stroke, transient ischemia, reperfusion injury, peripheral neuropathy, toxic neuropathy, diabetic dementia, or autonomic neuropathy, liver failure, renal failure, diabetes, rheumatoid arthritis, osteoarthritis, and osteoporosis.

A "subject in need" also means a warm-blooded animal that is suspected of having a disease including but not limited to myocardial infarction, congestive heart failure, peripheral vascular obstructive disease, ischemia, limb ischemia, stroke, transient ischemia, reperfusion injury, peripheral neuropathy, toxic neuropathy, diabetic dementia, or autonomic neuropathy, liver failure, renal failure, diabetes, rheumatoid arthritis, osteoarthritis, and osteoporosis.

The term "obtaining" as in "obtaining the agent" is intended to include purchasing, synthesizing or otherwise acquiring the agent (or indicated substance or material).

The terms "comprises", "comprising", and are intended to have the broad meaning ascribed to them in U.S. Patent Law and can mean "includes", "including" and the like.

By "octamer-binding transcription factor 4 (Oct4) polypeptide" is meant a transcription factor having at least 85% identity to GenBank Accession No. NP_976034 or NP_002692 that regulates tissue-specific gene expression.

By "octamer-binding transcription factor 4 (Oct4) nucleic acid sequence" is meant a polynucleotide encoding a Oct4 polypeptide.

By "RNA exonuclease 4 (Rex4) polypeptide" is meant a polypeptide having at least 85% identity to NP_065118 that functions in mitosis.

By "RNA exonuclease 4 (Rex4) nucleic acid sequence" is meant a polynucleotide encoding a Rex4 polypeptide.

By "nanog polypeptide" is meant a polypeptide having at least 85% homology to NP_079141 that functions in maintaining the pluripotency of a nanog expressing cells.

By "nanog nucleic acid sequence" is meant a polynucleotide encoding a nanog protein.

By "sex-determining region Y-box 2 polypeptide (Sox2)" is meant a transcription factor having at least 85% identity to GenBank Accession No. NP_003097 that functions in eye or neural development.

By "Sox2 nucleic acid sequence" is meant a polynucleotide encoding a Sox2 polypeptide.

By "Stage Specific Embryonic Antigen-1 (SSEA-1) polypeptide is meant a polypeptide having at least 85% identity to GenBank Accession No. NP_034372 or a human homolog thereof that acts as a marker for primitive progenitor cells present in a mesodermal population.

By "SSEA-1 nucleic acid sequence" is meant a polynucleotide encoding a SSEA-1 polypeptide.

By "vascularization" is meant any biological process that increases the perfusion of tissue or organ.

BRIEF DESCRIPTION OF THE DRAWINGS

FIG. 1L shows the results of FACS analysis after lineage depletion. A positive portion of other stem cell markers also share CD31 co-expression. CD31$^+$ cells contain a high proportion of hematopoetic (CD34+, c-kit+) and vasculogenic (Flk1+) stem cells.

FIG. 1M shows c-kit.

FIG. 1N shows Flk.

FIG. 3A shows a control.

FIG. 3B shows CD31 negative.

FIG. 8 is a graph showing the percent distribution of transplants having final limb salvage among 3 groups. (n=7, each).

FIG. 10A shows representative lectin staining (left) and merged images with DAPI (right).

FIG. 11A shows the fate of CD31$^+$ cells after 14 days transplantation into ischemic limb. CD31$^+$ cells from GFP expressing mice were incorporated into vasculature as shown. Representative images stained for GFP (Anti-GFP antibody), lectin binding, and nuclear counterstain (DAPI) demonstrate incorporation into endothelial cells (arrow head) and pericytes location (arrow).

FIG. 11B shows the fate of CD31$^+$ cells after 14 days transplantation into ischemic limb. D31$^+$ cells after 14 days transplantation into ischemic limb.

FIG. 11C shows the fate of CD31$^+$ cells after 14 days transplantation into ischemic limb. D31$^+$ cells after 14 days transplantation into ischemic limb.

FIG. 14D The quantification showed a perfusion improvement. *P=0.007 (CD31+ vs PBS) (n=4, each)

FIG. 15A shows the histology analysis of an ischemic limb. Capillary densities were measured at 14 days. Administration of CD31$^+$ cells increased capillary densities in ischemic tissue. A. Representative lectin staining and merged images with DAPI.

FIG. 15B. Quantitative analysis of capillary density was expressed as the number of lection-positive cells per mm$^2$. *P=0.001, PBS vs. CD31+; **P=0.002, CD31− vs. CD31+. (n=5, each)

FIG. 24G shows CD31.
FIG. 24H shows IL-1.
FIG. 24I shows IL-6.
FIG. 24J shows IL-10.
FIG. 24K shows IFN-gamma.

FIG. 31E shows in vitro culture of Lin-CD31+ Sca-1+ cells.

DETAILED DESCRIPTION OF THE INVENTION

Figure 1A:
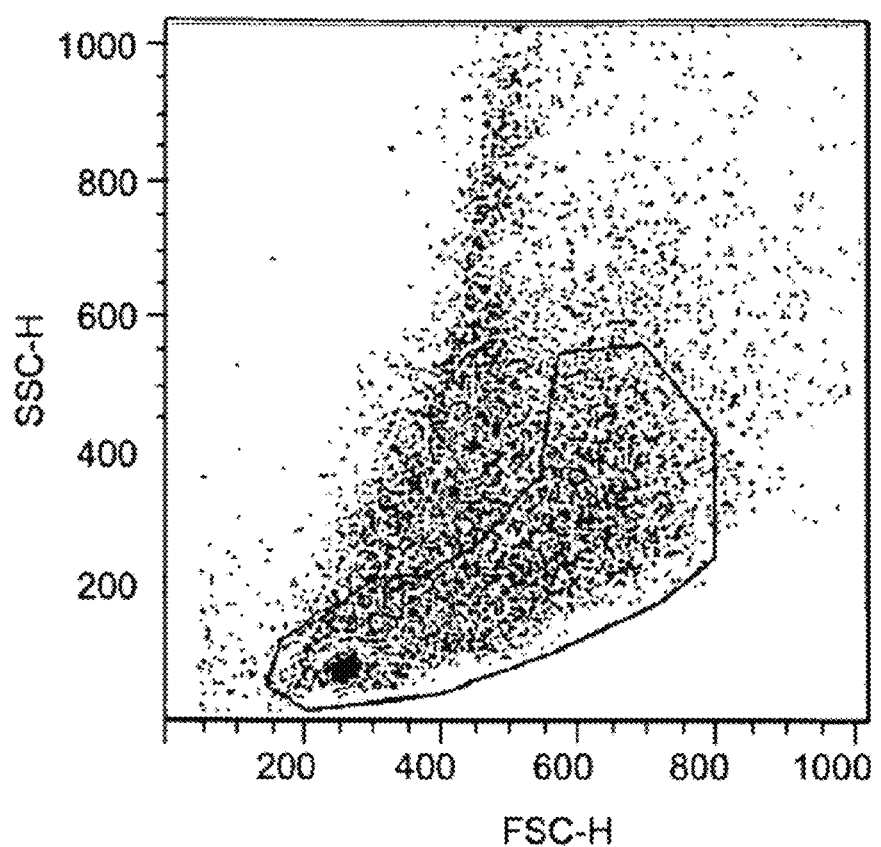
FIG. 1A shows the results of flow cytometry analysis characterizing bone marrow mononuclear cells. The C57BL/6J BM– mononuclear cell fractions were analyzed by flow cytometry. At least 10,000 cells were gated in each case.
Figure 1B:
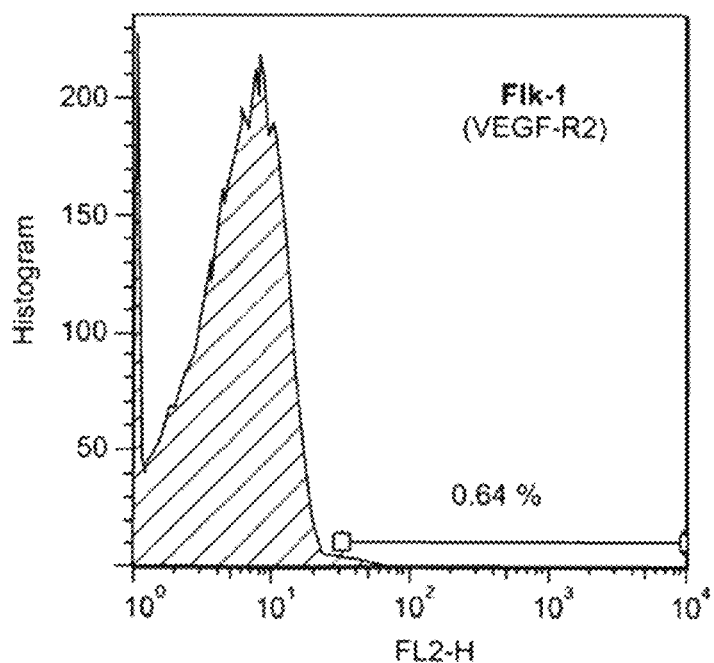
FIG. 1B shows Flk-2.
Figure 1C:
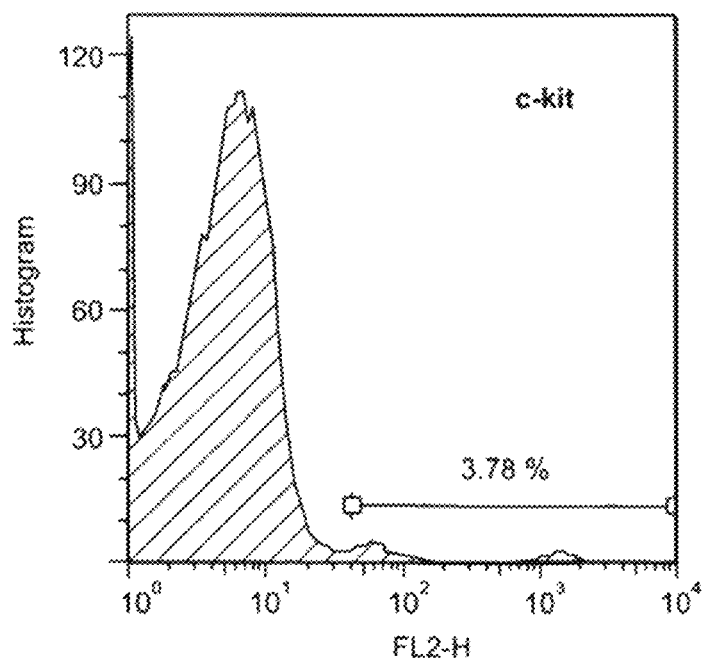
FIG. 1C shows c-kit.
Figure 1D:
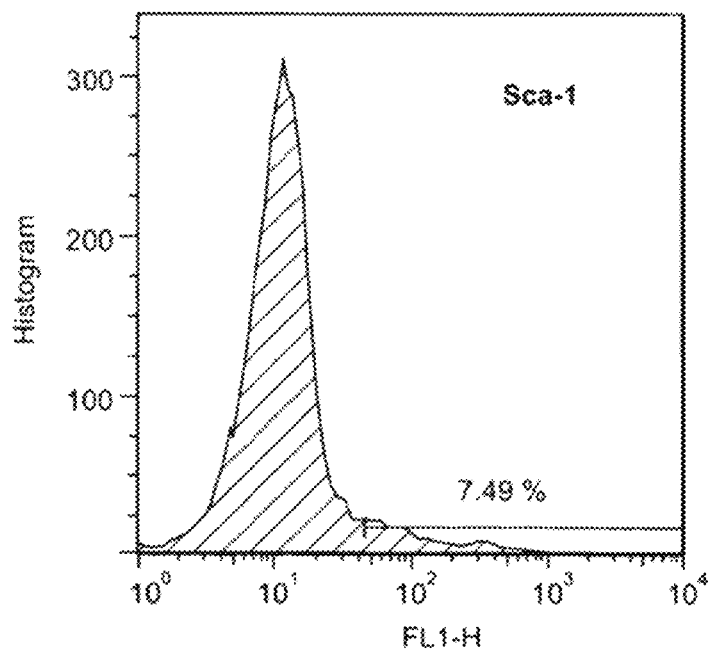
FIG. 1D shows Sca-1.
Figure 1E:
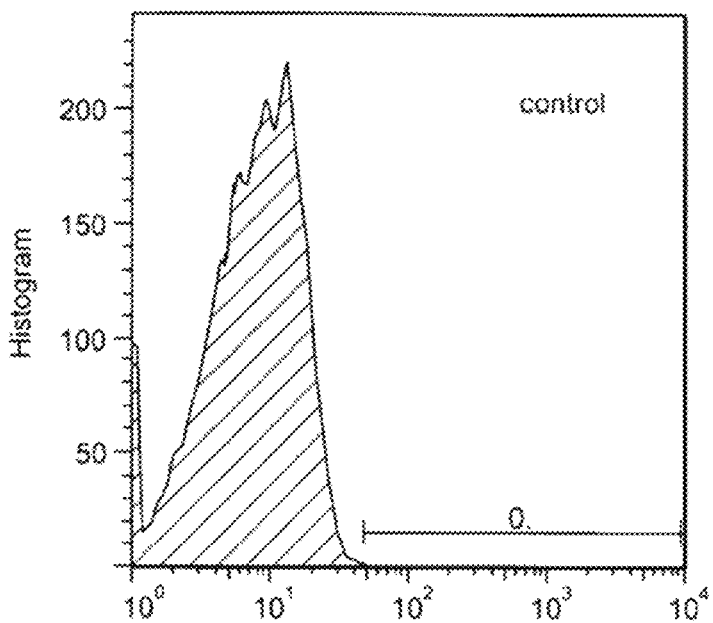
FIG. 1E shows a control.
Figure 1F:
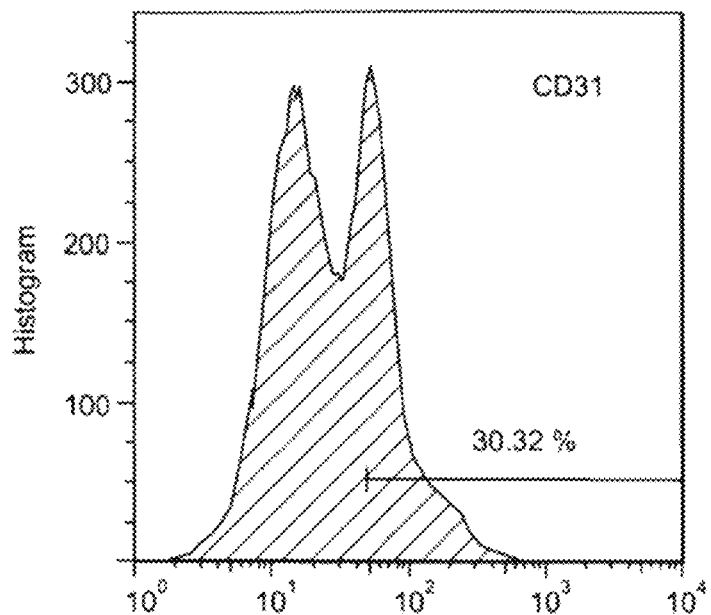
FIG. 1F includes histograms showing that CD31-expressing cells make up 30% of the cells, in contrast to other well-known stem cell markers which are expressed in very limited numbers of cells.
Figure 1G:
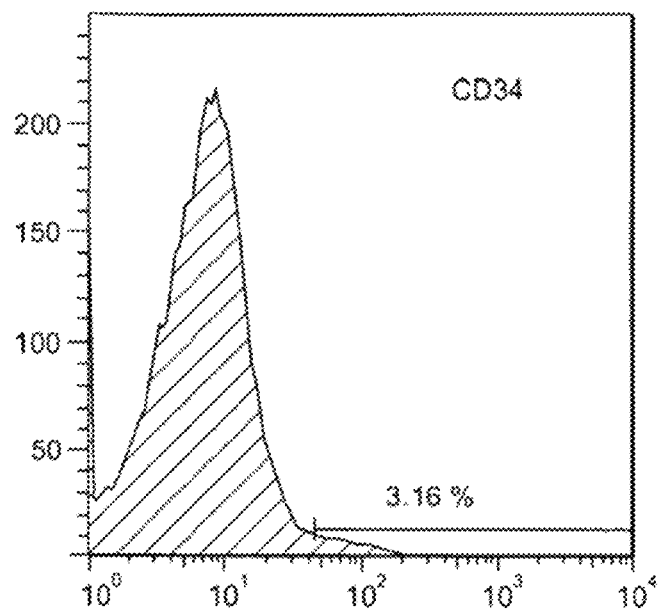
FIG. 1G shows CD34.
Figure 1H:
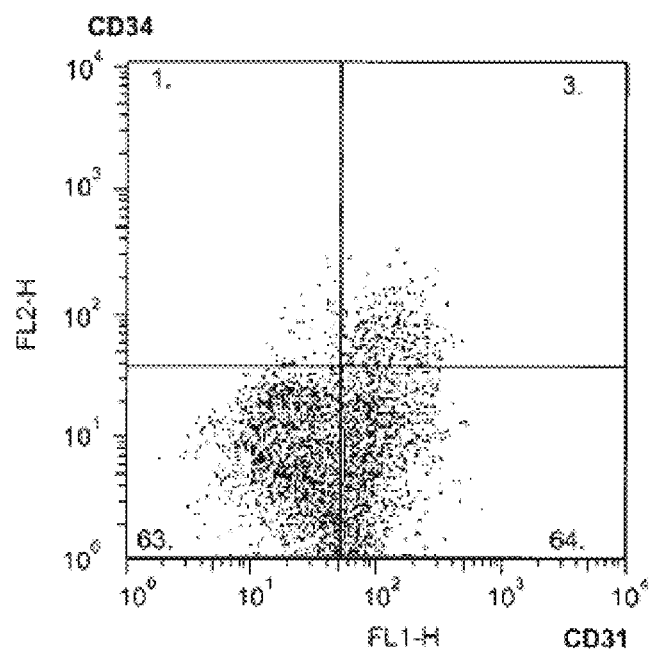
FIG. 1H shows the results of FACS double staining demonstrating that CD34expressing cells are also expressing CD31.

The invention features compositions and methods related to the isolation, culture and therapeutic use of CD31-expressing cells. The invention is based, at least in part, on the discovery that CD31 or PECAM-1, which has been generally regarded as an endothelial cell marker, is a surface epitope common to most stem or progenitor cells that have been shown to have therapeutic effects in cardiovascular regeneration or repair. Moreover, lineage negative, CD31 positive cells include pluripotent hematopoietic stem cells which can differentiate into a variety of lineages of hematopoietic cells and are useful for treating various hematologic diseases. Furthermore, developmental studies using embryonic stem cells have demonstrated that CD31 is not merely a marker for endothelial lineage differentiation but a maker for multipotent stem cells.

Accordingly, BM-derived CD31-positive cells were characterized and the therapeutic use of these cells has been determined. BM-derived CD31-positive cells are useful for regenerating or repairing tissues affected by a variety of diseases characterized by an increase in cell death or a decrease in cell number or function. In particular, CD31$^+$ cell transplantation is useful for repairing ischemic limb and heart and useful for reconstituting hematopoietic cells following whole body irradiation required in bone marrow transplantation. Such cells may also be used for the treatment or prevention of cardiovascular diseases, such as myocardial infarction, congestive heart failure, peripheral vascular obstructive diseases, various types of peripheral neuropathies including but not limited to diabetic, ischemic, toxic or chemical-induced neuropathies, stroke (cerebrovascular diseases), liver failure, renal failure, islet cell transplantation, bone and joint diseases or any degenerative disease which requires stem cell therapy.

CD31

Platelet endothelial cell adhesion molecule (PECAM)-1 is a 130-kDa type I transmembrane glycoprotein (GP) that was originally described as the endothelial cell equivalent of platelet membrane GPIIa (the integrin (β1 subunit) and a myeloid differentiation antigen. The common identity of these previously disparate entities as PECAM-1 or CD31 was finally established in 1990 upon its cloning by 3 different groups. The CD31 antigen has been known to present on the cell-cell junctions of endothelial cells and surface of hematopoietic cells including monocytes, granulocytes, natural killer cells, naïve T and cells and platelets[43-46]. In general, CD31 has served as an immunochemical marker to identify endothelial cells in histological sections or to mark angiogenic blood vessels.

Recently other roles for CD31 have been suggested. CD31 may work as a key mediator of the migration of cells in the process of angiogenesis. For example, an antibody against murine CD31 inhibits tumor angiogenesis in a mouse model as well as capillary growth into subcutaneously implanted gels supplemented with bFGF. The preliminary characterization of CD31-deficient mice (CD31-KO) also focused on a functional evaluation of CD31 in the context of inflammatory adhesion-dependent cascades and not in the context of an angio-vasculogensis[48]. Interestingly, CD31-KO mice are viable, remain healthy, and exhibit no obvious vascular developmental defects during embryonic development. In vascular biology, CD31 mediates the arteriolar dilation in response to wall shear stress in a nitrous oxide (NO)-dependent manner. Previous studies failed to recognize that CD31 could serve as a stem cell marker or function in postnatal adult vasculogenesis/myogenesis. As reported in more detail below, CD31 serves as a comprehensive epitope that is expressed in various subsets of hemangioblastic cells in adult bone marrow (BM).

The amino acid sequence of an exemplary CD31 polypeptide is provided at GenBank Accession No. NP_000433.

Lineage negative CD31 is a marker for a population of multipotent stem cells. CD31$^+$ cells were isolated with the use of magnetic cell isolation system and antibodies that recognized CD31 and a cocktail of various hematopoietic lineage markers. In addition, methods for maintaining CD31$^+$ cells in culture dishes. Compared to the other cells, lineage negative CD31 positive cells were easier to isolate and have similar or superior multipotency and therapeutic capacity. Lineage negative, CD31-positive bone marrow cells are multipotent and possess angiogenic and regenerative capacity. These cells can be therapeutically employed in a variety of cardiovascular and other diseases.

Ischemic Disease

Ischemia refers to a condition characterized by oxygen deficiency. Typically ischemia is related to insufficient circulation. Ischemia can affect virtually any organ in the body, including but not limited to muscle tissues, organs, and neural tissues. Neural ischemias include transient ischemia, stroke, and reperfusion injury. In intestinal ischemia blood supply to the intestine is reduced resulting in tissue damage. Ischemic colitis involves an area of inflammation (irritation and swelling) caused by interference with the blood flow to the colon. Cardiac ischemia is associated with myocardial infarction and congestive heart failure. Limb ischemia is associated with peripheral vascular obstructive disease.

Cardiovascular Function

Cardiac conditions, such as myocardial infarction, congestive heart failure, peripheral vascular obstructive disease, cardiac hypertrophy, reduced systolic function, reduced diastolic function, maladaptive hypertrophy, heart failure with preserved systolic function, diastolic heart failure, hypertensive heart disease, aortic and mitral valve disease, and pulmonary valve disease are associated with ischemia-related tissue damage and/or reduced cardiac function. Compositions of the invention containing a CD31$^+$ cell may be used to enhance angiogenesis in a cardiac tissue or to increase cardiac function in a subject having reduced cardiac function. Desirably, cardiac function is increased by at least 5%, 10% or 20%, or even by as much as 25%, 50% or 75%. Most advantageously, cardiac function is increased relative to the function of an untreated control. Treatments that increase cardiac function are useful in the methods of the invention.

Any number of standard methods are available for assaying cardiovascular function. Preferably, cardiovascular function in a subject (e.g., a human) is assessed using non-invasive means, such as measuring net cardiac ejection (ejection fraction, fractional shortening, and ventricular endsystolic volume) by an imaging method such echocardiography, nuclear or radiocontrast ventriculography, or magnetic resonance imaging, and systolic tissue velocity as measured by tissue Doppler imaging. Systolic contractility can also be measured non-invasively using blood pressure measurements combined with assessment of heart outflow (to assess power), or with volumes (to assess peak muscle stiffening). Measures of cardiovascular diastolic function include ventricular compliance, which is typically measured by the simultaneous measurement of pressure and volume, early diastolic left ventricular filling rate and relaxation rate (can be assessed from echo-Doppler measurements). Other measures of cardiac function include myocardial contractility, resting stroke volume, resting heart rate, resting cardiac index (cardiac output per unit of time [L/minute], measured while seated and divided by body surface area [$m^2$])) total aerobic capacity, cardiovascular performance during exercise, peak exercise capacity, peak oxygen ($O_2$) consumption, or by any other method known in the art or described herein. Measures of vascular function include determination of total ventricular afterload, which depends on a number of factors, including peripheral vascular resistance, aortic impedance, arterial compliance, wave reflections, and aortic pulse wave velocity, Methods for assaying cardiovascular function include any one or more of the following: Doppler echocardiography, 2-dimensional echo-Doppler imaging, pulse-wave Doppler, continuous wave Doppler, oscillometric arm cuff, tissue Doppler imaging, cardiac catheterization, magnetic resonance imaging, positron emission tomography, chest X-ray, X-ray contrast ventriculography, nuclear imaging ventriculography, computed tomography imaging, rapid spiral computerized tomographic imaging, 3-D echocardiography, invasive cardiac pressures, invasive cardiac flows, invasive cardiac pressure-volume loops (conductance catheter), non-invasive cardiac pressure-volume loops.

Neuropathy

Neuropathies are pathologies that disrupt neural function. There is a marked reduction of the microvasculature (vasa nervorum) in diabetic peripheral neuropathy, particularly. Impaired angiogenesis, in particular, attenuation of the vasa nervorum, has been noted in models of diabetes. Microvascular insufficiency and neurotrophic factor deficiency plays a role in the development and progression of diabetic peripheral neuropathy, as does ischemia in diabetic nerves (Dyck P J, 1989, Neurology; Steven E J, 1994, Diabetologia), inactivation of proteins critical to neural function (Cullum N A, 1991, Diabetologia) and altered neural polyol metabolism (Greene D A, 1987, NEJM; Cameron N E, 1994, Diabetes Metab. Rev). Diabetic neuropathy can be reversed by agents promoting angiogenesis such as VEGF-1 and -2 (Schratzberger et al., *J Clin Invest*. May 2001;107(9):1083-1092), sonic hedgehog (SHh) (Kusano et al., *Arterioscler Thromb Vasc Biol*. November 2004;24(11):2102-2107), and a statin (Ii et al., *Circulation*. Jul. 5, 2005 2005;112(1):93-102). Furthermore, promising results from a pilot clinical trial (Simovic et al., *Arch Neurol*. May 2001;58(5):761-768; Isner et al., *Hum Gene Ther*. Aug. 10 2001;12(12):1593-1594) using a plasmid encoding human VEGF (phVEGF) via gene therapy approach for patients with DPN also support the importance of vascular supply in the pathogenesis of DPN.

Exemplary neuropathies include but are not limited to diabetic neuropathy, ischemic neuropathy, toxic neuropathy, diabetic dementia. Symptoms of neuropathy vary depending on whether the affected nerves are sensory, motor, or autonomic. Neuropathy can affect any one or a combination of all three types of nerves. Typically, symptoms of neuropathy include pain, loss of sensation, or inability to control muscles. Methods of assaying neuropathy include electromyography, nerve conduction velocity tests, nerve biopsy, and other standard clinical assays for neurological function. Peripheral neuropathy is characterized by an abnormal neurological exam, subjective symptoms, abnormal biothesiometry, or abnormal nerve conduction study. Autonomic neuropathy is characterized by an abnormal R-R interval, orthostatic hypotension, or resting tachycardia.

Neuropathy may be caused by a hereditary disorder (e.g., Charcot-Marie-Tooth disease, Friedreich's ataxia), an infectious or inflammatory conditions (e.g., rheumatoid arthritis, Lyme disease, AIDs), exposure to agents that are toxic to neurons (e.g., heavy metals, such as lead), or systemic or metabolic disorders, such as diabetes.

As reported in more detail below, the present invention provides compositions and methods for treating or preventing neuropathies, including diabetic neuropathy, by increasing angiogenesis in the microvasculature of nerves. The invention is based, in part, on the discovery that the local implantation of multipotent stem cells, such as endothelial progenitor cells, mesenchymal stem cells, and peripheral blood mononuclear cells, increases vascularity, conduction velocity, cytokine or therapeutic polypeptide expression, Schwann and endothelial cell proliferation, and decreases apoptosis in nerves affected by neuropathy.

Therapeutic and Prophylactic Methods

The invention provides for the treatment of diseases and disorders associated with an increase in cell death or a decrease in cell number. In particular, $CD31^+$ expressing cells are useful for the treatment of liver failure, renal failure, islet cell transplantation, bone and joint diseases or any degenerative disease which could benefit from stem cell therapy.

Many diseases associated with a deficiency in cell number are characterized by an increase in cell death. For example, the invention provides compositions for the treatment of diabetic patients who lack sufficient levels of insulin due to a decrease in the number or activity of insulin producing pancreatic cells. Such diseases include, but are not limited to, neurodegenerative disorders, stroke, myocardial infarction, or ischemic injury. Injuries associated with trauma can also result in a deficiency in cell number in the area sustaining the wound. Methods of the invention ameliorate such diseases, disorders, or injuries by generating cells that can supplement the deficiency. Such cells are generated from the transdifferentiation of a $CD31^+$ bone marrow cell to a cell type of interest (e.g., the transdifferentiation of a $CD31^+$ expressing cell to an endothelial cell, an insulin producing cell, a bone cell, a liver cell, a renal cell) or by promoting the regeneration of a cell, tissue, or organ.

In one embodiment, a $CD31^+$ expressing stem cell of the invention is administered to a cell, tissue, or organ in situ to ameliorate a deficiency in cell number. Alternatively, the $CD31^+$ expressing stem cell is administered to a tissue in vitro and then the $CD31^+$ expressing stem cell are administered to the patient to ameliorate a disease, disorder, or injury. In one embodiment, a $CD31^+$ expressing stem cell is delivered locally to a site where an increase in angiogenesis or tissue repair is desired. Administration may be by any means sufficient to result in a therapeutic effect. In various embodiments, $CD31^+$ expressing stem cell are administered by local injection to a site of disease or injury, by sustained infusion, or by micro-injection under surgical conditions (Wolff et al., Science 247:1465, 1990). In other embodiments, the $CD31^+$ expressing stem cells are administered systemically to a tissue or organ of a patient having a deficiency in cell number that can be ameliorated by cell regeneration.

CD31$^+$ cells having the potential to differentiate into endothelial cells (e.g., multipotent stem cells, endothelial progenitor cells, mesenchymal stem cells, mononuclear cells, or progenitors or progeny thereof) can be used in a variety of therapeutic or prophylactic applications. Accordingly, methods of the invention relate to, among other things, the use of multipotent stem cells, endothelial progenitor cells, mesenchymal stem cells, mononuclear cells, or progenitors or progeny thereof for the treatment or prevention of ischemic diseases (e.g., myocardial infarction, limb ischemia, stroke, transient ischemia, reperfusion injury) neuropathies (e.g., diabetic peripheral neuropathy, toxic neuropathy), liver failure, renal failure, diabetes, bone and joint diseases or any degenerative disease which requires stem cell therapy.

In one embodiment, the present invention provides methods for treating neuropathy comprising providing a cell having the potential to differentiate into an endothelial cell (e.g., multipotent stem cells, endothelial progenitor cells, mesenchymal stem cells, mononuclear cells, or progenitors or progeny thereof) to a subject in need thereof, wherein the cell engrafts into a tissue (e.g., a neural tissue) and enhances angiogenesis in a neural tissue of interest. In one embodiment, the present invention provides methods for treating neuropathy comprising providing a cell having the potential to differentiate into an endothelial cell (e.g., multipotent stem cells, endothelial progenitor cells, mesenchymal stem cells, mononuclear cells, or progenitors or progeny thereof) to a subject in need thereof, wherein the cell engrafts into the microvasculature of a neural tissue of interest and increases angiogenesis, vascularity, or the biological function of the neural tissue. In yet another embodiment, the method provides a cell having the potential to differentiate into an endothelial cell (e.g., multipotent stem cells, endothelial progenitor cells, mesenchymal stem cells, mononuclear cells, or progenitors or progeny thereof) to a subject in need thereof, wherein the cell augments a humoral response in the neural tissue sufficient to exert a therapeutic effect (e.g., an increase in paracrine factors, neurotrophic factors, angiogenic factors, or an increase in angiogenesis).

The present invention also provides methods for restoring neural function in a diabetic subject having a loss of neural function (e.g., motor or sensory deficit), comprising providing a cell having the potential to differentiate into an endothelial cell and a neural cell (e.g., multipotent stem cells, endothelial progenitor cells, mesenchymal stem cells, mononuclear cells, or progenitors or progeny thereof) to the subject to enhance neural function.

In another embodiment, the invention provides methods for treating liver failure, renal failure, or diabetes comprising providing a cell having the potential to transdifferentiate into a liver cell, renal cell, or insulin producing cell (e.g., a pancreatic islet cell) to a subject in need thereof, wherein the cell engrafts into a tissue of the subject and repairs or regenerates the tissue.

In general, the sample comprising the CD31$^+$ cells can be pretreated in a wide variety of ways. Generally, once collected, the cells can be additionally concentrated, if this was not done simultaneously with collection or to further purify and/or concentrate the cells. The cells may be washed, counted, and resuspended in buffer transferred to a sterile, closed system for further purification and activation.

The CD31$^+$ cells are generally concentrated for treatment, using standard techniques in the art. In a preferred embodiment, the leukophoresis collection step results in a concentrated sample of CD31$^+$ cells, in a sterile leukopak, that may contain reagents or doses of a suppressive composition. Generally, an additional concentration/purification step is done, such as Ficoll-Hypaque density gradient centrifugation as is known in the art. Separation or concentration procedures include but are not limited to magnetic separation, using antibody-coated magnetic beads, affinity chromatography, cytotoxic agents, either joined to a monoclonal antibody or used with complement, "panning", which uses a monoclonal antibody a to a solid matrix. Antibodies attached to solid matrices, such as magnetic beads, agarose beads, polystyrene beads, follow fiber membranes and plastic surfaces allow for direct separation. Cells bound by, antibody can be removed or concentration by physically separating the solid support from the cell suspension. The exact conditions and procedure depend on factors specific to the system employed. The selection of appropriate conditions is well within the skill in the art.

Antibodies may be conjugated to biotin, which then can be removed with avidin or streptavidin bound to a support, or fluorochromes, which can be used with a fluorescence activated cell sorter (FACS), to enable cell separation. Any technique may be employed as long as it is not detrimental to the viability of the desired cells.

In a preferred embodiment, the CD31$^+$ cells are separated in an automated, closed system such as the Nexell Isolex 300i Magnetic Cell Selection System. Generally, this is done to maintain sterility and to insure standardization of the methodology used for cell separation, activation and development of suppressor cell function.

Once purified or concentrated the cells may be aliquoted and frozen, preferably, in liquid nitrogen or used immediately as described below. Frozen cells may be thawed and used as needed. Cryoprotective agents, which can be used, include but are not limited to dimethyl sulfoxide (DMSO) (Lovelock, J. E. and Bishop, M. W. H., 1959, Nature 183:1394-1395; Ashwood-Smith, M. J., 1961, Nature 190: 1204-1205), hetastarch, glycerol, polyvinylpyrrolidine (Rinfret, A. P., 1960, Ann. N.Y. Acad. Sci. 85:576), polyethylene glycol (Sloviter, H. A. and Ravdin, R. G., 1962, Nature 196:548), albumin, dextran, sucrose, ethylene glycol, i-erythritol, D-ribitol, D-mannitol (Rowe, A. W., et al., 1962, Fed. Proc. 21:157), D-sorbitol, i-inositol, D-lactose, choline chloride (Bender, M. A., et al., 1960, J. Appl. Physiol. 15:520), amino acids (Phan The Tran and Bender, M. A, 1960, Exp. Cell Res. 20:851), methanol, acetamide, glycerol monoacetate (Lovelock. J. E., 1954, Biochem. J. 56:265), and inorganic salts (Phan The Tran and Bender, M. A., 1960, Proc. Soc. Exp. Biol. Med. 104:388; Phan The Tran and Bender, M. A., 1961, in Radiobiology Proceedings of the Third Australian Conference on Radiobiology, Ilbery, P. L. T., ed., Butterworth, London, p. 59). Typically, the cells may be stored in 10% DMSO, 50% serum, and 40% RPMI 1640 medium. Methods of cell separation and purification are found in U.S. Pat. No. 5,888,499, which is expressly incorporated by reference.

In a preferred embodiment, the CD31$^+$ cells are then washed to remove serum proteins and soluble blood components, such as autoantibodies, inhibitors, etc., using techniques well known in the art. Generally, this involves addition of physiological media or buffer, followed by centrifugation. This may be repeated as necessary. They can be resuspended in physiological media, preferably AIM-V serum free medium (Life Technologies) (since serum contains significant amounts of inhibitors of TGF-β) although buffers such as Hanks balanced salt solution (HBBS) or physiological buffered saline (PBS) can also be used.

Generally, the cells are then counted; in general from $1\times10^9$ to $2\times10^9$ white blood cells are collected from a 5-7 liter leukophoresis step. These cells are brought up to roughly 200 mls of buffer or media.

Compositions comprising peripheral blood derived stem cells or their progenitors can be provided directly to a tissue of interest. Alternatively, compositions comprising stem cells or their progenitors can be provided indirectly to the tissue of interest, for example, by administration into the circulatory system or injection into a skeletal or cardiac muscle.

CD31$^+$ Cells Engraftment

As described in more detail below, the present invention provides methods for preventing or treating ishemic diseases (e.g., myocardial infarction, limb ischemia, stroke, transient ischemia, reperfusion injury) neuropathies (e.g., diabetic peripheral neuropathy, toxic neuropathy), liver failure, renal failure, diabetes, bone and joint diseases or any degenerative disease which requires stem cell therapy by locally or systemically administering a cell having the potential to differentiate into an endothelial cell, endothelial progenitor cell, mesenchymal stem cell, mononuclear cell, liver cell, renal cell, neural cell, skin cell, cells derived from eye tissue, insulin producing cell, or progenitors or progeny thereof directly or indirectly to the tissue in need of therapy. In one embodiment, this administration results in the incorporation of the cell into a tissue (e.g., a tissue comprising differentiated somatic cells, extracellular matrix, and supporting cells, such as cells of the vasculature that supply the tissue). Without wishing to be bound by theory, it is likely that cells of the invention home to tissue that lacks sufficient vascularity and are incorporated into that tissue. In one embodiment, the cells differentiate into mature endothelial cells and contribute to the vasculature of the neural, skeletal muscle, cardiac muscle or skin tissue. Methods for detecting differentiated endothelial cells are known in the art, see, for example, U.S. Pat. No. 5,980,887 and WO 99/45775, which describe methods for detecting and monitoring endothelial cell function. A preferred assay involves detection of EC specific markers (e.g., VE-Cadherin, CD34, Flk-1, Tie2 and CD31, VonWillebrand Factor or factor 8).

CD31$^+$ Cells

CD31$^+$ stem cells are isolated by standard means known in the art for the separation of stem cells from the bone marrow, peripheral blood and umbilical cord blood. In particular, methods of the invention provide for the isolation of a CD31$^+$ expressing stem cell.

The invention encompasses CD31+ cells that are uncultured or cultured. "Uncultured" as it refers to CD31+ cells means a population of CD31+ cells that has not been cultured as defined herein. "Uncultured" CD31+ cells means the total population of mononuclear cells derived from any one of bone marrow, peripheral blood or umbilical cord blood. "Uncultured" CD31+ cells also means cells that have been subjected to a step wherein total CD31+ cells are isolated, for example, magnetic cell sorting.

As used herein, a "cultured CD31$^+$ cell" is a cell that has been grown in vitro. For example, subjected to a step where total CD31" cells are isolated and at least one additional culture step is carried out, for example, expansion, wherein the number of cells is increased while the surface marker expression is unchanged, or undergoes a low level of change; or differentiation, wherein cells are cultured under conditions which promote formation of any one of hematopoietic stem cells (non-adherent), endothelial progenitor cells (adherent and non-adherent) and mesenchymal progenitor cells (adherent) is performed.

In one embodiment, "culturing" includes a step of selecting for lin$^-$ cells.

In one embodiment, CD31$^+$ expressing stem cells useful in the methods of the invention are obtained from the bone marrow of a human patient. Typically, the method includes at least one or more of the following steps:

a) collecting bone marrow cells from a mammal (e.g., a young adult), where the cells have a size of less than about 100 microns, less than about 50 microns, or about 40 microns or less, b) culturing (expanding) the collected cells in medium under conditions that select for adherent cells, c) selecting the adherent cells and expanding those cells in medium to semi-confluency, d) serially diluting the cultured cells into chambers with conditioned medium, the dilution being sufficient to produce a density of less than about 1 cell per chamber to make clonal isolates of the expanded cells; and e) culturing (expanding) each of the clonal isolates and selecting chambers having expanded cells to make the population of isolated bone marrow cells.

In another embodiment, hemangioblastic cells having the potential to differentiate into hematopoietic cells or endothelial cells (e.g., multipotent stem cells, endothelial progenitor cells, mononuclear cells, mesenchymal stem cells, and their progenitor or progeny cells) are obtained by extracting fresh unprocessed bone marrow cells from young donors. The cells are typically separated from blood cells by centrifugation, hemolysis and related standard procedures described herein. The bone marrow cells are washed in an acceptable buffer such as PBS and filtered to collect cells having a size less that about 100 microns, less than about 50 microns, or about 40 microns. Methods for size selection are known in the art. In one embodiment, a standard nylon filter is used. Once isolated, cells of the selected size are grown on a complete culture medium with low or high glucose (e.g., DMEM) that contains a rich source of growth factors and cytokines. Fetal bovine serum (FBS) is typically used in the culture medium. Cells are cultured (i.e. expanded) for less than about two weeks, preferably about a week or less such as four to six days. The conditioned medium is then replaced with fresh medium; adherent cells are removed from the culture dishes and resuspended in fresh medium to select cells for expansion. The selected cells are grown to semi-confluency (between 50% to 90% confluent) and again, adherent cells are selected. Such cells are then reseeded in complete medium in a tissue culture flask at a density of about $10^4$ cells per centimeter. After the cells reach semi-confluency, they are reseeded (serially) into the flasks at the same or similar density. The cultures are preferably passaged more than one time, typically less than five times and preferably about two times to continue selection for expanding cells. Selected cells are then serially diluted into single well chambers (e.g., standard 96 well plate) at a density of less than about 1 cell per chamber, preferably $1/2$ a cell per chamber. Preferably, the cells are cultured with conditioned media to promote growth to sub confluence (i.e. less then 50% confluent). Wells with expanded cell clones are expanded and replated as needed.

If desired, cell clones are selected that express a normal or an altered level (e.g., increased or decreased level) of at least one of the following markers: CD90, CD117, CD34, CD113, FLK-1, tie-2, Oct 4, GATA-4, NKx2.5, Rex-1, CD105, CD117, CD133, MHC class I receptor, MHC class II receptor or other cell marker as described herein as compared to CD31− cells. Methods for performing the selection include any of the suitable assays disclosed herein. In embodiments in which larger amounts of cells are needed a more automated or semi-automated method will often be preferred such as fluorescence activated cell sorting (FACS). Selected cells desirably are able to be propagated in culture for long periods of time without becoming polyploidy or losing mulipotency.

Peripheral blood derived cells of the invention, their progenitors or their progeny, are obtained by methods known in the art, including methods for harvesting umbilical cord blood. In general, peripheral blood mononuclear cells (PBMCs) are taken from a patient using standard techniques. By "peripheral blood mononuclear cells" or "PBMCs" herein is meant lymphocytes (including T-cells, B-cells, NK cells), monocytes and stem cells. Prior to harvest, patients may be treated with agents known in the art to increase mobilization of stem cells from the bone marrow into the peripheral blood. Mobilizing agents include but are not limited to GCSF or GMCSF. In some embodiments of the invention, only PBMCs are taken, either leaving or returning red blood cells and polymorphonuclear leukocytes to the patient. This is done as is known in the art, for example using leukophoresis techniques. In general, a 5 to 7 liter leukophoresis step is done, which essentially removes PBMCs from a patient, returning the remaining blood components. Collection of the cell sample is preferably done in the presence of an anticoagulant such as heparin, as is known in the art.

Peripheral blood derived stem cells of the invention can, if needed, be purified from peripheral blood, including umbilical cord blood. Human umbilical cord blood ("cord blood") is a rich source of hematopoietic stem cells, hemangioblasts, endothelial progenitor cells, mesenchymal stem cells (MSCs). CD31+ cells are first isolated from peripheral blood or cord blood mononuclear cells by density gradient method and immuno-sorting such as MACS or FACS. Methods of isolating such cells are known in the art. Briefly, a 1 ml portion of umbilical cord is placed in a well containing RPMI and 20% FBS. The matrix cells migrate out from the cord and adhere to the plastic well. Such cells have a fibroblast morphology. The supernatant and tissue are discarded after several days in culture. The cells remaining in the well are trypsinized and transferred to a secondary culture for expansion. See, for example, Connealey et al., Proc. Natl. Acad. Sci. USA, Vol. 94, pp. 9836-9841, September 1997; and Meagher and Klingemann et al., J Hematother Stem Cell Res. 2002 June;11(3):445-8. J Hematother Stem Cell Res. 2002 June;11(3):445-8. While particular examples are directed to bone marrow-derived cells, one skilled in the art appreciates that any hematopoietic stem cell may be used in the methods of the invention.

Therefore, cells that can be used in the methods of the invention can comprise a purified sub-population of cells including, but not limited to stem cells, or any cell having the ability to give rise to endothelial cells under suitable conditions in vitro or in vivo. "Suitable conditions" are empirically determined by culturing or implanting a cell of the invention then subsequently identifying endothelial cells in the culture or implant (e.g., cells having endothelial morphology, function, or expressing one or more endothelial cell markers). Purified cells can be collected and separated, for example, by flow cytometry. Peripheral blood derived cells of the invention can be autologous (obtained from the subject) or heterologous (e.g., obtained from a donor).

Heterologous cells can be provided together with immunosuppressive therapies known in the art to prevent immune rejection of the cells.

Purified peripheral blood derived cells or their progenitors can be obtained by standard methods known in the art, including cell sorting by MACS or FACs. Isolated peripheral blood can be sorted using flow cytometers known in the art (e.g., a BD Biosciences FACScalibur cytometer) based on cell surface expression of Sca-1 (van de Rijn et al., (1989) Proc. Natl. Acad. Sci. USA 86, 4634-4638) and/or c-Kit (Okada et al., (1991) Blood 78, 1706-1712); (Okada et al., (1992) Blood 80, 3044-3050) following an initial immunomagnetic bead column-based fractionation step to obtain lineage-depleted (lin$^{31}$) cells (Spangrude et al., (1988) Science 241, 58-62); (Spangrude and Scollay, (1990) Exp. Hematol. 18, 920-926), as described (Shen et al., (2001) J. Immunol. 166, 5027-5033); (Calvi et al., (2003) Nature 425, 841-846).

For serial passage-based enrichment of peripheral blood stem cells or their progenitors in-vitro (Meirelles and Nardi, (2003) Br. J. Haematol. 123, 702-711); (Tropel et al., (2004) Exp. Cell Res. 295, 395-406), isolated peripheral blood can be plated on plastic in Dulbecco's modified Eagle's medium (Fisher Scientific, Pittsburgh, Pa.) with 10% fetal bovine serum (Hyclone, Logan, Utah), penicillin, streptomycin, L-glutamine and amphotericin-B. About forty-eight hours after the initial plating, the supernatants containing non-adherent cells can be removed and replaced with fresh culture medium after gentle washing. The cultures can then be maintained and passed once confluence is reached (e.g., for a total of about three times over the span of about 6 weeks) at which time the cultures can be terminated to collect adherent cells for analysis.

In one embodiment, a method for isolating stem cells of the invention (e.g., CD31$^+$ expressing cells) includes generation of a fraction that comprises cells expressing or having an altered level of expression (i.e., increased or decreased) of any one or more of the following markers: CD90, CD117, CD34, CD113, FLK-1, tie-2, Oct 4, GATA-4, NKx2.5, Rex-1, CD105, CD117, CD133, MHC class I receptor and MHC class II receptor as determined by standard cell marker detection assay as compared to CD31$^-$ cells. Additional selection means based on the unique profile of gene expression can be employed to further purify populations of cells capable of generating an endothelial cell. Compositions comprising an endothelial progenitor cell can be isolated and subsequently purified to an extent where they become substantially free of the biological sample from which they were obtained.

CD31$^+$ multipotent stem cells and their progenitor cells or progeny can be obtained from bone marrow or peripheral blood and then expanded in culture. Thus, the progenitor cells can be cells having an "expansion phenotype" characterized by expressing or having an altered level of expression (i.e., increased or decreased) of any one or more of the following markers: CD90, CD117, CD34, CD113, FLK-1, tie-2, Oct 4, GATA-4, NKx2.5, Rex-1, CD105, CD117, CD133, MHC class I receptor and MHC class II receptor as compared to CD31$^-$ cells. Alternatively, a differentiated endothelial cell expresses one or more characteristic endothelial cell markers that provide for its identification, such markers include, but are not limited to, VE-Cadherin, CD34, Flk-1, Tie2 and CD31, VonWillebrand Factor or factor 8.

Fractionation of CD31$^+$ Stem Cells

The invention provides for the isolation, culture, and expansion of CD31$^+$ cells. As reported herein, CD31 acts as a marker for pluripotent stem cells. There exist several methods to fractionate desired BM stem or progenitor cells for the purpose of tissue regeneration. Flow cytometry or magnetic-labeled cell sorting is one of the most popular methods. It is based on the expression of a combination of antigen markers. Markers used in flow cytometry include $CD31^+$, as described herein. Other markers known in the art include, but are not limited to, c-kit, Sca-1, CD34, Flk-1. $CD34^+$ cells or c-kit$^+$ cells exist in low numbers in BM (less than 1%), so the mobilization process, which may cause serious adverse effects (restenosis after vascular intervention and atherosclerotic plaque rupture because of the inflammatory response), is required to obtain a sufficient number of cells to be used for cell therapy.

Alternative approaches to FACS depend on one or more physiologic properties of stem cells; the side population isolation via preferential efflux of the DNA binding dye Hoechst 33342, which was originally invented for long term repopulating hematopoietic stem cell isolation in BM, based on ABC/G2 transporters, ATP binding cassette transporters expressed selectively on the surface of primitive stem or progenitor cells in a variety of sources including liver, skeletal muscle, and heart. BM-derived side population cells likely give rise to myocytes and vascular endothelium. This dye efflux technique may be affected by the technique's inherent toxicity, causing viability after Hoechst staining and labeling to be 55% and even if analyzed immediately staining, viability is only 70%~80%.

For the isolation of pure cell populations or for the expansion of isolated cells for therapeutic use, expansion is often required. Multipotent adult progenitor cells (MAPCs)[30-32] from various organ and BM-derived multipotent stem cells (BMSCs) are clonally expanded, proliferate indefinitely without obvious genetic instability and differentiate into cells of all three embryonic germ layers. Some culturing techniques are difficult, require the use of large amounts of animal serum, require multiple expensive cytokines, and often times require prolonged period to generate cell numbers that are sufficient for clinical use. Any of these methods can be used for the isolation of $CD31^+$ multipotent stem cells.

Once isolated, $CD31^+$ multipotent stem cells may be used for the prevention or treatment of virtually any disease characterized by an increase in cell death, or a decrease in cell number. In particular, the present invention provides methods of treating disease and/or disorders or symptoms thereof which comprise administering a therapeutically effective amount of a pharmaceutical composition comprising a compound of the formulae herein to a subject (e.g., a mammal such as a human). Thus, one embodiment is a method of treating a subject suffering from or susceptible to a cardiovascular disease, such as myocardial infarction, congestive heart failure, peripheral vascular obstructive disease, a peripheral neuropathy, such as diabetic, ischemic, toxic or chemical-induced neuropathies, an ischemic disease or disorder, stroke, cerebrovascular disease, liver failure, renal failure, diabetes, bone and joint diseases (osteoporosis, osteoarthritis), spinal cord injury, unhealed wound, skin gangrene or ulcer or any degenerative disease (e.g., muscular dystrophy, amyotrophic lateral sclerosis, diabetes, inflammatory bowel disease, rheumatoid arthritis, Parkinson's disease, Huntington's disease, Alzheimer' s disease).

The methods herein include administering to the subject (including a subject identified as in need of such treatment) an effective amount of a CD31 expressing multipotent stem cell described herein. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which a need for the cells of the invention may be implicated.

Endothelial Progenitor Cells

Endothelial progenitor cells exist in peripheral blood and bone marrow, and contribute to postnatal vasculogenesis, i.e., the de novo development of vessels from stem or progenitor cells. Recently, the therapeutic potential of bone marrow derived stem or progenitor cells has been widely explored in various cardiovascular diseases. Collectively, studies have demonstrated that in both animal models and early cohorts of patients, stem/progenitor cell therapy is safe and feasible, and the clinical outcomes are promising. Mechanistically, in these animal models, differentiation of endothelial progenitor cells into vasculature (vasculogenesis) has been considered as the major therapeutic mechanism. Additionally, studies have demonstrated that paracrine effects of endothelial progenitor cells can play a crucial role for mediating therapeutic effects. Endothelial progenitor cells contain abundant and multiple cytokines, such as VEGF, IGF-1 and bFGF that can function as angiogenic and neurotrophic factors. Also, endothelial progenitor cells are involved in disease pathogenesis. Decreased availability and impaired function of endothelial progenitor cells in diabetes may contribute to the development of diabetic complications including cardiomyopathy and peripheral vascular diseases, which are characterized by defective neovascularization.

Angiogenesis and vasculogenesis are responsible for the development of the vascular system in embryos. Vasculogenesis refers to the de novo development of blood vessels from endothelial progenitor cells (EPCs) or angioblasts that differentiate into endothelial cells (ECs). In contrast, angiogenesis refers to the formation of new vasculature from preexisting blood vessels through proliferation, migration, and remodeling of fully differentiated ECs. The long held belief that vasculogenesis occurs exclusively during development and that in the adult, new vessels are formed solely by angiogenesis, was dismantled by the finding that circulating EPCs, isolated from adult species, could differentiate along an EC lineage in vitro, providing evidence for the existence of postnatal vasculogenesis. Initially, Flk-1 and CD34, shared by angioblasts and hematopoietic cells were used to isolate putative angioblasts from the mononuclear cell fraction of the peripheral blood (Asahara et al., *Science*. 1997;275:964-967). Meanwhile, EPCs subsequently were isolated from umbilical cord blood, bone marrow (BM), and $CD34^+$ or $CD133^+$ hematopoietic stem cells (Asahara et al., *Circ Res*. Aug. 6, 1999;85(3):221-228; Murohara et al., *Journal of Clinical Investigation*. 2000;105:1527-1536; Shi et al., *Blood*. 1998;92:362-367; Rafii et al., *Journal of Clinical Investigation*. 2000;105:17-19). These cells differentiate into endothelial cells, as shown by expression of various endothelial proteins (KDR, von Willebrand factor, endothelial nitric oxidase synthase (eNOS), VE-cadherin, CD146), uptake of DiI-acetylated low-density lipoprotein (DiI-acLDL) and binding of lectin. In animal models of ischemia, heterologous, homologous, and autologous EPCs have been shown to incorporate into sites of active neovascularization in ischemic tissue (Shi et al., *Blood.* 1998;92: 362-367 Asahara et al., *EMBO J.* 1999; 18 :3964-3972Hatzopoul os et al., *Development.* 1998;125(8):1457-1468; Niklason et al., *Science.* 1999;286:1493-1494; Rekhter et al., *Circulation Research.* 1998;83:705-713; Gerber et al., *Development.* 1999;126:1149-1159; Gunsilius et al., *Lancet.* 2000;355:1688-1691)

As reported in more detail below, therapeutic intervention by transplantation of $CD31^+$ cells (or their progenitors or progeny) reversed or attenuated ischemic injury (e.g., hind limb ischemia and myocardial infarction) by contributing to the vasculature of the damaged tissue.

Endothelial Cell Promoting Conditions

Once isolated, a $CD31^+$ stem cell useful in the methods of the invention may be maintained indefinitely in culture. In one approach, isolated $CD31^+$ stem cells are used with or without expansion in vitro to increase the number of cells suitable for therapeutic administration (e.g., cells having hemangioblastic activity or having the potential to differentiate into an endothelial cell). Alternatively or subsequently, a $CD31^+$ cell of the invention is incubated under conditions that promote endothelial cell differentiation. Examples of endothelial cell promoting conditions are known in the art. See, for example, U.S. Pat. No. 5,980,887; PCT/US99/ 05130 (WO 99/45775) and references cited therein, herein incorporated by reference. In one embodiment, the stem cells of the invention are contacted with any one or more of the following factors that promote or support cardiomyogenic, neural or endothelial growth, proliferation, or cell differentiation: acidic and basic fibroblast growth factors (aFGF (GenBank Accession No. NP_149127) and bFGF (GenBank Accession No. AAA52448)), vascular endothelial growth factor (VEGF-1, (GenBank Accession No. AAA35789 or NP_001020539)), VEGF-2, VEGF165, epidermal growth factor (EGF)(GenBank Accession No. NP_001954)), transforming growth factor α and β (TGF-α (GenBank Accession No. NP_003227) and TFG-β (GenBank Accession No. 1109243A)), platelet-derived endothelial cell growth factor (PD-ECGF) (GenBank Accession No. NP_001944)), platelet-derived growth factor (PDGF) (GenBank Accession No. 1109245A), tumor necrosis factor α (TNF-α) (GenBank Accession No. CAA26669), hepatocyte growth factor (HGF) (GenBank Accession No. BAA14348), insulin like growth factor (IGF) (GenBank Accession No. P08833), erythropoietin (GenBank Accession No. P01588), colony stimulating factor (CSF), macrophage-CSF (M-CSF) (GenBank Accession No. AAB59527), Sonic hedgehog (SHh, GenBank Accession No. NP_000184), granulocyte/macrophage CSF (GM-CSF (GenBank Accession No. NP_000749)), angiopoetin-1 (Ang1 (GenBank Accession No. NP_001137)), angiopoietin-2 (Ang-2, GenBank Accession No. NP_001138), stromal cell derived factor (GenBank Accession No. NP_008854), hypoxia inducible factor (HIF-1 (GenBank Accession No. NP_001521), thrombopoietin, and interleukin 2, interleukin 6, stem cell factor (SCF), FLT3, and nitric oxide synthase (NOS) (GenBank Accession No. AAA36365); and functional fragments thereof. See, also Klagsbrun, et al., *Annu. Rev. Physiol.*, 53:217-239 (1991); Folkman, et al., *J. Biol. Chem.*, 267:10931-10934 (1992) and Symes, et al., *Current Opinion in Lipidology*, 5:305-312 (1994). Muteins or fragments of such factors may be used as long as they induce or promote formation of endothelial cells. In one embodiment, an endothelial cell promoting condition includes contact with VEGF, particularly VEGF-1, VEGF-2, and or VEGF 165. Additionally preferred endothelial cell promoting conditions include contact with certain cell matrix proteins, such as fibronectin. Preferred angiogenic factors and mitogens (and methods of use) are disclosed herein as well as U.S. Pat. No. 5,980,887 and WO 99/45775.

Endothelial cells can be contacted with such angiogenic factors or mitogens prior to, during or following transplantation. Methods for making and using EPCs have been disclosed. See U.S. Pat. No. 5,980,887, for example. Typical methods can include isolating the EPCs from the mammal and contacting the EPCs with at least one angiogenic factor and/or mitogen ex vivo.

Administration

Compositions comprising a $CD31^+$ cell having the potential to differentiate into an endothelial cell (e.g., $CD31^+$ multipotent stem cells or progenitors or progeny thereof) can be provided systemically or locally for the treatment of a disease characterized by cell death or loss. In one embodiment, a $CD31^+$ cell of the invention is provided locally to a neural tissue (e.g., a sensory or motor neuron) for the treatment of neuropathy. Alternatively, compositions comprising a $CD31^+$ expressing cell having hemangioblastic activity or having the potential to differentiate into an endothelial cell (e.g., multipotent stem cells, endothelial progenitor cells, mesenchymal stem cells, mononuclear cells, or progenitors or progeny thereof) can be provided indirectly to the neural tissue of interest, for example, by local administration into a muscle comprising the neuron or into the circulatory system supplying the neuron. Following transplantation or implantation, the cells may engraft and differentiate into endothelial cells. "Engraft" refers to the process of cellular contact and incorporation into an existing tissue of interest in vivo. Expansion and differentiation agents can be provided prior to, during or after administration to increase production of endothelial cells in vivo.

Compositions of the invention include pharmaceutical compositions comprising a $CD31^+$ expressing cell having hemangioblastic activity, including having the potential to differentiate into a hematopoietic cell or an endothelial cell (e.g., multipotent stem cells, endothelial progenitor cells, mesenchymal stem cells, mononuclear cells, or progenitors or progeny thereof) and a pharmaceutically acceptable carrier. Administration can be autologous or heterologous. For example, a $CD31^+$ expressing cell having the potential to differentiate into an endothelial cell can be obtained from one subject, and administered to the same subject or a different, compatible subj ect.

A $CD31^+$ cell of the invention can be administered via localized injection, including catheter administration, systemic injection, localized injection, intravenous injection, intramuscular injection, intraneural injection or parenteral administration. When administering a therapeutic composition of the present invention (e.g., a pharmaceutical composition), it will generally be formulated in a unit dosage injectable form (solution, suspension, emulsion).

Compositions of the invention can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the cells utilized in practicing the present invention in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the multipotent stem cells, endothelial progenitor cells, mesenchymal stem cells, mononuclear cells, or progenitors or progeny thereof.

The compositions can be isotonic, i.e., they can have the same osmotic pressure as blood and lacrimal fluid. The desired isotonicity of the compositions of this invention may be accomplished using sodium chloride, or other pharmaceutically acceptable agents, such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

A method to potentially increase cell survival when introducing the cells into a subject in need thereof is to incorporate $CD31^+$ expressing multipotent stem cells and their progenitor cells or their progeny (e.g., in vivo, ex vivo or in vitro derived) of interest into a biopolymer or synthetic polymer. Depending on the subject's condition, the site of injection might prove inhospitable for cell seeding and growth because of scarring or other impediments. Examples of biopolymer include, but are not limited to, cells mixed with fibronectin, fibrin, fibrinogen, thrombin, collagen, proteoglycans and other protein components of the extracellular matrix. This could be constructed with or without included expansion factors, differentiation factors, endothelial cell promoting factors, neurotrophic factors, or angiogenic factors. Additionally, these could be in suspension, but residence time at sites subjected to flow would be nominal. Another alternative is a three-dimensional gel with cells entrapped within the interstices of the cell biopolymer admixture. Again, expansion or differentiation factors could be included with the cells. These could be deployed by injection via various routes described herein.

Those skilled in the art will recognize that the components of the compositions should be selected to be chemically inert and will not affect the viability or efficacy of the cells having the potential to differentiate into an endothelial cell. This will present no problem to those skilled in chemical and pharmaceutical principles, or problems can be readily avoided by reference to standard texts or by simple experiments (not involving undue experimentation), from this disclosure and the documents cited herein. Additionally, these could be in suspension, but residence time at sites subjected to flow would be nominal. Another alternative is a three-dimensional gel with cells entrapped within the interstices of the cell biopolymer admixture. Again, expansion or differentiation factors could be included with the cells. These could be deployed by injection via various routes described herein.

$CD31^+$ expressing multipotent stem cells can be cultured, treated with agents and/or administered in the presence of polymer scaffolds. Polymer scaffolds are designed to optimize gas, nutrient, and waste exchange by diffusion. Polymer scaffolds can comprise, for example, a porous, nonwoven array of fibers. The polymer scaffold can be shaped to maximize surface area, to allow adequate diffusion of nutrients and growth factors to the cells. Taking these parameters into consideration, one of skill in the art could configure a polymer scaffold having sufficient surface area for the cells to be nourished by diffusion until new blood vessels interdigitate the implanted engineered-tissue using methods known in the art. Polymer scaffolds can comprise a fibrillar structure. The fibers can be round, scalloped, flattened, star-shaped, solitary or entwined with other fibers. Branching fibers can be used, increasing surface area proportionately to volume.

Unless otherwise specified, the term "polymer" includes polymers and monomers that can be polymerized or adhered to form an integral unit. The polymer can be non-biodegradable or biodegradable, typically via hydrolysis or enzymatic cleavage. The term "biodegradable" refers to materials that are bioresorbable and/or degrade and/or break down by mechanical degradation upon interaction with a physiological environment into components that are metabolizable or excretable, over a period of time from minutes to three years, preferably less than one year, while maintaining the requisite structural integrity. As used in reference to polymers, the term "degrade" refers to cleavage of the polymer chain, such that the molecular weight stays approximately constant at the oligomer level and particles of polymer remain following degradation.

Materials suitable for polymer scaffold fabrication include polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyester polyacrylates, polymethacrylate, acyl substituted cellulose acetates, non-degradable polyurethanes, polystyrenes, polyvinyl chloride, polyvinyl flouride, polyvinyl imidazole, chlorosulphonated polyolifins, polyethylene oxide, polyvinyl alcohol, teflon RTM, nylon silicon, and shape memory materials, such as poly(styrene-block-butadiene), polynorbornene, hydrogels, metallic alloys, and oligo(c-caprolactone)diol as switching segment/oligo(p-dioxyanone)diol as physical crosslink. Other suitable polymers can be obtained by reference to The Polymer Handbook, 3rd edition (Wiley, N.Y., 1989).

Factors, including but not limited to nutrients, growth factors, inducers of differentiation or de-differentiation, products of secretion, immunomodulators, cytokines, neurotrophic factors, myogenic factors, angiogenic factors, inhibitors of inflammation, regression factors, hormones, various tissue extracts (e.g. from myocardium or skeletal muscle) or other biologically active compounds can be incorporated into or can be provided in conjunction with the polymer scaffold.

Those skilled in the art will recognize that the components of the compositions should be selected to be chemically inert and will not affect the viability or efficacy of the multipotent stem cells, endothelial progenitor cells, mesenchymal stem cells, and their progenitor cells as described in the present invention.

One consideration concerning the therapeutic use of multipotent stem cells, hematopoietic stem cells, endothelial progenitor cells, mesenchymal stem cells, and their progenitor cells of the invention is the quantity of cells necessary to achieve an optimal effect. In current human studies of autologous mononuclear peripheral blood cells, empirical doses ranging from 1 to $4\times10^7$ cells have been used with encouraging results. The methods of the invention may require optimization of the amount of cells injected into a tissue of interest. Thus, the quantity of cells to be administered will vary depending on the neural tissue or the subject being treated. In one embodiment, between $10^4$ to $10^8$, $10^6$ to $10^8$, or $10^5$ to $10^9$ cells are implanted. In other embodiments, $10^5$ to $10^7$ cells are implanted. In still other embodiments, $3\times10^7$ stem cells of the invention can be administered to a human subject. The precise determination of an effective dose may be based on factors individual to each patient, including their size, age, sex, weight, and condition. Therefore, dosages are determined empirically using no more than routine by those skilled in the art from this disclosure and the knowledge in the art.

CD31$^+$ expressing multipotent stem cells and progenitor cells of the invention can comprise a purified population of CD31$^+$ expressing stem cells having hemangioblastic activity or having the potential to differentiate into an endothelial cell and other lineages. Those skilled in the art can readily determine the percentage of such cells in a population using various well-known methods, such as fluorescence activated cell sorting (FACS). Desirable ranges of purity in mixed populations comprising multipotent stem cells, endothelial progenitor cells, mesenchymal stem cells, or progenitor cells of the invention cells are about 50 to about 55%, about 55 to about 60%, and about 65 to about 70%. More desirably, the purity is about 70 to about 75%, about 75 to about 80%, about 80 to about 85%; and still more desirably the purity is about 85 to about 90%, about 90 to about 95%, and about 95 to about 100%. Purity of CD31$^+$ expressing multipotent stem cells can be determined according to the marker profile within a population. Dosages can be readily adjusted by those skilled in the art (e.g., a decrease in purity may require an increase in dosage).

The skilled artisan can readily determine the amount of cells and optional additives, vehicles, and/or carrier in compositions and to be administered in methods of the invention. Typically, any additives (in addition to the active stem cell(s) and/or agent(s)) are present in an amount of 0.001 to 50% (weight) solution in phosphate buffered saline, and the active ingredient is present in the order of micrograms to milligrams, such as about 0.0001 to about 5 wt %, preferably about 0.0001 to about 1 wt %, still more preferably about 0.0001 to about 0.05 wt % or about 0.001 to about 20 wt %, preferably about 0.01 to about 10 wt %, and still more preferably about 0.05 to about 5 wt %. Of course, for any composition to be administered to an animal or human, and for any particular method of administration, it is preferred to determine therefore: toxicity, such as by determining the lethal dose (LD) and LD$_{50}$ in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

The number of CD31$^+$ expressing multipotent stem cells of the invention can be increased by increasing the survival or proliferation of existing stem cells, or their progenitor cells.

Agents (e.g., expansion agents) which increase proliferation or survival of a CD31$^+$ expressing cell or progenitors or progeny thereof are useful according to the invention. Agents comprising growth factors are known in the art to increase proliferation or survival of stem cells. For example, U.S. Pat. Nos. 5,750,376 and 5,851,832 describe methods for the in vitro culture and proliferation of stem cells using TGF. An active role in the expansion and proliferation of stem cells has also been described for BMPs (Zhu, G. et al, (1999) Dev. Biol. 215: 118-29 and Kawase, E. et al, (2001) Development 131: 1365) and Wnt proteins (Pazianos, G. et al, (2003) Biotechniques 35: 1240 and Constantinescu, S. (2003) J. Cell Mol. Med. 7: 103). U.S. Pat. Nos. 5,453,357 and 5,851,832 describe proliferative stem cell culture systems that utilize FGFs. The contents of each of these references are specifically incorporated herein by reference for their description of expansion agents known in the art.

Agents comprising growth factors are also known in the art to increase mobilization of stem cells from the bone marrow into the peripheral blood. Mobilizing agents include but are not limited to GCSF or GMCSF. An agent that increases mobilization of stem cells into the blood can be provided before peripheral blood harvest or alternatively, to augment or supplement other methods of the invention where it would be desirable to increase circulating levels of stem cells (e.g., to increase targeting of the cells to the neural tissue).

Agents comprising cell-signaling molecules are also known in the art to increase proliferation or survival of stem cells. For example, U.S. Patent Application No. 20030113913 describes the use of retinoic acid in stem cell self renewal in culture. The contents of each of these references are specifically incorporated herein by reference for their description of expansion agents known in the art.

Agents comprising pharmacological or pharmaceutical compounds are also known in the art to increase production or survival of stem cells.

Agents comprising signaling molecules are also known to induce differentiation of endothelial cells. The contents of each of these references are specifically incorporated herein by reference for their description of differentiation agents known in the art.

Agents comprising pharmacological or pharmaceutical compounds are also known in the art to induce differentiation of stem cells.

Agents can be provided directly to an ischemic tissue or to a neural tissue effected by a neuropathy (e.g., motor neuron, sensory neuron). Alternatively, agents can be provided indirectly to the neural tissue of interest, for example, by local administration into the circulatory system or into the muscle that comprises the neural tissue.

Agents can be administered to subjects in need thereof by a variety of administration routes. Methods of administration, generally speaking, may be practiced using any mode of administration that is medically acceptable, meaning any mode that produces effective levels of the active compounds without causing clinically unacceptable adverse effects. Such modes of administration include oral, rectal, topical, intraocular, buccal, intracisternal, intracerebroventricular, intratracheal, nasal, transdermal, within/on implants, e.g., fibers such as collagen, osmotic pumps, or grafts comprising appropriately transformed cells, etc., or parenteral routes. The term "parenteral" includes subcutaneous, intravenous, intramuscular, intraperitoneal, or infusion. Intravenous or intramuscular routes are not particularly suitable for long-term therapy and prophylaxis. A particular method of administration involves coating, embedding or derivatizing fibers, such as collagen fibers, protein polymers, etc. with therapeutic proteins. Other useful approaches are described in Otto, D. et al., J. Neurosci. Res. 22: 83 and in Otto, D. and Unsicker, K. J. Neurosci. 10: 1912.

In vitro and ex vivo applications can involve culture of the multipotent stem cells, endothelial progenitor cells, mesenchymal stem cells, and progenitor cells with the selected agent to achieve the desired result. For example, cultures of cells (from the same individual and from different individuals) can be treated with expansion agents to increase the number of cells of interest. Alternatively, the cultures are treated with differentiation agents of interest to stimulate the production of cells having the desired characteristics. Cells produced by these methods can then be used for a variety of therapeutic applications (e.g., localized implantation).

Multipotent stem cells, endothelial progenitor cells, mesenchymal stem cells, and progenitor cells derived from cultures of the invention can be implanted into a host. The transplantation can be autologous, such that the donor of the stem cells is also the recipient of the stem cells. The transplantation can be heterologous, such that the donor of the stem cells is not the recipient of the stem cells. In one embodiment, once transferred into a host, the cells engraft in the microvasculature of the host neural tissue.

Agents of the invention may be supplied along with additional reagents in a kit. The kits can include instructions for the treatment regime or assay, reagents, equipment (test tubes, reaction vessels, needles, syringes, etc.) and standards for calibrating or conducting the treatment or assay. The instructions provided in a kit according to the invention may be directed to suitable operational parameters in the form of a label or a separate insert. Optionally, the kit may further comprise a standard or control information so that the test sample can be compared with the control information standard to determine whether a consistent result is achieved.

Genetically Modified Stem Cells

Prior to administration, $CD31^+$ multipotent stem cells, their progenitors or their progeny, described herein can optionally be genetically modified, in vitro, in vivo or ex vivo, by introducing heterologous DNA or RNA or protein into the cell by a variety of recombinant methods known to those of skill in the art. These methods are generally grouped into four major categories: (1) viral transfer, including the use of DNA or RNA viral vectors, such as retroviruses (including lentiviruses), Simian virus 40 (SV40), adeno-associated virus, adenovirus, Sindbis virus, and bovine papillomavirus, for example; (2) chemical transfer, including calcium phosphate transfection and DEAE dextran transfection methods; (3) membrane fusion transfer, using DNA-loaded membranous vesicles such as liposomes, red blood cell ghosts, and protoplasts, for example; and (4) physical transfer techniques, such as microinjection, electroporation, or direct "naked" DNA transfer.

The $CD31^+$ stem cells of the invention, their progenitors or their progeny, can be genetically altered by insertion of pre-selected isolated DNA, by substitution of a segment of the cellular genome with pre-selected isolated DNA, or by deletion of or inactivation of at least a portion of the cellular genome of the cell. Deletion or inactivation of at least a portion of the cellular genome can be accomplished by a variety of means, including but not limited to genetic recombination, by antisense technology (which can include the use of peptide nucleic acids, or PNAs), or by ribozyme technology, for example. The altered genome may contain the genetic sequence of a selectable or screenable marker gene that is expressed so that the cell with altered genome, or its progeny, can be differentiated from cells having an unaltered genome. For example, the marker may be a green, red, yellow fluorescent protein, β-galactosidase, the neomycin resistance gene, a genetically altered stem cell, or its progeny, may contain DNA encoding a therapeutic protein (e.g., a protein that increases angiogenesis, increases endothelial cell or Schwann cell proliferation, or decreases apoptosis) under the control of a promoter that directs strong expression of the recombinant protein. Alternatively, the cell may express a gene that can be regulated by an inducible promoter or other control mechanism where conditions necessitate highly controlled regulation or timing of the expression of a protein, enzyme, or other cell product. Such $CD31^+$ stem cells, when transplanted into a subject suffering from a disease, for example, including but not limited to myocardial infarction, congestive heart failure, peripheral vascular obstructive disease, ischemia, limb ischemia, stroke, transient ischemia, reperfusion injury, peripheral neuropathy, diabetic neuropathy, toxic neuropathy, diabetic dementia, or autonomic neuropathy, spinal cord injury, leukemia, lymphoma, myelodysplastic syndrome, pancytopenia, anemia, thrombocytopenia, leukopenia, liver failure, renal failure, diabetes, rheumatoid arthritis, osteoarthritis, skin wound, diabetic foot or ulcer, gangrene, diabetic wound and osteoporosis, confer a therapeutic benefit.

Proteins expressed in genetically modified cells include any protein capable of supporting or enhancing tissue repair, tissue regeneration, neural function or angiogenesis. Such proteins include angiogenic cytokines and neurotrophic factors. In one embodiment, the $CD31^+$ stem cell of the invention, its progenitor or its progeny, express heterologous DNA encoding a polypeptide or fragment thereof that encodes a therapeutic polypeptide (e.g., acidic and basic fibroblast growth factors, vascular endothelial growth factor, VEGF-2, VEGF 165, epidermal growth factor, transforming growth factor α and β, platelet-derived endothelial growth factor, platelet-derived growth factor A, B, E, tumor necrosis factor α, hepatocyte growth factor, insulin like growth factor 1, and 2, erythropoietin, colony stimulating factor, macrophage-CSF, Sonic hedgehog, granulocyte/macrophage CSF, angiopoetin-1, angiopoietin-2, stromal cell derived factor (SDF-1) Hypoxia inducible factor (HIF-1) and nitric oxide synthase). Insertion of one or more pre-selected DNA sequences can be accomplished by homologous recombination or by viral integration into the host cell genome. The desired gene sequence can also be incorporated into the cell, particularly into its nucleus, using a plasmid expression vector and a nuclear localization sequence. Methods for directing polynucleotides to the nucleus have been described in the art. Calcium phosphate transfection can be used to introduce plasmid DNA containing a target gene or polynucleotide into isolated or cultured stem cells or their progenitors and is a standard method of DNA transfer to those of skill in the art. DEAE-dextran transfection, which is also known to those of skill in the art, may be preferred over calcium phosphate transfection where transient transfection is desired, as it is often more efficient. Since the cells of the present invention are isolated cells, microinjection can be particularly effective for transferring genetic material into the cells. This method is advantageous because it provides delivery of the desired genetic material directly to the nucleus, avoiding both cytoplasmic and lysosomal degradation of the injected polynucleotide. This technique has been used effectively to accomplish peripheral blood derived modification in transgenic animals. Cells of the present invention can also be genetically modified using electroporation.

Liposomal delivery of DNA or RNA to genetically modify the cells can be performed using cationic liposomes, which form a stable complex with the polynucleotide. For stabilization of the liposome complex, dioleoyl phosphatidylethanolamine (DOPE) or dioleoyl phosphatidylcholine (DOPA) can be added. Commercially available reagents for liposomal transfer include Lipofectin (Life Technologies). Lipofectin, for example, is a mixture of the cationic lipid N-[1-(2,3-dioleyloxy)propyl]-N-N-N-trimethyl ammonia chloride and DOPE. Liposomes can carry larger pieces of DNA, can generally protect the polynucleotide from degradation, and can be targeted to specific cells or tissues. Cationic lipid- mediated gene transfer efficiency can be enhanced by incorporating purified viral or cellular envelope components, such as the purified G glycoprotein of the vesicular stomatitis virus envelope (VSV-G). Gene transfer techniques which have been shown effective for delivery of DNA into primary and established mammalian cell lines using lipopolyamine-coated DNA can be used to introduce target DNA into the stem cells described herein.

Naked plasmid DNA can be injected directly into a tissue mass formed of cells from the isolated peripheral blood or their progenitors. This technique has been shown to be effective in transferring plasmid DNA to skeletal muscle tissue, where expression in mouse skeletal muscle has been observed for more than 19 months following a single intramuscular injection. More rapidly dividing cells take up naked plasmid DNA more efficiently. Therefore, it is advantageous to stimulate cell division prior to treatment with plasmid DNA. Microprojectile gene transfer can also be used to transfer genes into stem cells either in vitro or in vivo. The basic procedure for microprojectile gene transfer was described by J. Wolff in Gene Therapeutics (1994), page 195. Similarly, microparticle injection techniques have been described previously, and methods are known to those of skill in the art. Signal peptides can be also attached to plasmid DNA to direct the DNA to the nucleus for more efficient expression.

Viral vectors are used to genetically alter stem cells of the present invention and their progeny. Viral vectors are used, as are the physical methods previously described, to deliver one or more target genes, polynucleotides, antisense molecules, or ribozyme sequences, for example, into the cells. Viral vectors and methods for using them to deliver DNA to cells are well known to those of skill in the art. Examples of viral vectors that can be used to genetically alter the cells of the present invention include, but are not limited to, adenoviral vectors, adeno-associated viral vectors, retroviral vectors (including lentiviral vectors), alphaviral vectors (e. g., Sindbis vectors), and herpes virus vectors.

Screening Assays

The invention provides methods for identifying modulators, i.e., candidate or test compounds or agents (e.g., proteins, peptides, peptidomimetics, peptoids, polynucleotides, small molecules or other drugs) that are useful for the treatment of neuropathy. Agents thus identified can be used to increase, for example, proliferation, survival, engraftment, or differentiation of a stem cell or its progenitor e.g., in a therapeutic protocol. In one embodiment, the agent modulates a cell of the invention thereby enhancing angiogenesis in a neural tissue of interest.

The test agents of the present invention can be obtained singly or using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. (1994) et al., J. Med. Chem. 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al (1994) Angew. Chem. Int. Ed. Engl. 33:2061; and Gallop et al. (1994) J. Med. Chem. 37:1233.

Libraries of compounds may be presented in solution (e.g., Houghten (1992), Biotechniques 13:412-421), or on beads (Lam (1991), Nature 354:82-84), chips (Fodor (1993) Nature 364:555-556), bacteria (Ladner, U.S. Patent No. 5,223,409), spores (Ladner U.S. Pat. No. 5,223,409), plasmids (Cull et al. (1992) Proc Natl Acad Sci USA 89:1865-1869) or on phage (Scott and Smith (1990) Science 249: 386-390; Devlin (1990) Science 249:404-406; Cwirla et al. (1990) Proc. Natl. Acad. Sci. 87:6378-6382; Felici (1991) J. Mol. Biol. 222:301-310; Ladner supra.).

Chemical compounds to be used as test agents (i.e., potential inhibitor, antagonist, agonist) can be obtained from commercial sources or can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock (1989) Comprehensive Organic Transformations, VCH Publishers; T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Combinations of substituents and variables in compounds envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., transport, storage, assaying, therapeutic administration to a subject).

The compounds described herein can contain one or more asymmetric centers and thus occur as racemates and racemic mixtures, single enantiomers, individual diastereomers and diastereomeric mixtures. All such isomeric forms of these compounds are expressly included in the present invention. The compounds described herein can also be represented in multiple tautomeric forms, all of which are included herein. The compounds can also occur in cis-or trans- or E-or Z-double bond isomeric forms. All such isomeric forms of such compounds are expressly included in the present invention.

Test agents of the invention can also be peptides (e.g., growth factors, cytokines, receptor ligands) or polynucleotides encoding such peptides.

Screening methods of the invention identify agents that enhance or inhibit a biological activity of a cell of the invention. In one embodiment, a cell of the invention (e.g., multipotent stem cell, endothelial progenitor cell, mesenchymal stem cell, or other progenitor cell) is contacted with the agent prior to implantation in a host. In another embodiment, an agent is administered in combination with a cell of the invention. Desirably, the agent increases angiogenesis in a neural tissue of interest, increases Schwann cell proliferation, increases endothelial cell proliferation, increases neural conductance, increases pain responsiveness, decreases apoptosis, or is otherwise useful for the treatment of a diabetic neuropathy.

In one embodiment, a $CD31^+$ cells of the invention is contacted with the agent in vitro prior to implantation in a host. The treated cell is then locally delivered to a tissue of interest. The biological function or vascularity of the tissue is compared between a host that received the treated cell relative to a host that received an untreated control cell. An increase in the biological function or vascularity of the tissue that received the treated cell identifies the agent as useful in the methods of the invention.

In another embodiment, an agent is locally administered to a tissue of interest in combination (e.g., prior to, during, or following) implantation of a cell of the invention. The biological function or vascularity of the tissue contacted with the agent is compared to the biological function of in a control host that did not receive the agent. An increase in the biological function or vascularity of the tissue contacted with the combination identifies the agent as useful in the methods of the invention.

In practicing the methods of the invention, it may be desirable to employ a purified population of $CD31^+$ multipotent stem cells, endothelial progenitor cells, mesenchymal stem cells, and progenitor cells. A purified population of multipotent stem cells, endothelial progenitor cells, mesenchymal stem cells, and progenitor cells has about 50-55%, 55-60%, 60-65% and 65-70% purity. In other embodiments, the purity is about 70-75%, 75-80%, 80-85%; and in still other embodiments the purity is about 85-90%, 90-95%, and 95-100%.

Agents useful in the methods of the invention can also be detected by identifying an increase in expression of a cytokine or other desirable marker. The level of expression can be measured in a number of ways, including, but not limited to: measuring the mRNA encoded by the genetic markers; measuring the amount of protein encoded by the genetic markers; or measuring the activity of the protein encoded by the genetic markers.

The level of mRNA corresponding to a marker can be determined both by in situ and by in vitro formats. The isolated mRNA can be used in hybridization or amplification assays that include, but are not limited to, Southern or Northern analyses, polymerase chain reaction analyses and probe arrays. In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the markers described herein.

The level of mRNA in a sample can be evaluated with nucleic acid amplification, e.g., by rtPCR (Mullis (1987) U.S. Pat. No. 4,683,202), ligase chain reaction (Barany (1991) Proc. Natl. Acad. Sci. USA 88:189-193), self sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the marker being analyzed.

Assays for Angiogenesis, Proliferation, and Apoptosis

The invention provides methods for increasing angiogenesis in a tissue of interest, increasing endothelial cell proliferation, decreasing apoptosis, or is otherwise useful for the treatment of a diabetic neuropathy. Methods for measuring an increase in angiogenesis are also known in the art and are described herein. In general, angiogenesis can be assayed by measuring the number of non-branching blood vessel segments (number of segments per unit area), the functional vascular density (total length of perfused blood vessel per unit area), the vessel diameter, or the vessel volume density (total of calculated blood vessel volume based on length and diameter of each segment per unit area). Angiogenesis can also be quantitated using endothelial cell markers. For example, angiogenesis can be assayed in a cardiac, skeletal or neural tissue using immunohistochemical staining with antibodies prepared against a specific endothelial cell marker isolectin B4 (Vector Laboratories). Capillary density is evaluated morphometrically by histological examination of randomly selected fields of tissue sections. Capillaries are recognized as tubular structures positive for isolectin. Such methods are described, for example, by Iwakura et al., Circulation 2003; 108: 3115-21.

Methods of assaying cell growth and proliferation are known in the art. See, for example, Kittler et al. (Nature. 432 (7020):1036-40, 2004) and Miyamoto et al. (Nature 416 (6883):865-9, 2002). Assays for cell proliferation generally involve the measurement of DNA synthesis during cell replication. In one embodiment, DNA synthesis is detected using labeled DNA precursors, such as ([$^3$H]-Thymidine or 5-bromo-2*-deoxyuridine [BrdU], which are added to cells (or animals) and then the incorporation of these precursors into genomic DNA during the S phase of the cell cycle (replication) is detected (Ruefli-Brasse et al., Science 302 (5650):1581-4, 2003; Gu et al., Science 302 (5644):445-9, 2003).

Assays for measuring cell survival are known in the art, and are described, for example, by Crouch et al. (J. Immunol. Meth. 160, 81-8); Kangas et al. (Med. Biol. 62, 338-43, 1984); Lundin et al., (Meth. Enzymol. 133, 27-42, 1986); Petty et al. (Comparison of J. Biolum. Chemilum. 10, 29-34, 1995); and Cree et al. (AntiCancer Drugs 6: 398-404, 1995). Cell viability can be assayed using a variety of methods, including MTT (3-(4,5-dimethylthiazolyl)-2,5-diphenyltetrazolium bromide) (Barltrop, Bioorg. & Med. Chem. Lett.1: 611, 1991; Cory et al., Cancer Comm. 3, 207-12, 1991; Paull J. Heterocyclic Chem. 25, 911, 1988). Assays for cell viability are also available commercially. These assays include but are not limited to CELLTITER-GLO® Luminescent Cell Viability Assay (Promega), which uses luciferase technology to detect ATP and quantify the health or number of cells in culture, and the CellTiter-Glo® Luminescent Cell Viability Assay, which is a lactate dehyrodgenase (LDH) cytotoxicity assay (Promega).

Kits

The invention provides kits for the treatment or prevention of ischemia, related tissue damage, or any other disease characterized by increased cell death or reduced cell number. In one embodiment, the kit includes a therapeutic or prophylactic composition containing an effective amount of CD31$^+$ cells in unit dosage form. In some embodiments, the kit comprises a sterile container which contains a therapeutic or prophylactic vaccine; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired CD31$^+$ cells of the invention are provided together with instructions for administering it to a subject having or at risk of developing ischemia, related tissue damage, or any other disease characterized by increased cell death or reduced cell number. The instructions will generally include information about the use of the composition for the treatment or prevention of ischemia or for enhancing angiogenesis to a tissue in need thereof. In other embodiments, the instructions include at least one of the following: description of the expression vector; dosage schedule and administration for treatment or prevention of ischemia or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

Combination Therapies

Compositions and methods of the invention may be used in combination with any conventional therapy for ischemia, related tissue damage, or any other disease characterized by increased cell death or reduced cell number known in the art or in combination with any therapy known to increase angiogenesis. In one embodiment, a CD31$^+$ multipotent stem cell may be used in combination with any pro-angiogenic therapy known in the art.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

CD31 is a Common Marker for Various Stem Cells

Figure 1I:
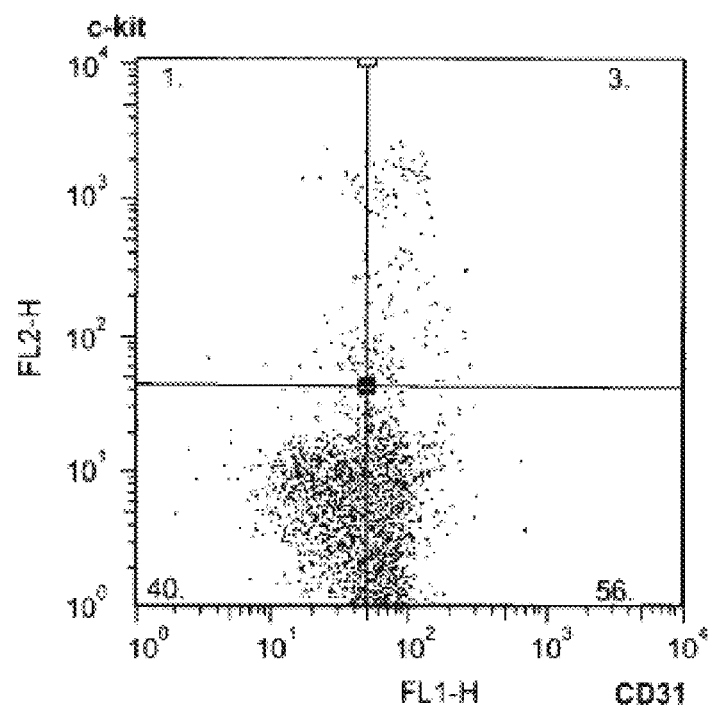
FIG. 1I shows c-kit.
Figure 1J:
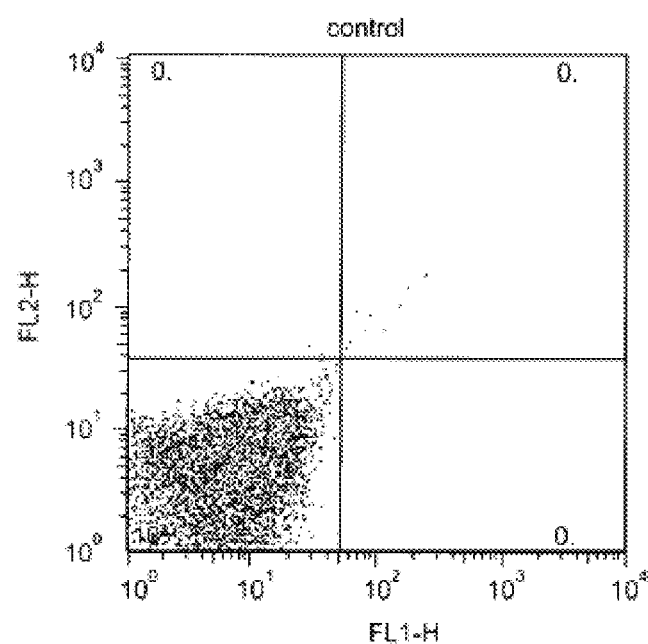
FIG. 1J shows a control.
Figure 1K:
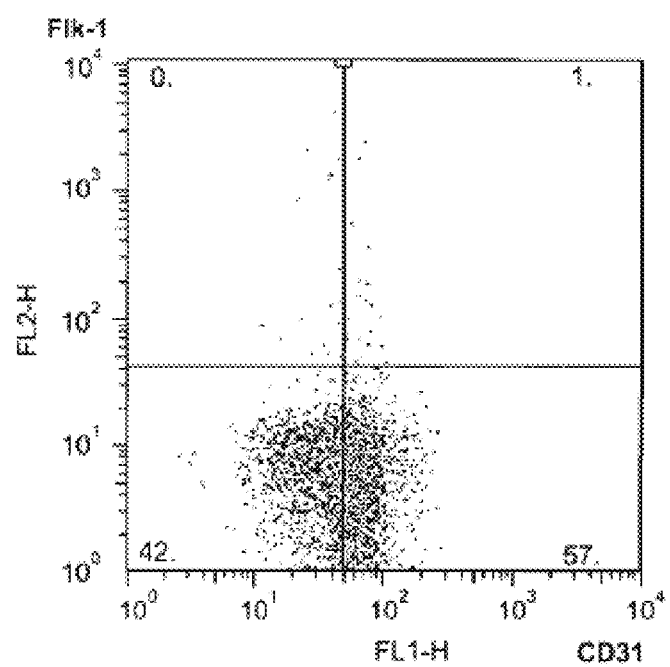
FIG. 1K shows Flk-1.
Figure 2:
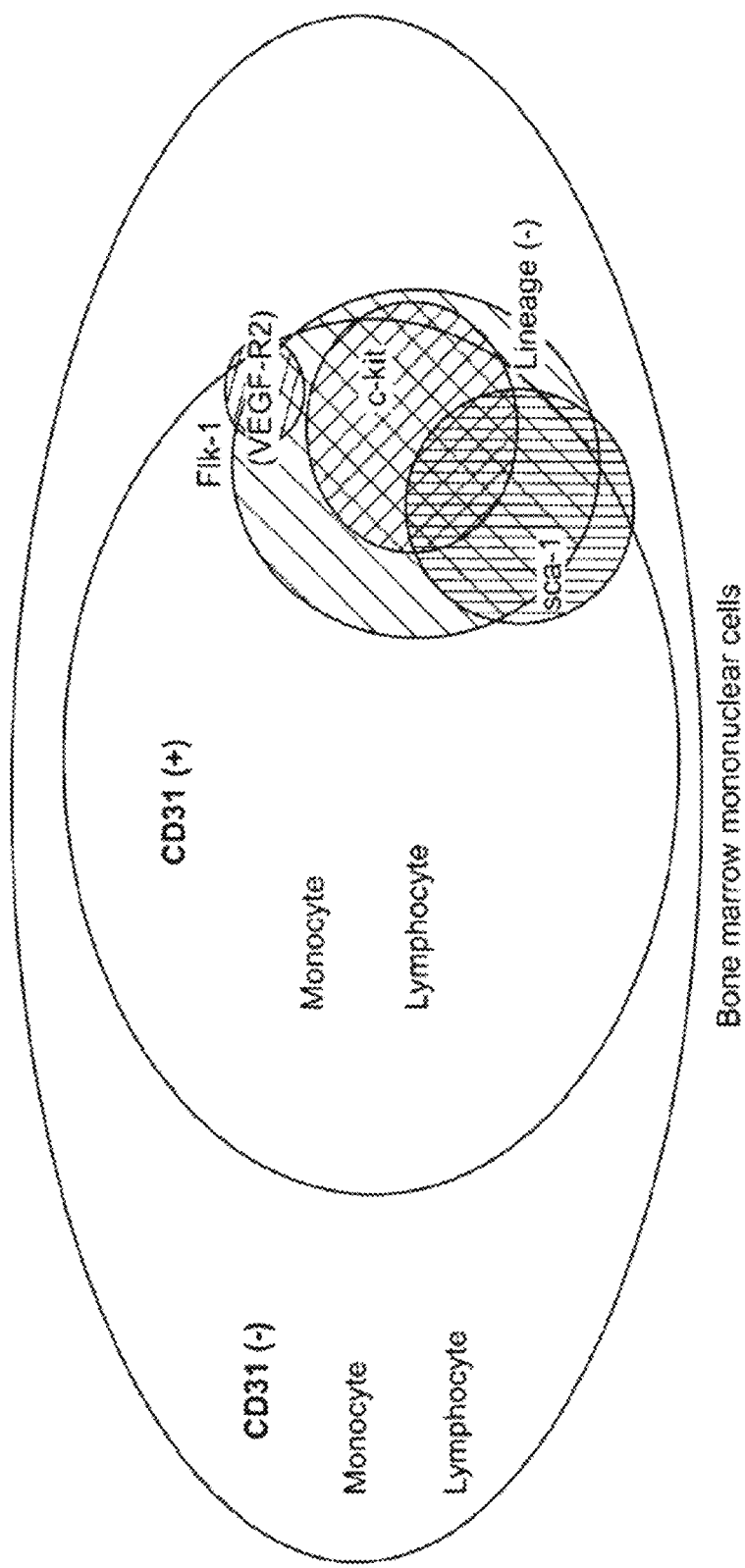
FIG. 2 provides a graphical representation showing the sub-classification of bone marrow mononuclear cells divided by CD31.

CD31 was identified as a surface epitope common to most stem or progenitor cells that have therapeutic effects in cardiovascular regeneration or repair. In particular, FACS analysis demonstrated that CD34$^+$ human hematopoietic cells and precursors of both myeloid and lymphoid cells express high levels of CD31[36,37]. 99% of c-kit$^+$ sca-1$^+$ lineage$^-$ cells (KSL cells), a population of BM-derived hematopoietic stem cells, also expressed CD31. Side population cells in BM are predominantly CD31 positive. In addition to adult stem cells, pluripotent embryonic stem cells also express CD31 constitutively at undifferentiated stages despite lacking vascular structure and the absence of angiogenic factors. An analysis of the antigen expression profiles of BM-MNCs demonstrates that around 30% of whole BM-MNCs express the CD31 antigen (FIGS. 1A to 1H) and CD31+ cells are co-expressed with other well-known stem cell markers such as CD34, c-kit and Flk-1 (FIGS. 1I to 1K). When lineage positive cells were depleted, these co-expression patterns were much more obvious (FIGS. 1L to 1N). Taken together, these findings indicate that the CD31 antigen may function as a unique and comprehensive marker that is expressed by most if not all stem cells showing hemangioblastic activity in the BM (FIG. 2).

Example 2

Harvesting BM-Mononuclear Cells and CD31 Selection

Figure 3C:
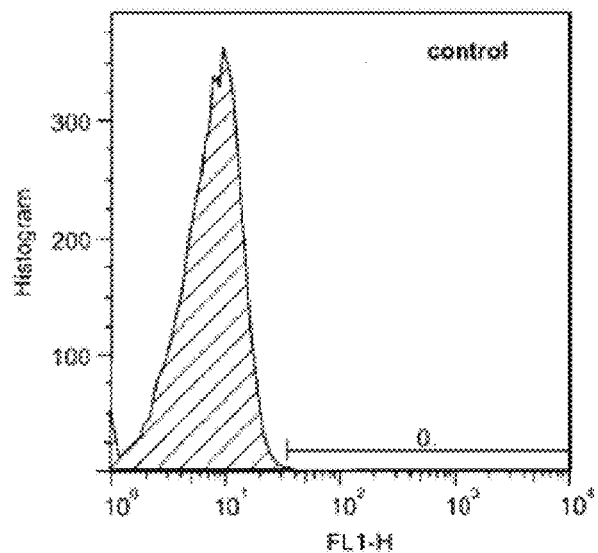
FIG. 3C shows CD31 positive histogram showing the results of FACS analysis following CD31+/− selection with magnetic labeled beads. The purity after magnetic sorting is confirmed by flow cytometry analysis against CD31 (CD31-Neg: CD31-negatively selected cells; CD31-Pos: CD31-positively selected cells).
Figure 3C:
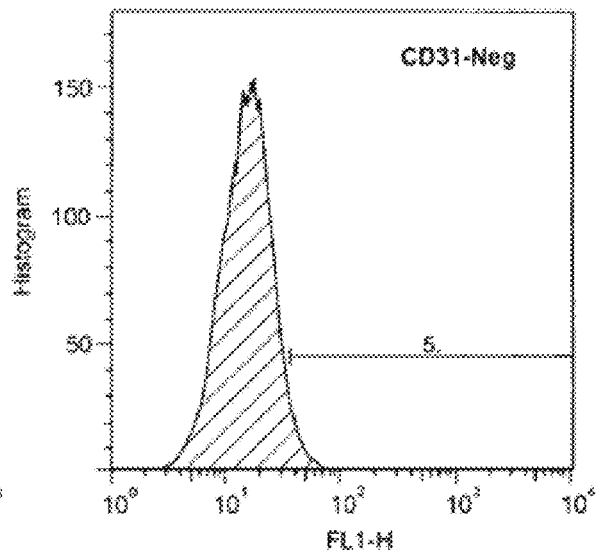
Figure 3C:
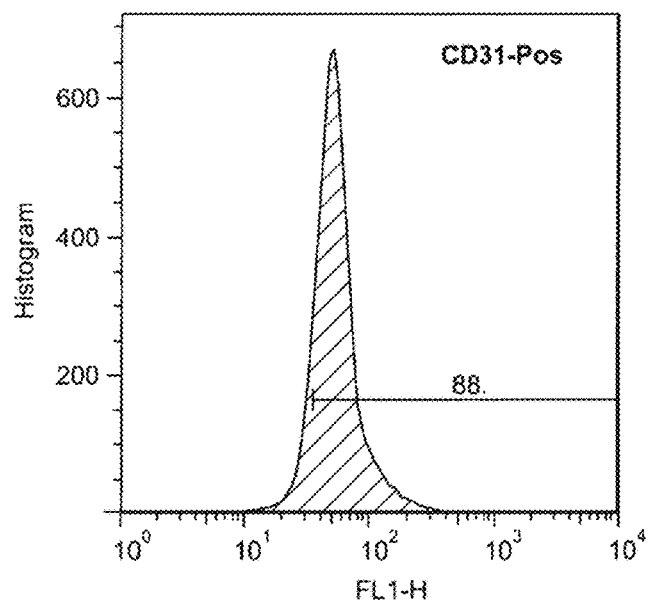

BM cells were harvested from mice after euthanasia. BM cells were obtained by grinding thigh bones, forelimb bones, and sternum with PBS/2 mM EDTA. After passing the lysate through 70 and 40 μm nylon filters to remove particulate debris, mononuclear cells were isolated by density gradient centrifugation with Histopaque 1083 (Sigma). BM-MNCs were labeled with rat anti-mouse-CD31 monoclonal antibody (BD Pharmingen) for 30 minutes, followed by incubation with goat anti-rat IgG magnetic beads (Mitenyi Biotec) for 20 minutes. Then, the cells were sorted through a magnetic column (MACS®, Mitenyi Biotec). CD31$^-$ cells pass through the magnetic column and the remaining cells in the column are CD31$^+$ cells. Bead-bound cells (CD31$^+$) are retrieved from the column by flushing with PBS. Results for sorting efficiency are shown in FIGS. 3A-C. Overall, at least 85% purity was confirmed by flow cytometry after cell sorting with the magnetic beads. Trypan blue staining revealed that CD31$^+$ and CD31$^-$ cells were more than 90% viable after the procedure.

Example 3

Colony Forming Unit Assay

To investigate whether CD31$^+$ or CD31$^-$ cells have a higher potential for proliferation and differentiation to form mesodermal derivatives, colony forming unit assays will be performed after lineage-committed cell depletion. An initial density of 7,000 cells/mL will be cultured on methylcellulose media (Methocult GF M3534 or M3231 media, Stem Cell Technologies) and analyzed for colony formation after 10 days in culture. Whole lineage-depleted BM-MNCs will serve as an internal control for the colony forming culture.

Example 4

3. CD31+ Cells Express Multiple Angiogenic Genes

Figure 4:
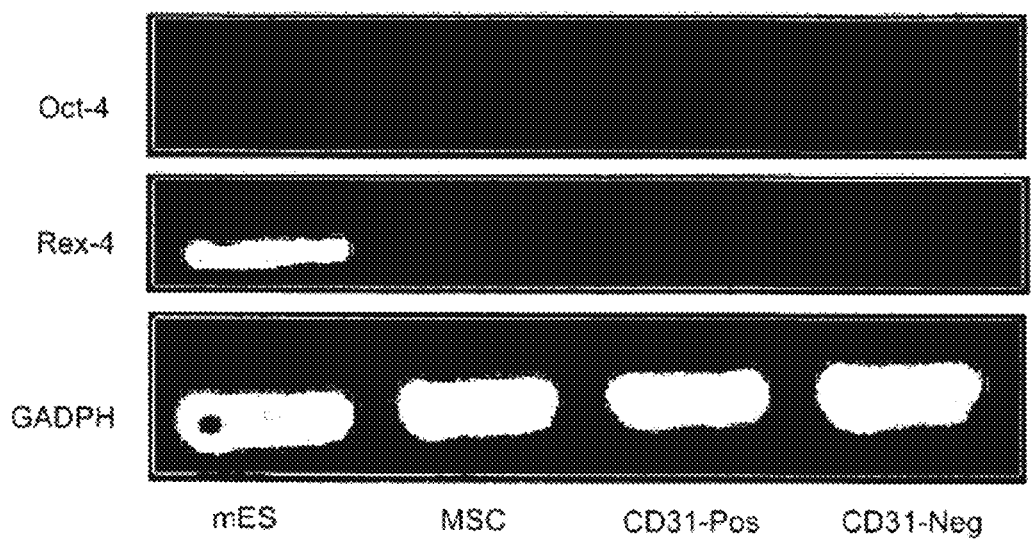
FIG. 4 provides the results of an RT-PCR showing embryonic gene expression profiles of Oct-4 and Rex-4 in mouse embryonic stem (mES), mesenchymal stem cells (MSc), CD31$^+$, and CD31$^−$ cells. GAPDH expression is included as a control.

Gene expression profiles were assayed using reverse transcriptase-polymerase chain reaction (RT-PCR) and microarray analysis. To evaluate embryonic gene expression, RNA was extracted from whole BM-MNCs, CD31$^+$ and CD31$^-$ cells as previously described[33]. cDNA was generated using a reverse transcription kit (Promega) according to the manufacturer's instructions. PCR was performed on cDNA using mouse specific primers: octamer-binding transcription factor 4 (Oct4), RNA exonuclease 4 (Rex4), Nanog, Sox2, SSEA-1, and GAPDH. This analysis showed that CD31+ cells express several embryonic genes exclusively (FIG. 4). Mouse embryonic stem cells (mES) serve as a positive control and mesenchymal stem cells (MSC) as a negative control. For the evaluation of the other genes known to be important for the identification, growth and differentiation of mouse stem cells microarray (GEArray S Series, Mouse Stem Cell Gene Array: MA4-601.2) examination is performed using RNA samples.

Example 5

CD31+ Cells Possess BM Repopulating Potential

Figure 5:
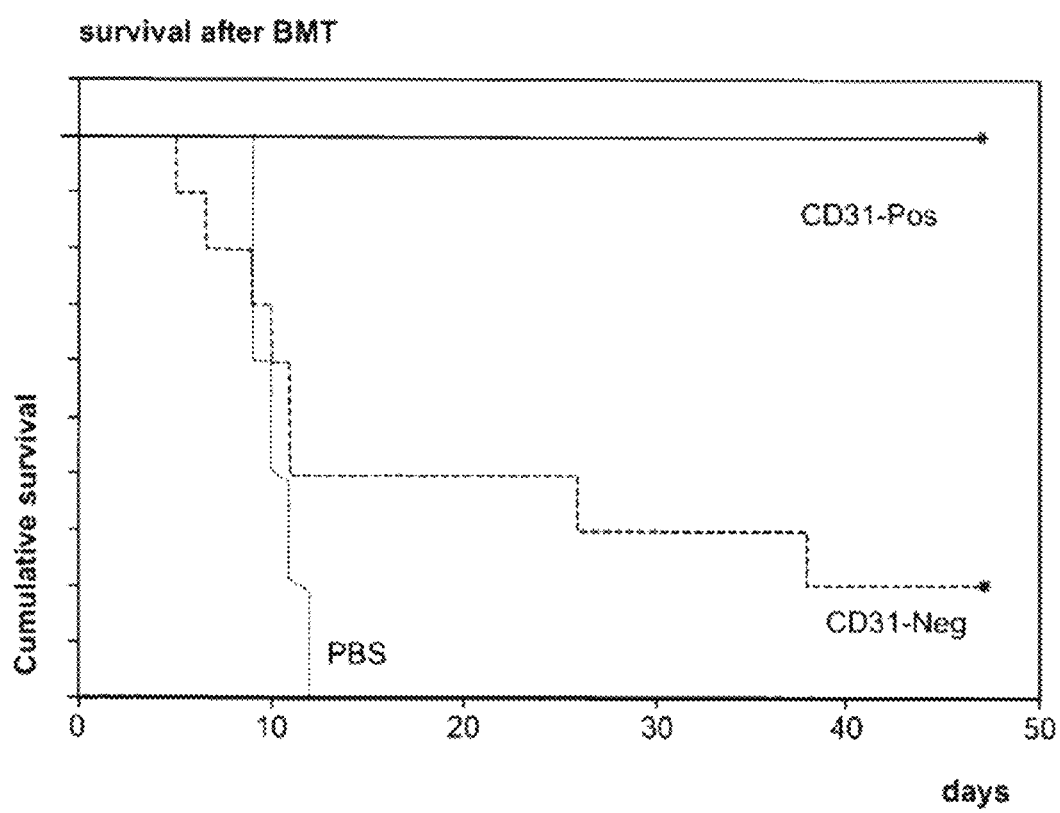
FIG. 5 is a graph showing the hematopoietic potential of CD31$^+$ cells. CD31 sorted cells from BM-MNCs were transplanted into lethally irradiated mice. CD31$^+$ cells rescued 100% of recipient mice and CD31$^−$ cells failed to provide a degree of protection from a lethal dose of radiation (n=10, CD31+ and CD31− groups, respectively, n=5 for PBS group).

To demonstrate that BM-derived CD31$^+$ cells have self-renewing potential, BM repopulating potential was examined using a BM transplantation (BMT) model. GFP transgenic mice with a C57BL/6J background (male, 6-8 weeks) were used as donors for the BMT. C57BL/6J mice (female, 6-8 weeks, Jackson Laboratories), which were used as recipients for BMT. The procedure of BMT was performed as described previously. Briefly, recipient mice were lethally irradiated with 1,200 cGγ in 2 equal doses of 600 cGγ delivered 3 hours apart. CD31$^+$ or CD31$^-$ cells were injected intravenously into the tail vein. Recipients received antibiotic water for 1 month after transplantation and survival was monitored daily. At 6 to 8 weeks after BMT, which is sufficient time for the reconstitution of the BM of the recipient mice, both BM and peripheral blood mononuclear cells were analyzed for the engraftment of GFP cells using FACS. Also, to confirm the long-term repopulation and engraftment, BM cells from primary recipients were harvested to isolate GFP+ cells, which were then transplanted in secondary recipients. These studies showed that CD31$^+$ cells repopulated BM in lethally irradiated BMT models (FIG. 5). CD31$^+$ cells rescued lethally-irradiated recipients.

A fraction of CD31$^+$ cells of BM mononuclear cells in C57BL/6 mice co-expressed well known stem cell markers including c-kit, Sca-1, and flk-1. The expression levels of these markers were distinct when hematopoietic lineage positive cells were depleted (Lin$^-$) from CD31$^+$ cells. Moreover, Lin$^-$CD31$^+$ cells exclusively expressed genes characteristic of cells having pluripotency, including Oct4, Rex4, Nanog, and SSEA-1. A microarray analysis revealed that CD31$^+$ cells expressed multiple angiogenic genes compared to CD31$^-$ cells. In particular, only a CD31$^+$ but not CD31$^-$ fraction gave rise to endothelial progenitor cells (EPCs) in a culture assay. To determine in vivo activity, we performed BM repopulating experiments. All mice that were transplanted with 1×10$^5$ CD31$^+$ cells survived after lethal irradiation, whereas mice that received CD31$^-$ cells all died within 4 weeks (n=10, each).

FACS analysis is performed using a modification of previously described procedures to characterize subsets of CD31$^+$ cells. This study uses the following exemplary antibodies (all are monoclonal antibody for mice and from BD Pharmingen): fluorescein isothiocyanate (FITC)-conjugated anti-CD31; phycoerythrin (PE)-conjugated anti-CD3, anti-CD4, anti-CD5, anti-CD8, anti-CD11b, anti-CD45R (B220), anti-GR-1 (Ly-6G), anti-Ter119, anti-CD45, anti-CD34, anti-c-kit, anti-Sca-1, and anti-Flk1. Furthermore, the surface antigens of lineage-depleted cells is analysed: stem cells lineages (c-kit, Sca-1, CD34), vascular progenitors (Flk-1), and embryonic stem cells (SSEA-1, Oct-4). Flow cytometry analysis is performed on a FACSCAN (Becton-Dickinson) or MoFlo (DAKO). Acquired data are analyzed using specialized software FlowJo® (Tree Star, Inc), version 5.7. Depletion of committed cells is performed as described below. Harvested BM-MNCs are incubated with a lineage cocktail of biotin-conjugated anti-mouse monoclonal antibodies (all from Miltenyi Biotec): CD5, CD45R, CD11b, GR-1, 7-4 and Ter119. Magnetic beads are conjugated to a monoclonal anti-biotin antibody (Miltenyi Biotec). The antibody non-bound (lineage-depleted) fraction is collected by negative selection from exposure to a magnetic filed.

Example 6

CD31+ Cells Express Multiple Angiogenic Genes

Figures 6A, 6B:
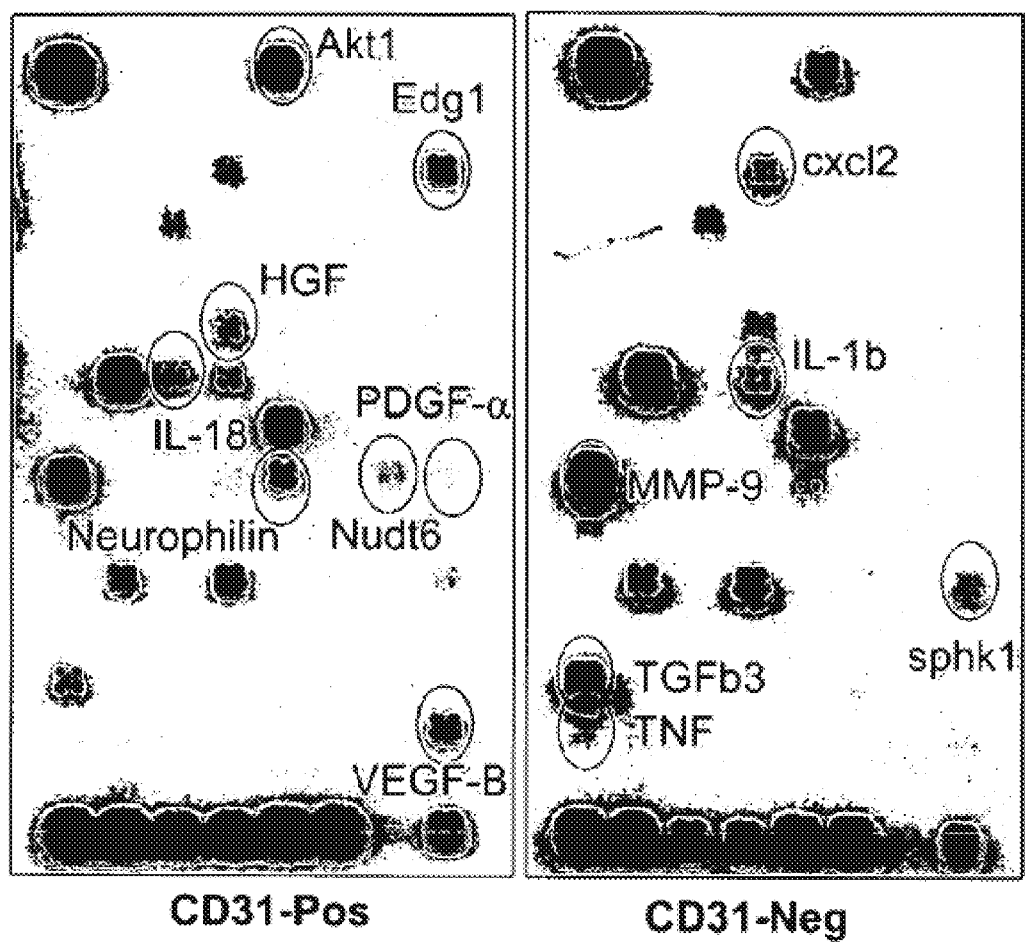
FIG. 6A shows microarray gene expression profiles of CD31 positive cells for Akt-1, endothelial differentiation sphingolipid G-protein-coupled receptor 1 (Edg1), human growth factor (HGF), interleukin-18 (IL-18), neurophilin, nucleoside diphosphate linked moiety X-type motif 6 (Nudt6), platelet derived growth factor-α, vascular endothelial growth factor-B (VEGF-B), chemokine (C-X-C motif) ligand 2 (cxcl2), IL-1β, matrix metalloprotease-9 (MMP-9), sphingosine kinase type 1 (sphk1), transforming growth factor-B3, tumor necrosis factor (TNF). Angiogenic microarray shows differential expressions on multiple genes between two groups.
FIG. 6B shows CD31 negative cells.

Angiogenic gene expression was compared by microarray analysis of BM-derived CD31+ and CD31− subpopulations. (GEArray®, Mouse Angiogenesis Microarray, OMNI-024, SuperArray). RNA was extracted from whole BM-MNCs, $CD31^+$ and $CD31^-$ cells. This array was designed to profile the expression of 113 key genes involved in modulating the biological processes of angiogenesis; the array contains growth factors and receptors, cytokines, chemokines, adhesion molecules, proteases, inhibitors and other matrix proteins, transcription factors, and others. The data were analyzed by GEArray Analysis Suite®. Results using microarray analysis showed different patterns of gene expression patterns between $CD31^+$ and $CD31^-$ cells. (FIGS. 6A and B).

CD31+/CD31− gene expression ratio
Ang-1 1.72-fold
Ang-2 2.55-fold
Akt 5.05-fold
Edg1 16.23-fold
bFGF 2.23-fold
IGF-1 2.01-fold Example 7

Proliferation, Survival and Migration Assay Characterization $1 \times 10^4$ cells of lineage-depleted $CD31^+$ or $CD31^-$ cells, respectively are seeded in each well of a 96-well plate in a final volume of 200 µl/well. After a 48 hour incubation, the cell survival reagent, WST-1 (Roche molecular biochemicals) is added as 20 µL/well. The proliferative activities of each cell type is assessed by ELISAs for BrdU incorporation (Roche Diagnostics, Germany) after 24 and 72 hours. The modified Boyden's chamber method is used for migration assays as previously described[64].

Example 8

Characterization of CD31+ Cells Angiogenic Potential

In Vitro Incorporation into HUVEC Monolayer.

Human umbilical vein endothelial cells (HUVECs, Cambrex) are cultured to form a monolayer in 6-well plates. One hundred thousand $CD31^+$ or $CD31^-$ cells derived from GFP mice will be seeded onto a HUVEC monolayer. After 4 hours of incubation, the wells are gently washed with PBS three times and five random fields are selected to count the number of cells incorporating into the HUVEC monolayer per unit area.

In Vitro Tube Formation.

Basement membrane matrix, Matrigel® (Becton Dickinson Labware) is added to chamber slides. After one-hour incubation at room temperature, $2 \times 10^4$ cells are added to the chamber slides with 500 µl EGM-2 media. Twelve hours later, four representative fields are counted and the average of the total area of complete tubes formed by cells per unit area is compared by Image-Pro Plus®.

Measurement of Cytokine Concentration of Supernatant.

To investigate whether $CD31^+$ or $CD31^-$ cells produce angiogenic, anti-apoptotic, mitogenic, and chemotactic factors, VEGF, HGF, IGF-1, bFGF, Angiopoietin-1, 2, TNF-α, IL-1β, IL-6, IL-8, IL-12, IL-16, and SDF-1 levels are measured in conditioned medium obtained from the $CD31^+$ or $CD31^-$ 24 hours after medium replacement by ELISAs.

Example 9

CD31+ Cells Give Rise to Endothelial Progenitor Cells

Figure 7A:
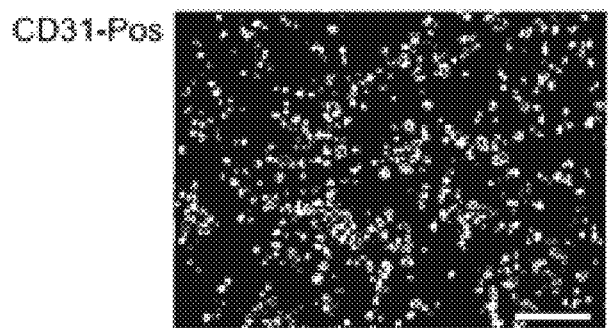
FIG. 7A shows a fluorescent micrograph of an endothelial progenitor cell (EPC) culture assay for CD31 positive cells. CD31$^+$ cells gave rise to EPCs exclusively, compared to CD31− cells. Ac-DiI-LDL, BS-1 lectin, DAPI. n=7 fields, each. *P<0.001, Whole vs. CD31-Neg; **P<0.001, Whole, CD31-Neg vs. CD31-Pos
Figure 7B:
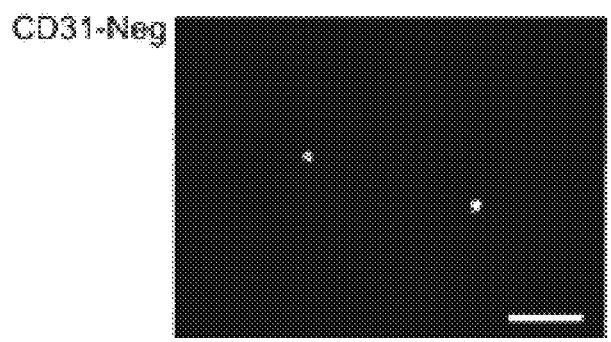
FIG. 7B shows CD31 negative cells.
Figure 7C:
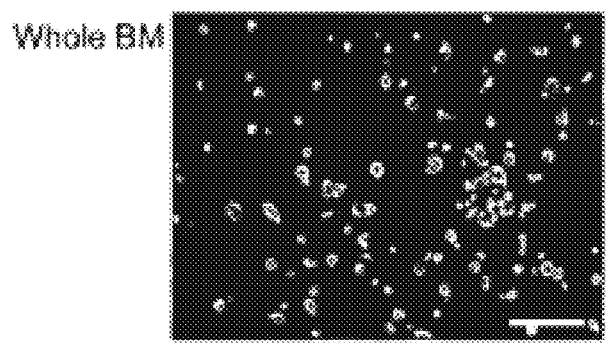
FIG. 7C shows whole BM.
Figure 7D:
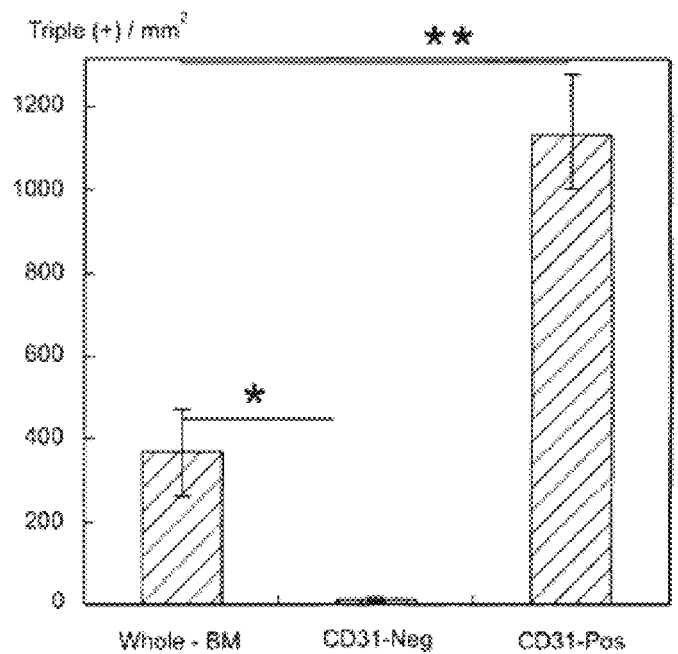
FIG. 7D shows a graph.
Figure 8:
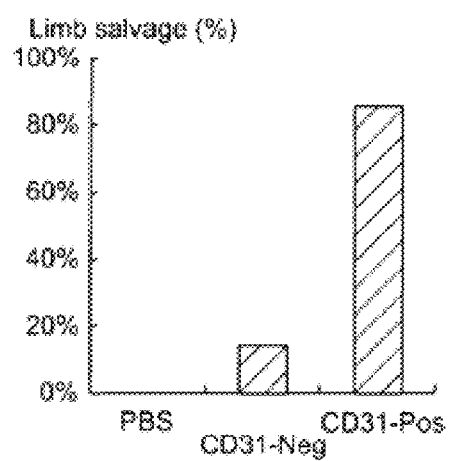
FIG. 8 shows data on the therapeutic efficacy of CD31$^+$ cells. CD31$^+$ cell transplantation showed greater efficacy to improve limb survival.
Figures 9A, 9B, 9C:
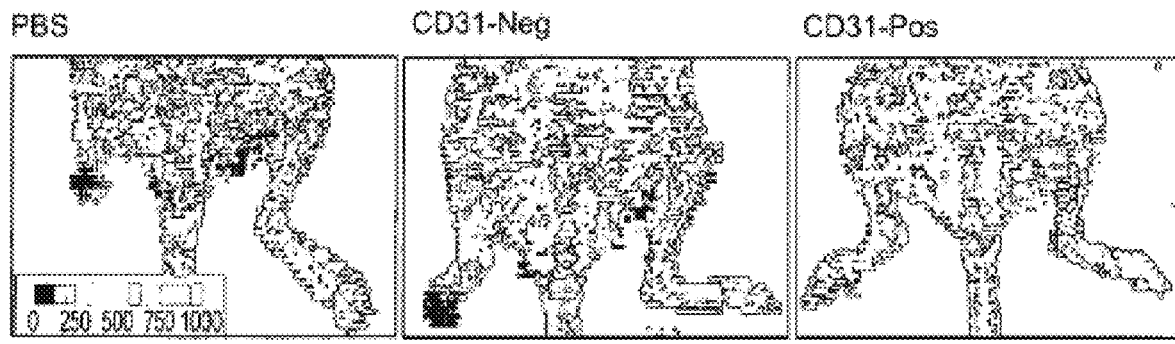
FIG. 9A shows limb perfusion at 14 days after cell transplantation for PBS.
FIG. 9B shows for CD31 negative cells
FIG. 9C shows for CD31 positive cells.
Figure 9D:
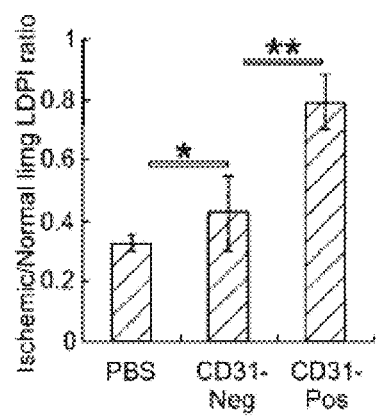
FIG. 9D is a graph showing the quantification of perfusion improvement. *P=0.629, **P=0.009, (n=3, each).

CD31+ or CD31− cells were plated onto a 2-well chamber slide, $2 \times 10^6$ cells/slide density. The cells were cultured in culture media, 5% fetal bovine serum (FBS)/endothelial basal media (EBM-2) medium supplemented with 5% fetal bovine serum, antibiotics, and cytokine cocktail (SingleQuots) (Clonetics, San Diego, Calif.) consisting of human epidermal growth factor, vascular endothelial growth factor (VEGF), human fibroblast growth factor-basic (FGF-2), insulin-like growth factor-1 (IGF-1), ascorbic acid. (SingleQuots, Clonetics). At day 4, attached cells were evaluated by staining. Triple positive cells showing DiI-acetylated low density lipid (acLDL) (Molecular Probe) uptake, FITC-conjugated BS-1 lectin (*Bandeiraea simplicifolia* lectin I, Vector Laboratories) binding and DAPI positivity in nucleus were counted as EPCs. At least 5 randomly chosen fields were averaged for statistical analysis. Culture conditions were optimized as shown in FIG. 7A to 7C, and 7B. Surprisingly, EPCs originate exclusively from a $CD31^+$ subset. Whole BM-MNCs were cultured under the same conditions and used as an internal control for EPC culture quality.

In addition to the marker study, functional measurements are performed to characterize the endothelial cell phenotype using any one or more of the following assays.

Nitric Oxide (NO) Formation

Intracellular nitric oxide (NO) formation is analyzed using diamino-fluorescein-2 diacetate (DAF-2 DA, Daiichi, Japan), a membrane NO-specific fluorescence indicator. To compare the intensity of fluorescence the image is captured during a fixed exposure time by manual operation and then get the intensity profile of fluorescence of each cell with Image-Pro Plus®.

Vascular Progenitor Cell Culture Assay $CD31^+$ or $CD31^-$ cells are resuspended in culture medium, EGM-2 MV, and subsequently cultured in either EGM-2 MV to induce and maintain endothelial phenotype or EGM-2 supplemented with 10% FBS and platelet derived growth factor (PDGF)-BB stimulation (10 ng/ml, R&D systems) to facilitate vascular smooth muscle phenotype. After 2 weeks in culture, morphological appearance and immunocytochemical staining are used to define cellular phenotypes. To detect an endothelial cell phenotype, primary antibodies against von Willebrand factor (vWF) (DAKO), which are detected with phycoerythrin- (PE-) conjugated goat anti-rat IgG, and antibodies against a-smooth muscle actin (FITC-conjugated, SIGMA) are used to detect vascular smooth muscle cells.

Protective effects on cardiomyocytes and skeletal myocytes in co-culture

For the evaluation of direct protective effects on cell transplantation, CD31$^+$ or CD$^-$ cells are co-cultured with cardiomyocytes and satellite cells (muscle precursors) derived from skeletal muscles. Neonatal rat cardiomyocytes are isolated and cultured from syngenic Fisher rats as previously described[33] and satellite cells are harvested from adult wild type C57BL mice[66]. CD31$^+$ or CD31$^-$ cells are cultured with cardiomyocytes or satellite cells at a ratio of 1:4~1:8 for 7~14 days. Cell cultures are performed under a normoxic conventional condition, a hypoxic-condition, and a hydrogen peroxide ($H_2O_2$, 100 µM)-stimulated condition. Terminal dUTP nick-end labeling (TUNEL) and activated-caspase 3 staining are used to quantify anti-apoptotic effects of sorted cells on CMCs and satellite cells. To investigate pro-survival and anti-apoptotic effects of CD31+ or CD31– cells, total Akt, phosphorylated Akt and IGF-1 are measured by Western blot.

Furthermore, lineage-depleted and CD31$^+$ or CD31$^-$ cells derived from GFP transgenic mice, which exclude lineage-committed cells such as monocytes, B and T lymphocytes, are co-cultured to determine the differentiation (transdifferentiation) potential of these cells into cardiomyocytes. To confirm the possibility of cell-to-cell fusion in mediating myogenic differentiation of these cells, co-culture with satellite cells derived from ROSA26 mice will be performed in skeletal myogenic differentiation media. One day after co-culture, media supplement will be changed from fetal bovine serum to horse serum in order to induce muscle differentiation.

CD31$^+$ or CD31$^-$ cells derived from GFP expressing transgenic mice (C57BL/6J background) were used in a hindlimb ischemia model and a myocardial infarction model. For a hindlimb ischemia model, both nude mice and syngenic C57BL/6J mice are used. Multifarious analysis is performed in mice models. Primary endpoints are physiologic and functional improvements, such as a reduction in ischemic limb loss, an increase in hindlimb blood flow, and increases in cardiac systolic and diastolic function. Secondary endpoints are area of fibrosis and vascular density in histology samples. To track the fates of transplanted cells in tissues with the use of GFP mice, the differentiation potential of transplanted cells is examined using immunohistochemical methods. Co-localization of transplanted cells (GFP$^+$) with lineage markers (endothelial cell, vascular smooth muscle cells, myocytes) identifies transdifferentiated cells.

Example 10

CD31+ Cells Possess Greater Efficacy to Repair Ischemic Limbs

CD31+ cells were tested in a mouse hindlimb ischemia model as previously descibed[69]. In brief, a ligation was made around the femoral artery and all arterial branches were removed. The consistency of limb ischemia and the prognosis associated with this model was previously confirmed in our laboratory. To test the therapeutic effects of cell therapy, CD31$^+$ or CD31$^-$ cells were washed gently with PBS and introduced via tail vein. The dose of injected cells was 1×10$^6$ per mouse and the suspension volume was 200 µL. Whole BM-MNCs and PBS injected mice served as controls. The chimeric or transdifferentiation potential of injected cells into vasculogenic or myogenic lineages was determined by immunofluorescent histochemistry. Co-localization of injected cells derived from GFP transgenic mice with each lineage marker such as von Willebrand factor (for endothelial cells, DAKO), or a-sarcomeric actin (for muscles, Sigma), is indicative of transdifferentiation or chimerism. Untreated mice consistently lose ischemic hindlimbs following surgery due to impaired angio-vasculogensis (FIGS. 9A to 9C and 9D). Mice treated with CD31$^+$ cells were more effective in restoring circulation and rescuing ischemic limbs than CD31$^-$ cells.

Doppler perfusion imager (LDPI, Moor instrument, UK), which maps tissue blood flow by the shift in the laser light frequency, was used for serial noninvasive physiological evaluation. After 2 weeks of limb ischemia, the CD31$^+$ cell group showed increased limb perfusion and capillary density as well as greater efficacy in the salvage of ischemic limbs, compared to mice injected with PBS, whole BM cells and CD31$^-$ cells (n=7, each). Mean values of perfusion were calculated from the stored digital color-coded images. Results of hindlimb blood flow at the two week time point was expressed as the ratio of left (ischemic) to right (non-ischemic) to avoid data variations caused by ambient light and temperature.

Example 11

CD31+ Injection Enhances Function and Healing After Myocardial Infarction

Myocardial infarction was induced by ligating the left anterior descending coronary artery with 8-0 prolene suture. The apex of the left ventrical was observed for evidence of myocardial blanching and akinesia indicating interruption in coronary flow. Immediately after ligation, CD31$^+$ (5×10$^5$) or CD31$^-$ cells with the 50 µl suspended volume were injected into the myocardial wall using 27 G needle. All surgical procedures were carried out with an operating microscope (Zeiss) at ×5 to ×24 magnification. Whole BM-MNCs and PBS injected mice served as controls. Mice were assayed at 2 and 4 weeks following myocardial infarction and cell transplantation. At both time points, systolic and diastolic functions were improved and fibrosis-scar size was smaller in mice receiving CD31$^+$ cells compared to the control groups (n=5, each).

Methods of assaying for efficacy in the treatment of myocardial ischemia are known in the art. In one example, at post-operative day 14 and 28, echocardiography and pressure transducer measurements are performed. Two-dimensional images and M-mode tracings are recorded from the parasternal short axis view at the level of papillary muscle. From M-mode tracings, anatomical parameters in diastole and systole are obtained. For hemodynamic studies, the right carotid artery is cannulated with a microtip pressure transducer (Millar 1.4F).

Treatment efficacy will be assessed by measuring fibrosis-scar size. From ischemic limbs, the gastrocnemius muscle is harvested and stained with Sirius red, and collagen volume fraction is measured. In the infarcted heart, Masson's trichrome staining will be performed on left ventricle samples harvested at 2 and 4 weeks after infarction. Morphometric analysis of fibrosis length and area is performed with a computerized digital image-analysis system.

Example 12

CD31+ Cells Enhance Angio-Vasculogensis

Figure 10A:
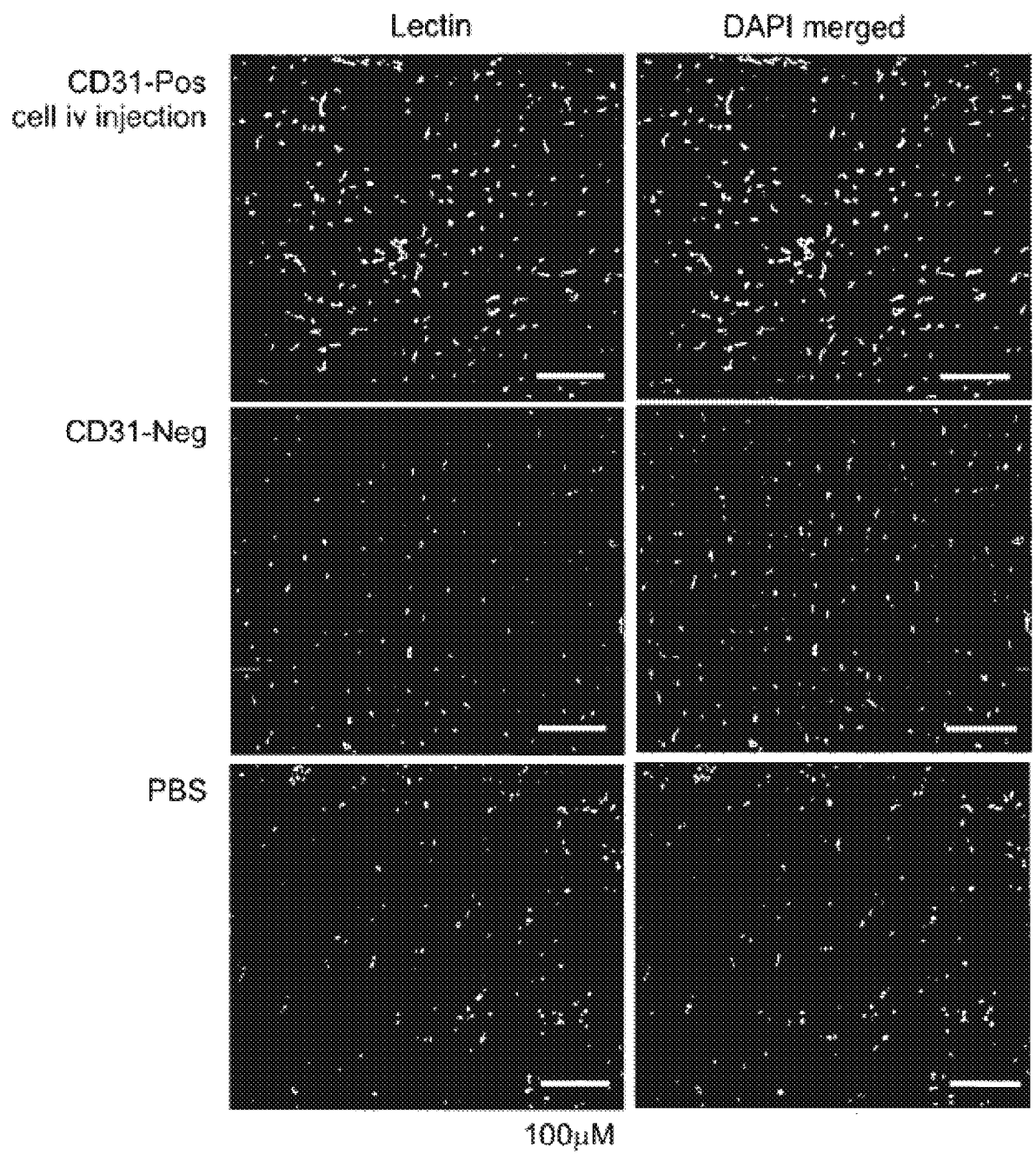
FIG. 10A shows the results of a histology analysis of ischemic limb. Capillary densities were measured at 14 days. Administration of CD31+ cells increased capillary density in ischemic tissue.
Figure 10B:
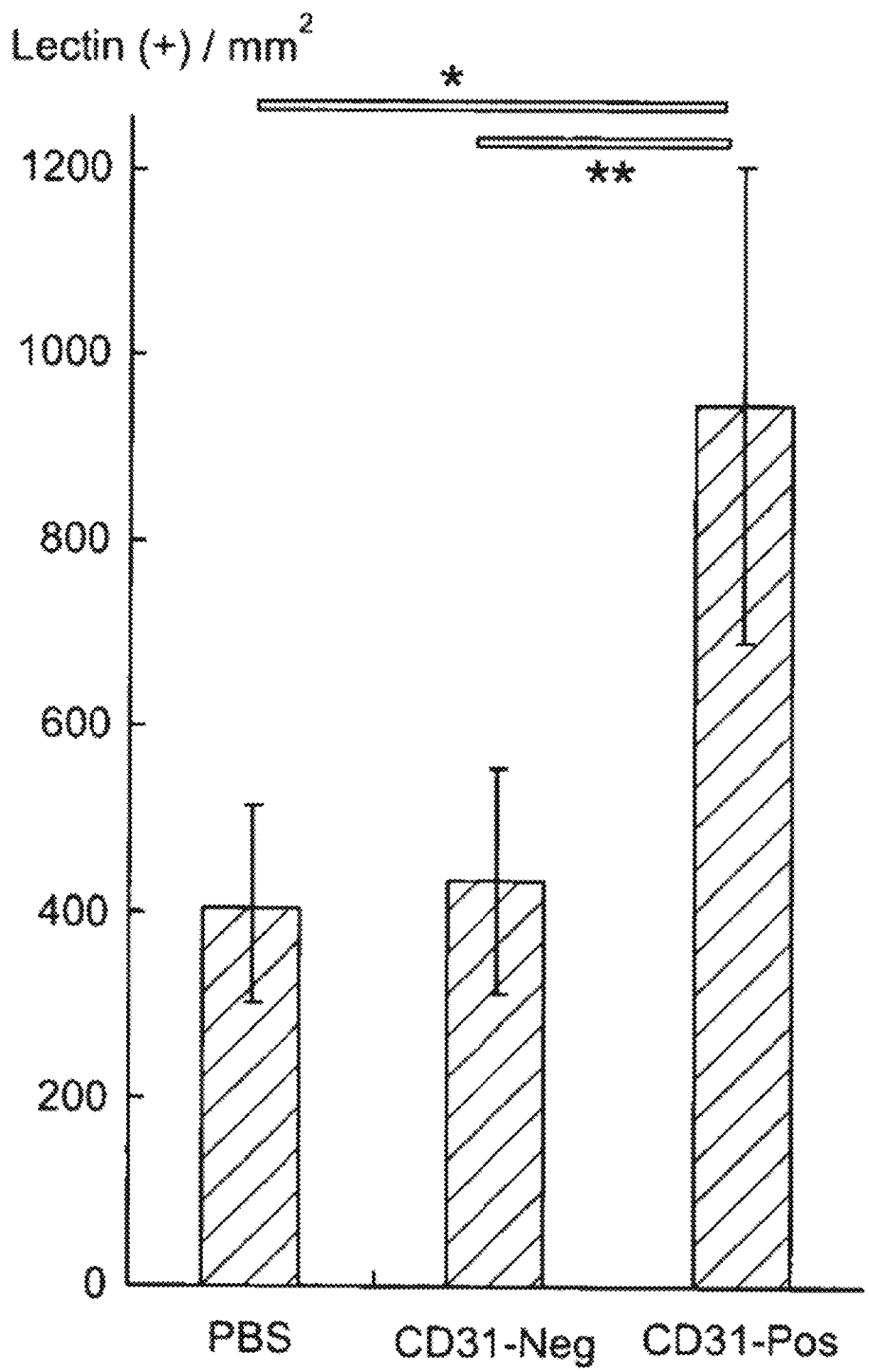
FIG. 10B provides a quantitative analysis of capillary density expressed as the number of lection-positive cells per mm$^2$. *P=0.001, PBS vs. CD31-Pos; **P=0.002, CD31-Neg vs. CD31-Pos. (n=5, each)

Isolectin B4 staining (Vector Laboratories) was performed with frozen sections of ischemic limbs harvested 2 weeks after ischemic injury. Tissues were counterstained with nuclear DAPI. Lectin staining, which represents capillaries, was used to measure capillary density. Capillary density is calculated from at least 5 randomly selected fields. The number of capillaries is converted to the number per square millimeter. As shown in FIGS. 10A and 10B, CD31$^+$ cell transplantation group showed increased capillaries. Also, functionally competent vessels containing vascular smooth muscle layers are identified with an antibody against α-smooth muscle actin and size (>300 μm$^2$). All immunostaining is visualized using conventional inverted fluorescence microscopy and/or laser scanning confocal microscopy.

To detect S-G2-M phase cells, Ki-67 staining is performed using anti-Ki-67 antibody (Novocastra Laboratories) with frozen sections of limbs and left ventricular specimens harvested at 1 and 2 weeks after ischemia. In infarcted heart specimens, the number of positive stained nuclei is measured from both peri-infarct and remote-infarct area. To measure a cumulative fraction of proliferative cell throughout the study period[33], mini-osmotic pump releasing BrdU is implanted and anti-BrdU staining is performed. To measure apoptosis, a TUNEL assay is performed using the fluorescein in-situ cell death detection kit (Roche-Molecular) with frozen sections harvested at 1 week after ischemia. In addition to TUNEL, activated, cleaved caspase-3 staining is used to detect apoptosis. To determine the proportion of proliferative or apoptotic nuclei within myocytes (or cardiomyocyte), tissue are counterstained with antibodies against α-sarcomeric actin (Sigma) or cardiac Troponin I (Sigma).

Example 13

CD31+ Cells Incorporated Into Vasculature and Replenished Vessels in Ischemic Tissues Donor cells having anti-GFP staining were used to investigate the co-localization of donor cells together with markers for other cell types, such as endothelial cells, vascular smooth muscle cells, myocytes, and cardiomyocytes. Results shown in FIG. 11 indicated that CD31$^+$ cells likely undergo tissue specific immunophenotypic conversion to replenish vessels in ischemic tissues (FIG. 11A-C).

Vascular lineage differentiation is assayed as follows. Tie-2/LacZ transgenic mice are used as cell donors. Cells of these mice express β-gal if endothelial lineage differentiation is determined by Tie-2 promoter activation throughout development and in the adult.

As reported herein, CD31$^+$ acts as a comprehensive marker that is expressed in most if not all of the currently identified BM cells showing hemangioblastic activity. These findings suggest that a strategy of CD31$^+$ cell transplantation may have significant therapeutic potential for repairing ischemic limb and heart.

Example 14

Expression of Angiogenesis Related Genes

The expression of angiongenesis related genes on CD31$^+$ cells was determined. BM cells were harvested from mice after euthanasia. CD31$^+$ and CD31$^-$ cells were obtained by magnetic cell sorting (MACS, Miltenyi Biotec, Germany) and subjected to RNA isolation using Trizol. Microarray analysis was carried out using a GeneChip Mouse Genome 430 2.0 Array (Affymetrix). 22,691 probe sets were examined and 5,121 probe sets were excluded due to weak signal strength compared to the background signal. Among the remaining 17, 658 probesets, 6,132 probesets showed statistically significant regulation between CD31$^+$ vs. CD31$^-$. 2,158 probesets revealed statistical significance with a fold-change of more than 2 (1, 290 genes up-regulated and 868 genes down-regulated in CD31$^+$ cells compared to CD31$^-$ cells).

Figure 12:
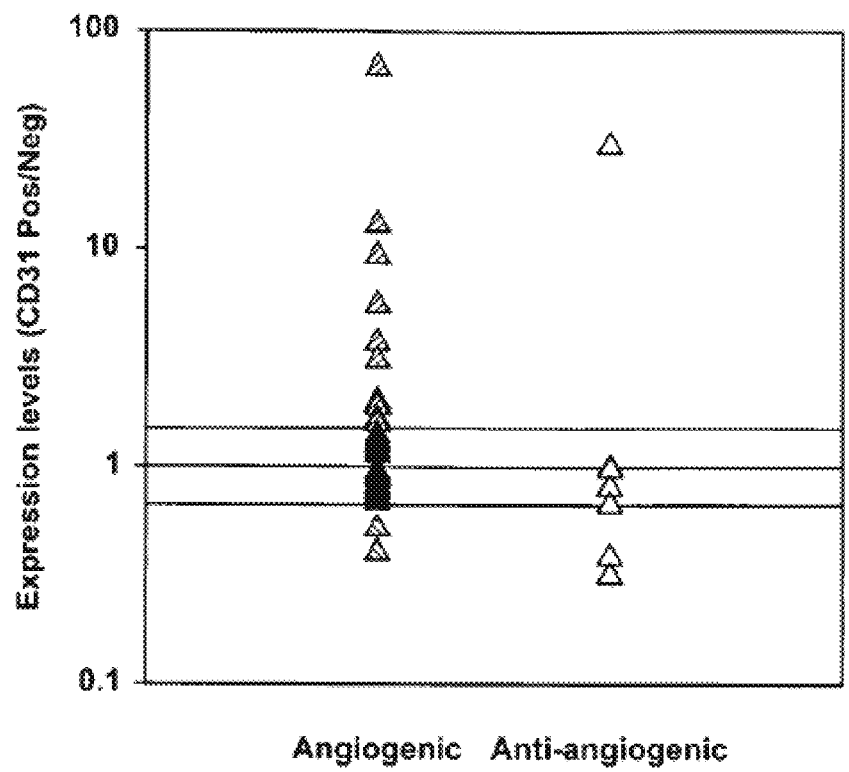
FIG. 12 shows angiogenesis-related gene expression levels in CD31$^+$ cells. Each dot represents relative expression levels of an angiogenesis-related gene in CD31$^+$ cells relative to CD31− cells.

To investigate angiogenic gene expression in CD31$^+$ and CD31$^-$ cells, we selected 60 angiogenesis-related genes (50 angiogenic genes, 10 anti-angiogenic genes) that code secreted proteins or extracellular matrix proteins (proteins were selected based on literature review and affymetrix annotation). Among the 60 genes, 43 genes were expressed in CD31$^+$ or CD31$^-$ cells. Genes that were significantly increased and decreased in CD31+ cells with more than 1.5-fold were indicated by letters (Table 1A and B) or triangular dot (FIG. 12), respectively.

TABLE 1A

| Angiogenic genes | | | |
|---|---|---|---|
| UniGeneID | Gene Symbol | Gene Description | Pos/Neg |
| Mm.1019 | Il6 | interleukin 6 | 68.31 |
| Mm.309336 | Angpt1 | angiopoietin 1 | 12.92 |
| Mm.331089 | Pdgfc | platelet-derived growth factor, C polypeptide | 9.32 |
| Mm.268521 | Igf1 | insulin-like growth factor 1 | 5.53 |
| Mm.2675 | Pdgfa | platelet derived growth factor, alpha | 3.70 |
| Mm.1402 | Vegfc | vascular endothelial growth factor C | 3.09 |
| Mm.1410 | Il18 | interleukin 18 | 1.99 |
| Mm.241282 | Fgf1 | fibroblast growth factor 1 | 1.93 |
| — | Ang1 | angiogenin, ribonuclease A family, member 1 | 1.88 |
| Mm.795 | Csf1 | colony stimulating factor 1 (macrophage) | 1.87 |
| Mm.15607 | Vegfb | vascular endothelial growth factor B | 1.65 |
| Mm.144089 | Pdgfb | platelet derived growth factor, B polypeptide | 1.57 |
| Mm.137222 | Tgfa | transforming growth factor alpha | 1.39 |
| Mm.267078 | Hgf | hepatocyte growth factor | 1.31 |
| Mm.289681 | Hbegf | heparin-binding EGF-like growth factor | 1.26 |
| Mm.377077 | Ang2 | angiogenin, ribonuclease A family, member 2 | 1.19 |
| Mm.6813 | Bmp4 | bone morphogenetic protein 4 | 1.15 |
| Mm.18213 | Tgfb2 | transforming growth factor, beta 2 | 1.13 |
| Mm.189536 | Angpt4 | angiopoietin 4 | 0.95 |
| Mm.390018 | Angpt2 | angiopoietin 2 | 0.94 |
| — | Tnfsf12/// Tnfsf12-tnfsf13 | tumor necrosis factor (ligand) superfamily, member 12/// tumor necrosis factor (ligand) superfamily, member 12-member 13 | 0.94 |

TABLE 1A-continued

Angiogenic genes

| UniGeneID | Gene Symbol | Gene Description | Pos/Neg |
|---|---|---|---|
| Mm.258415 | Nos3 | nitric oxide synthase 3, endothelial cell | 0.91 |
| Mm.32171 | Fgf2 | fibroblast growth factor 2 | 0.91 |
| Mm.29564 | Mmp2 | matrix metallopeptidase 2 | 0.90 |
| Mm.57202 | Shh | sonic hedgehog | 0.88 |
| Mm.303231 | Cxcl12 | chemokine (C-X-C motif) ligand 12 | 0.86 |
| Mm.390122 | Pdgfd | platelet-derived growth factor, D polypeptide | 0.81 |
| Mm.4956 | Fgf4 | fibroblast growth factor 4 | 0.79 |
| Mm.173813 | Notch4 | Notch gene homolog 4 (*Drosophila*) | 0.79 |
| Mm.227 | Itgav | integrin alpha V | 0.77 |
| Mm.1810 | Ctgf | connective tissue growth factor | 0.76 |
| Mm.293761 | Pofut1 | protein O-fucosyltransferase 1 | 0.73 |
| Mm.1238 | Csf3 | colony stimulating factor 3 (granulocyte) | 0.68 |
| Mm.87365 | Prok2 | prokineticin 2 | 0.68 |
| Mm.4406 | Mmp9 | matrix metallopeptidase 9 | 0.52 |
| Mm.282184 | Vegfa | vascular endothelial growth factor A | 0.40 |

TABLE 1B

Anti-angiogenic genes

| UniGeneID | Gene Symbol | Gene Description | Pos/Neg |
|---|---|---|---|
| Mm.332490 | Cxcl4 | chemokine (C-X-C motif) ligand 4 | 29.73 |
| Mm.874 | Il10 | interleukin 10 | 0.98 |
| Mm.26688 | Thbs2 | thrombospondin 2 | 0.96 |
| Mm.1421 | Adamts1 | a disintegrin-like and metallopeptidase (reprolysin type) with thrombospondin type 1 motif, 1 | 0.80 |
| Mm.4159 | Thbs1/// LOC640441 | thrombospondin 1/// similar to thrombospondin 1 | 0.66 |
| Mm.206505 | Timp2 | tissue inhibitor of metalloproteinase 2 | 0.38 |
| — | LOC640441 | similar to thrombospondin 1 | 0.31 |

Example 15

Identity of CD31+ Cells

CD31$^+$ cells were characterized as follows.

Figure 13:
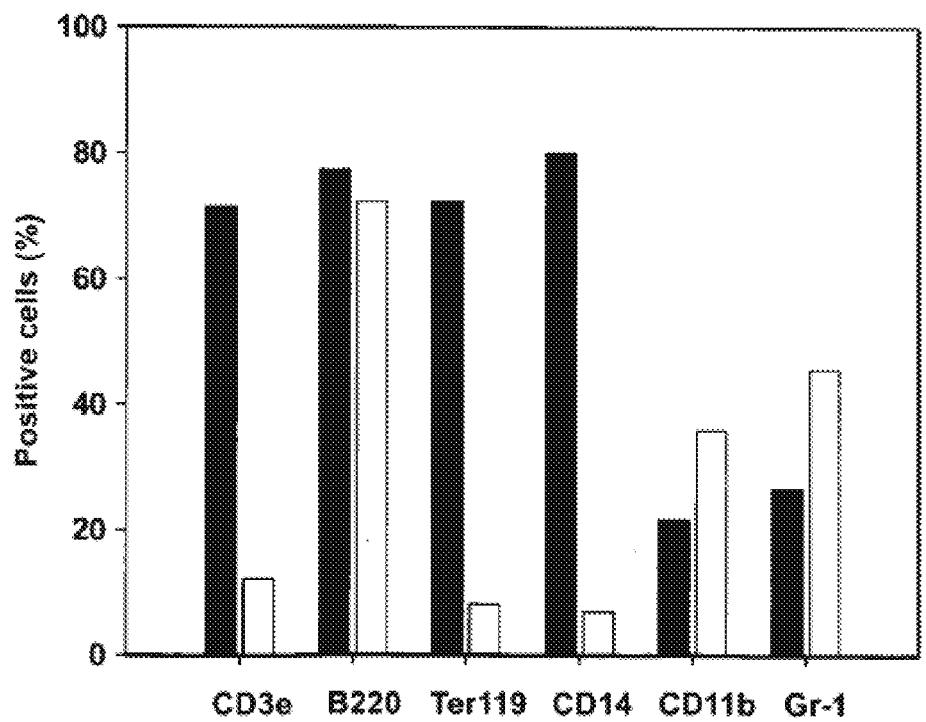
FIG. 13 shows the expression of lineage markers in CD31$^+$ cells. Each closed bar represents the percentage of CD31+ cells among the specific marker positive cells and each open bar represents the percentage of specific marker positive cells among CD31+ cells from murine bone marrow cells.
Figure 14A:
FIG. 14A shows limb perfusion after cell transplantation of CD31 positive cells in a hind limb ischemia model. One million cells were intramuscularly injected after femoral artery ligation. Limb perfusion at 14 days after cell transplantation.
Figure 14B:
FIG. 14B shows CD31 negative cells.
Figure 14C:
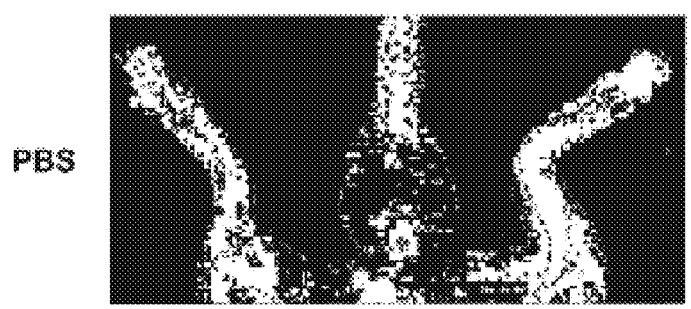
FIG. 14C shows PBS.

To characterize the CD31$^+$ cells from murine bone marrow, we double-stained the BM-derived MNCs with lineage markers and CD31 to determine what kind of cells compose CD31$^+$ cells (FIG. 13). The percentage of CD31$^+$ cells among CD3e+ (mainly T lymphocytes), B220+ (mainly B lymphocytes) and CD14$^+$ cells (mainly monocyte/macrophages) is more than 70%, whereas CD11b+ (mainly monocytes and myeloid) and Gr-1+ (mainly granulocytes) cells make up less than 30%. The most dominant component of CD31$^+$ cells is B220$^+$ cells, which constitute 70% of all CD31+ cells.

Example 16

Blood Flow and Vascularity in the Hindlimb Ischemia Model

A hindlimb ischemia model was used to evaluate blood flow and vascularity. To induce hindlimb ischemia, ligation was made around the femoral artery and all arterial branches were removed. To test the therapeutic effects of cell therapy, CD31$^+$ or CD31$^-$ cells were washed gently with PBS and injected intramuscularly. The dose of injected cells was $1 \times 10^6$ per mouse and the suspension volume was 200 µL. Whole BM-MNCs and PBS injected mice served as controls.

Laser Doppler perfusion imager (LDPI, Moor instrument, UK), which maps tissue blood flow by the shift in the laser light frequency, was used for serial noninvasive physiological evaluation. Each mouse was followed by serial recording of surface blood flow immediately after surgery, and at day 3, 7, 14, and 21. Mean values of perfusion were calculated from the stored digital color-coded images. The limb blood flow was expressed as the ratio of left (ischemic) to right (non-ischemic) to avoid data variations caused by ambient light and temperature (FIGS. 14A to 14C and 14D).

Isolectin B4 staining (Vector Laboratories) was performed with frozen sections of limbs harvested at 2 weeks after ischemic injury (FIGS. 15A and 15B). Capillary density was calculated from the capillary counts from at least 5 randomly selected fields. All immunostaining was visualized using conventional inverted fluorescence microscopy and/or laser scanning confocal microscopy. Tissues were counterstained with nuclear DAPI.

Example 17

Tracking of Engrafted Cells

Figure 16A:
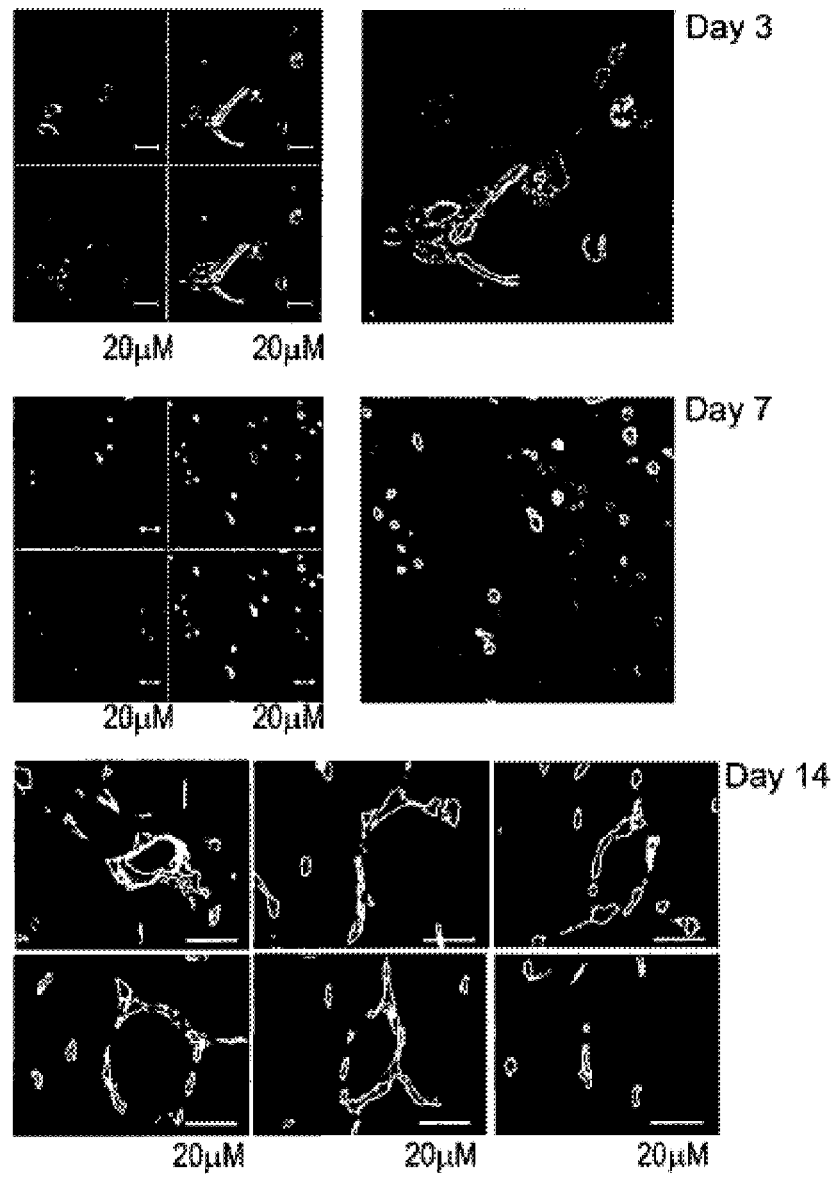
FIG. 16A shows the fate of CD31+ cells after transplantation into ischemic limb. CD31+ cells from GFP expressing mice incorporated into vasculature over 3-14 days. Representative images stained for GFP (Anti-GFP antibody), isolectin, and nuclear counterstaining (DAPI) demonstrate incorporation into endothelial cell and pericyte locations.
Figure 16B:
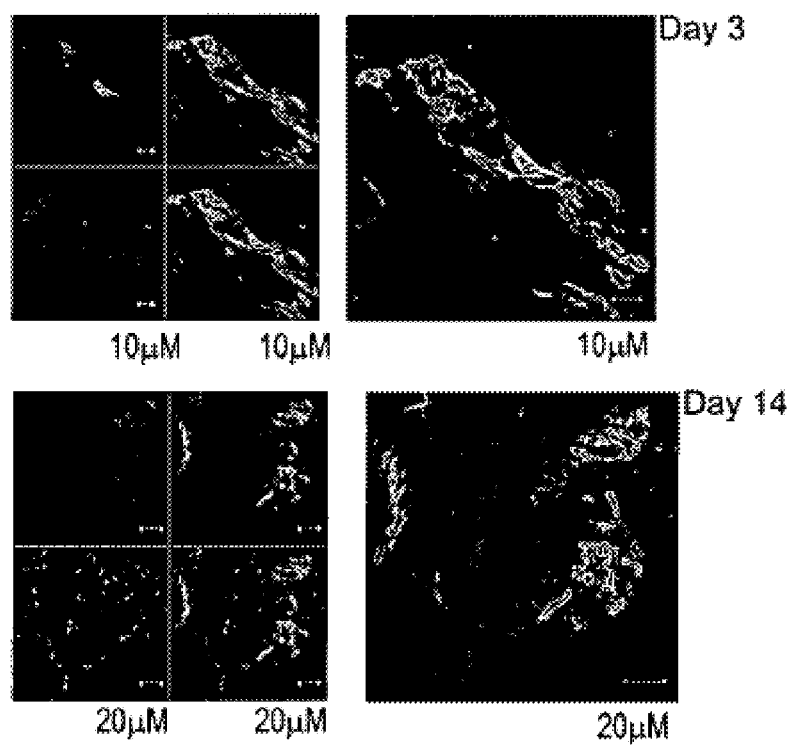
FIG. 16B shows day 3 and day 14 as it relates to FIG. 16A.

To determine the phenotypic changes of the transplanted cells, cells from GFP expressing mice were injected into the ischemic hind limb model of an ischemic hindlimb mouse model. The localization of the injected cells with anti-GFP staining followed by confocal microscopy was determined. As shown in FIGS. 16A and 16B, CD31$^+$ cells successfully incorporated into vessels at the location of endothelial cells and pericytes.

Example 18

Transdifferentiation of CD31+ Cells into Endothelial Cells in Vitro

Figure 17A:
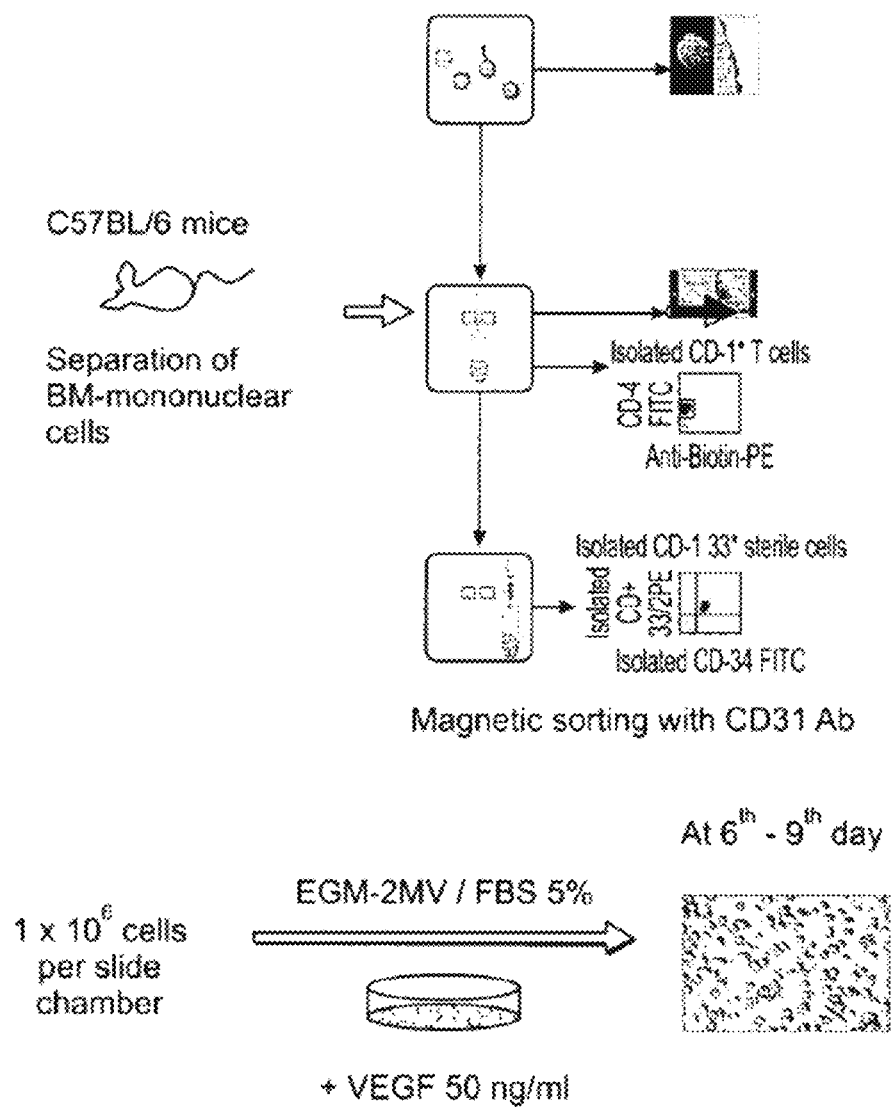
FIG. 17A shows differentiation of CD31+ cells into endothelial cells in vitro. One million CD31+ cells from murine bone marrow were plated on 2 well chamber slides and cultured in EGM-2MV supplemented with 5% FBS and 50 ng/ml VEGF. Cultured cells started to show a cobble stone appearance at day 5
Figure 17B:
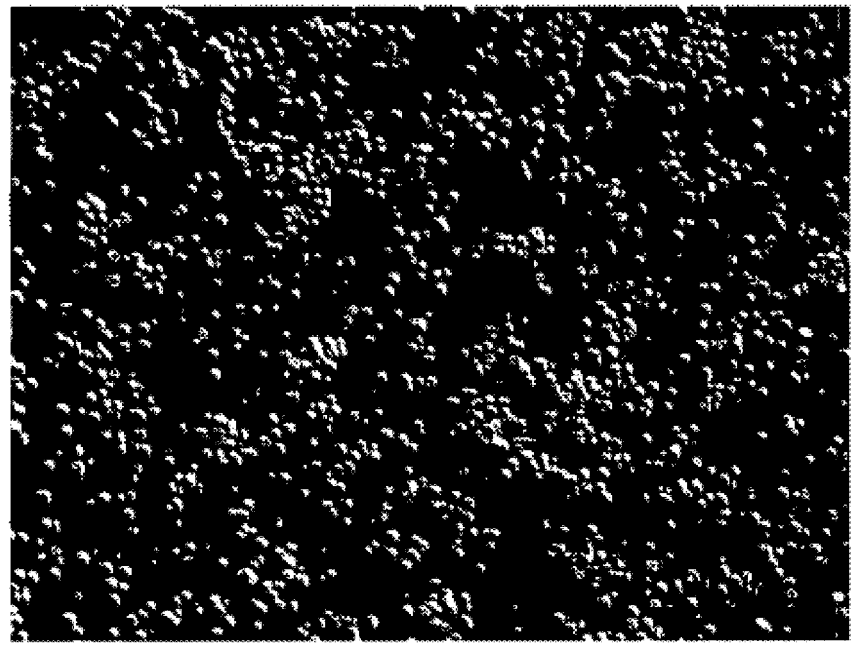
FIG. 17B shows day 1.
Figure 17C:
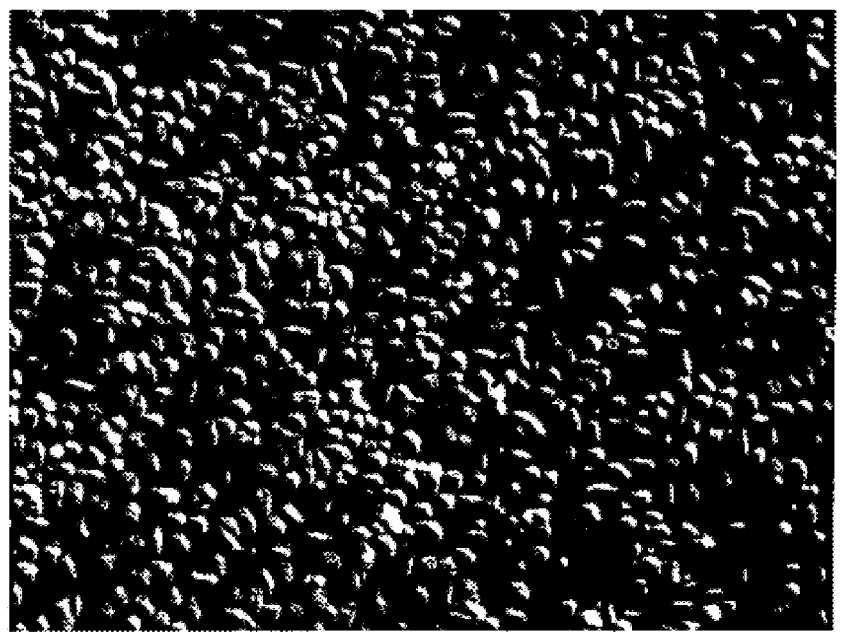
FIG. 17C shows that day 5 differentiation of CD31+ cells into ECs were demonstrated by positive immuocytofluorescent staining for endothelial specific markers.
Figure 17D:
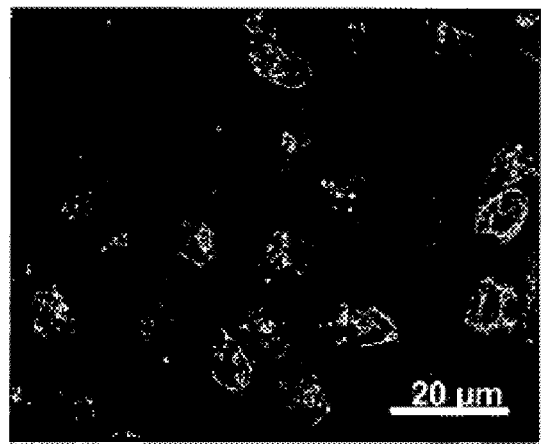
FIG. 17D shows vWF, D8.
Figure 17E:
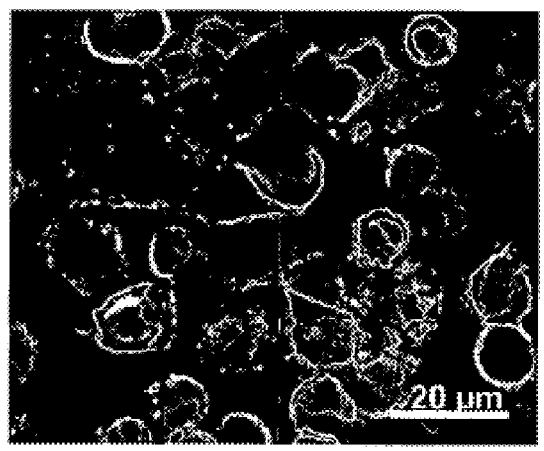
FIG. 17E shows ILB4, ac-Dil-LDL, D8.
Figure 17F:
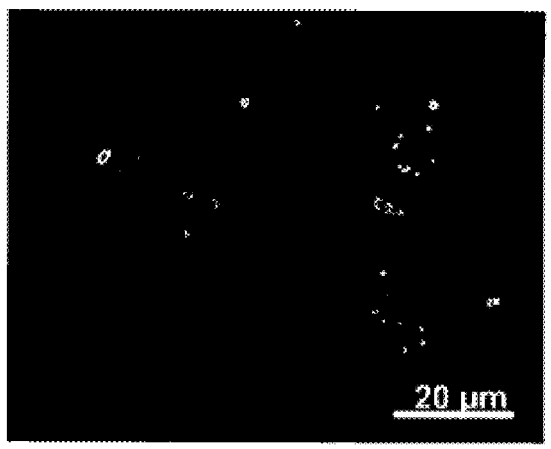
FIG. 17F shows VE-CAD, D9.
Figure 17G:
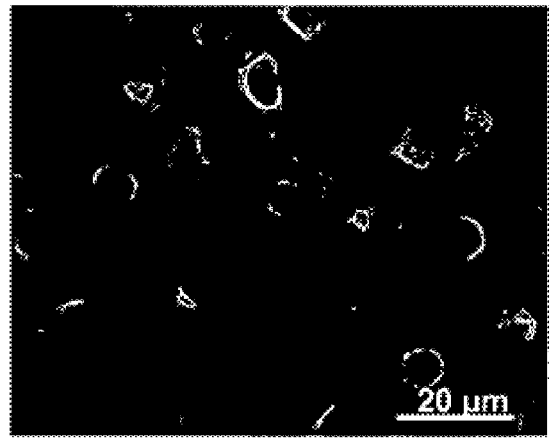
FIG. 17G shows VEGFR-2, D9.
Figure 17H:
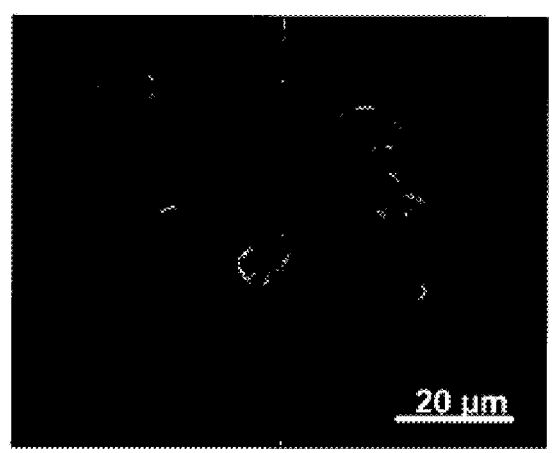
FIG. 17H shows CD31, D9.

To investigate whether CD31$^+$ cells can be induced to undergo differentiation into endothelial cells in vitro, we cultured CD31$^+$ cells supplemented with VEGF-A as outlined in FIG. 17A. CD31$^+$ cells underwent differentiation into endothelial cells in vitro as demonstrated by changes in morphology and the expression of endothelial cell specific markers (FIGS. 17A and 17B to 17C).

Example 19

Evaluation of the Surface Marker Phenotype of Human CD31+ and CD31− Cells

Cells were analyzed with a FACStar flow cytometer. CD31+ cells were labeled with PE- or FITC-conjugated Abs against human CD11b, CD14, CD31, CD45, CD105, CD141, CD144, CD146 or isotype controls. Lines, control Ig; a line, specific Ab.

Surface Molecule Analysis

Figure 18A:
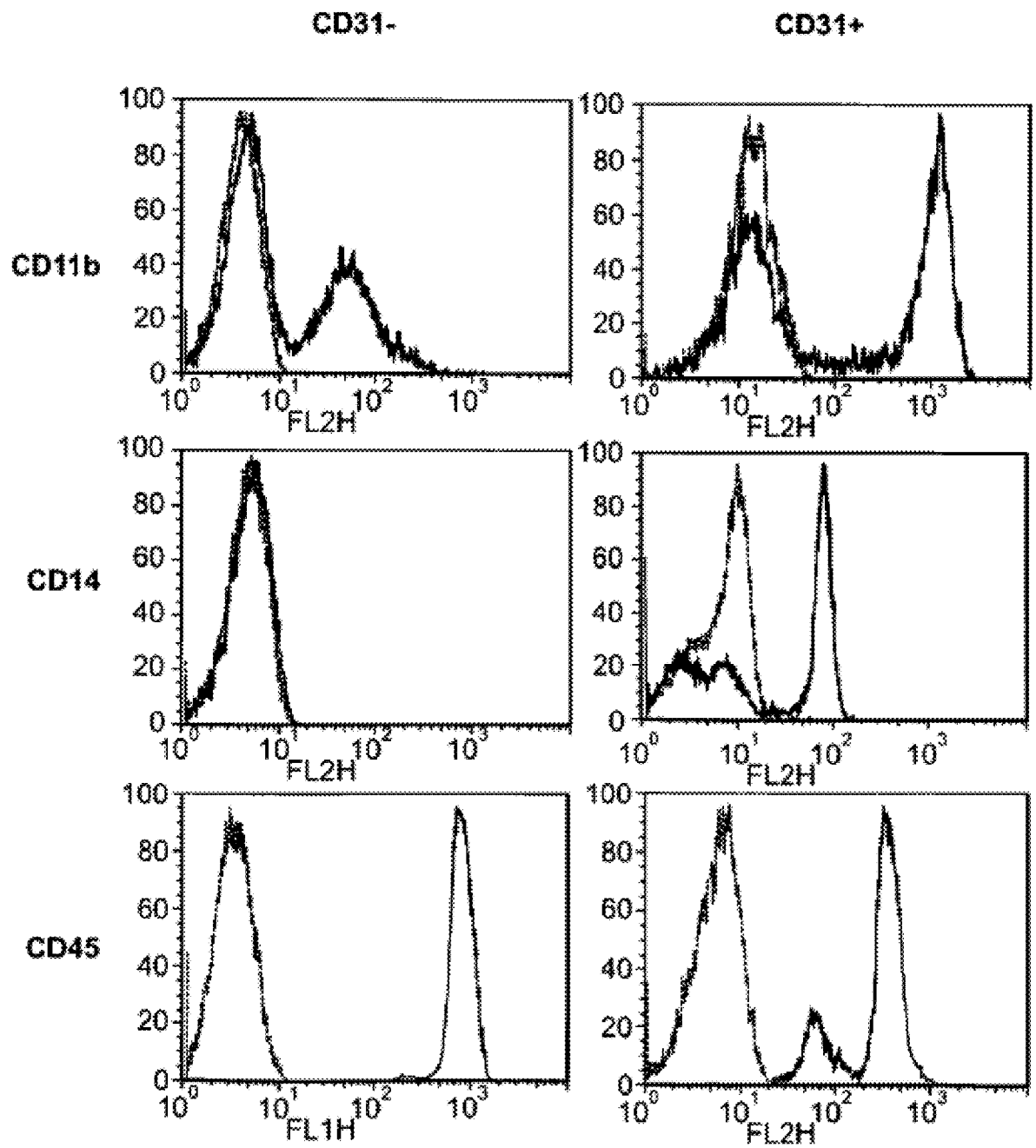
FIG. 18A shows the characteristics of CD31+ and CD31− cells. Cells were analyzed with a FACStar flow cytometer. CD31+ cells were labeled with PE- or FITC-conjugated Abs against human CD11b, CD14, CD31, CD45.
Figure 18B:
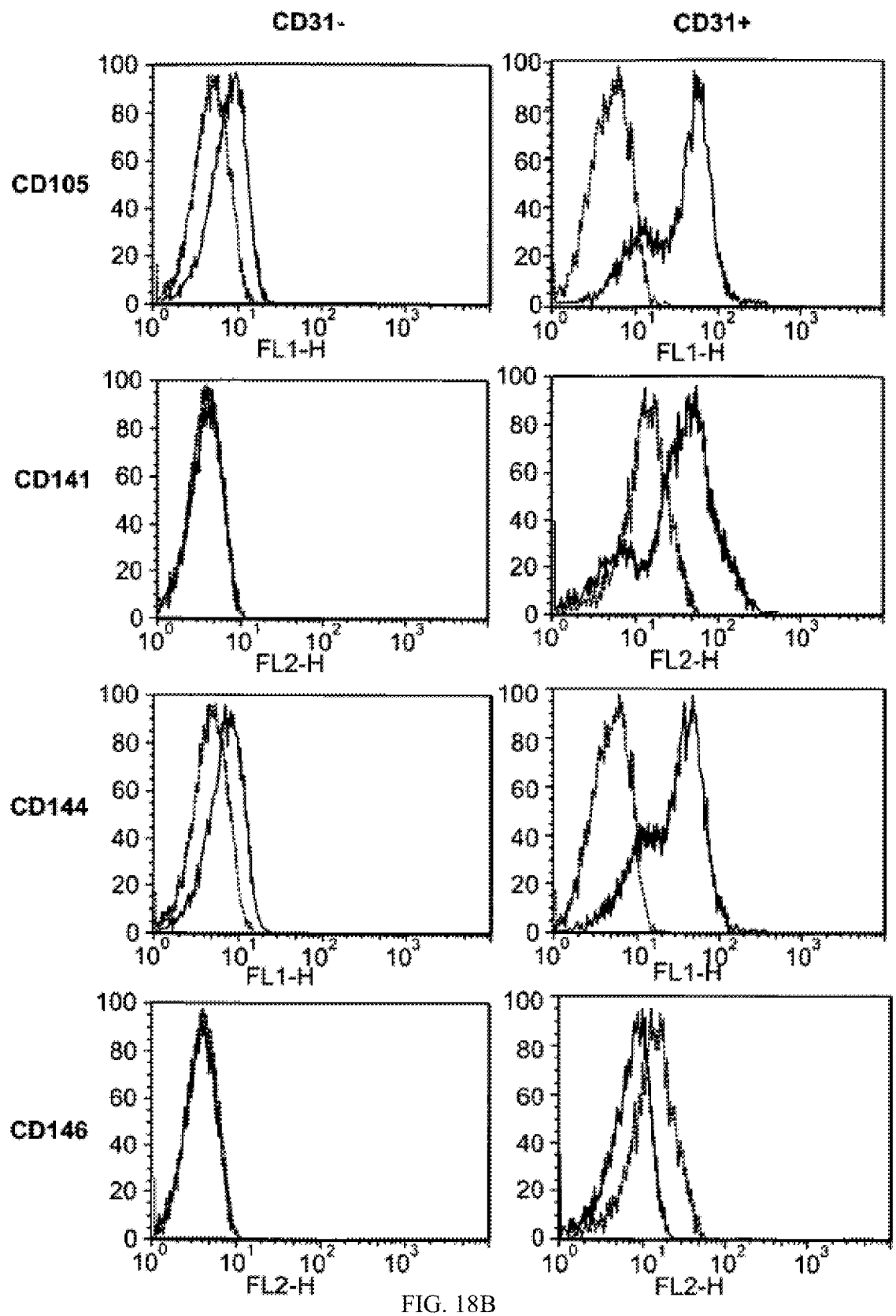
FIG. 18B shows CD105, CD141, CD144, CD146 or isotype controls. Lines, control Ig; line, specific Ab.
Figures 19A, 19B, 19C, 19D:
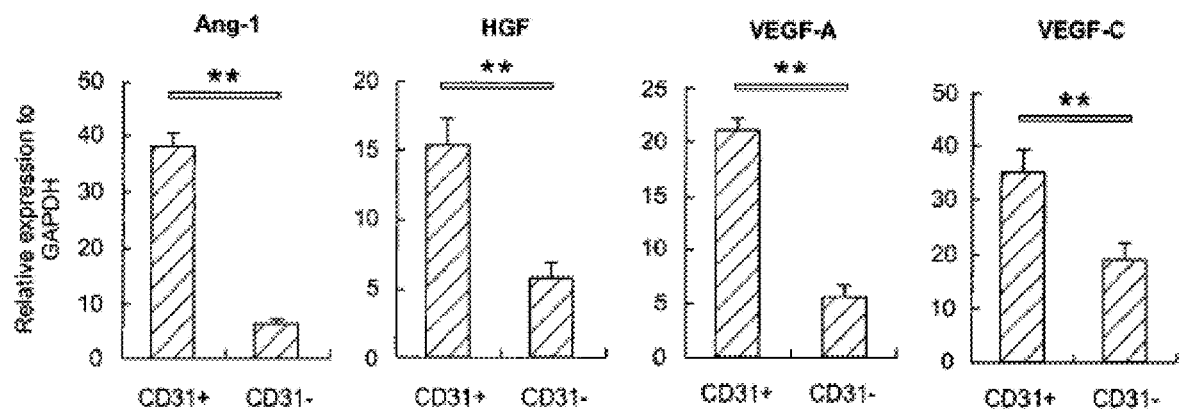
FIG. 19A shows the results of real time PCR analysis of specific endothelial and inflammatory genes in CD31$^+$ and CD31$^−$ cells for Ang-1.
FIG. 19B shows HGF.
FIG. 19C shows VEGF-A.
FIG. 19D shows VEGF-C.
Figures 19E, 19F, 19G, 19H:
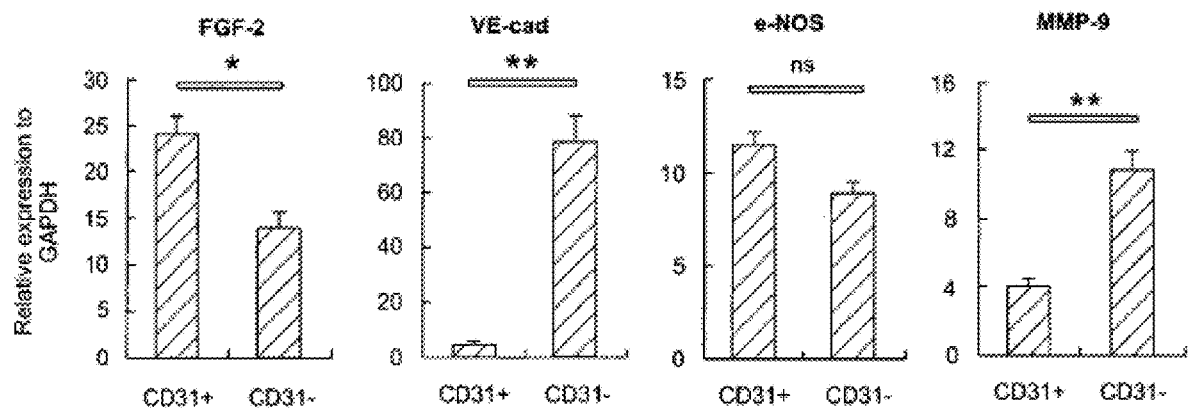
FIG. 19E shows FGF-2.
FIG. 19F shows VE-cad.
FIG. 19G shows e-NOS.
FIG. 19H shows MMP-9.
Figures 19I, 19J:
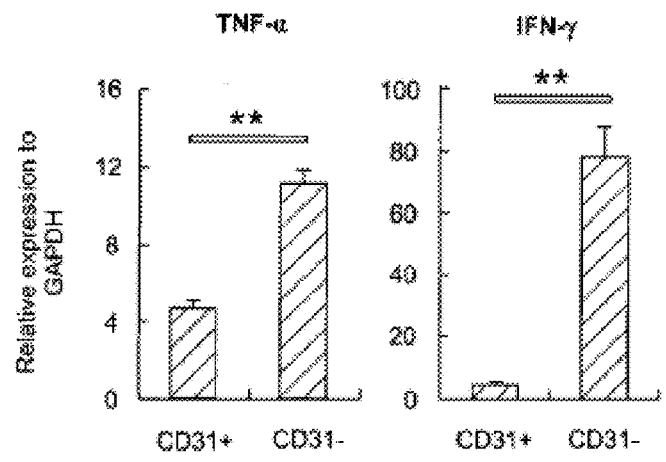
FIG. 19I shows TNF-alpha.
FIG. 19J shows IFN.

To evaluate the surface marker phenotype of CD31+ and CD31− cells, cells were labeled for 20 minutes at manufacture-recommended concentrations with fluorescent antibodies: monocyte/macrophage markers (anti-CD11b-PE, anti-CD 14-PE), hematopoietic lineage maker (anti-CD45-FITC) and endothelial cell markers (anti-CD141-PE, anti-CD105-PE, anti-CD144-FITC and anti-CD146-PE). As a negative control, fluorescent isotype-matched antibodies were used. Cells were rinsed, paraformaldehyde-fixed, and analysis was performed by FACS-Calibur Instrument (Becton-Dickins).

hCD31+ (human CD31+) cells were isolated using a magnetic bead separation technique. To define the phenotype of hCD31+ cells, Fluorescence-activated cell sorting (FACS; BD bioscience) analysis was performed. FACS analysis demonstrated that greater than 40% of the cells include monocyte/macrophage markers (CD11b, CD14), and endothelial cell markers (CD141, CD105, and CD144), but not CD146 (FIGS. 18A and 18B). In addition, more than 98% of hCD31+ cells are positive for CD45, suggesting that hCD31+ cells are not circulating endothelial cells (FIG. 18A). In contrast, hCD31− cells expressed low levels of CD105 and CD144. HSC markers such as CD34, CD133, KDR, Tie-2 were not present on either hCD31+ or hCD31− cells.

Example 20

Real Time PCR-Evaluation of Endothelial and Inflammatory Genes in Human CD31+ and CD31− Cells Real time PCR analysis of specific endothelial and inflammatory genes in CD31+ and CD31 cells was performed.

Quantitative Real-Time PCR Assay

Total RNA was isolated from peripheral blood CD31+ cells and CD31− cells by the use of RNA-stat (Iso-Tex Diagnostics) according to the manufacture's instructions. Subsequently, extracted RNA was reverse-transcribed by use of Taqman Reverse Transcription Reagents (Applied Biosystems) for cDNA synthesis. For real-time reverse transcription-polymerase chain reaction (RT-PCR), human-specific primers and probes, respectively (see supplemental table 1) were used. Quantitative assessment of RNA levels were performed by use of an ABI PRISM 7000 Sequence Detection System. The relative expression value of target, normalized to the endogenous control GAPDH (house-keeping) gene and relative to a calibrator, is expressed as the fomular Rel Exp=$2^{-\Delta CT}$ (fold difference), where $\Delta Ct$=(Ct of target genes)−(Ct of endogenous control gene, GAPDH) in experimental samples. The number of PCR cycles was measured using Lightcycler 3.5 software.

To investigate the expression of multiple angiogenic and inflammantory genes from the hCD31+ population, we measured mRNA levels using real-time PCR. The expression levels of Angiopoietin-1, HGF, VE-Cadherin VEGF-A, interferon-γ and TNF-α significantly increased in the hCD31+ group compared to the hCD3 group.

CD31+ cells are highly enriched with mRNA for endothelial genes, but have a decreased level of mRNA for inflammatory genes, as compared with CD31− cells. Equivalent amounts of RNA were used for gene comparisons. All of the assays were performed in triplicate. (the CD31+ cells of 3 donors were pooled). Data are Mean±SEM. *$P<0.05$, **$P<0.01$ vs. CD31−.

Example 21

Characteristics of EPC and Functional Analysis of Human Peripheral Blood CD31 Derived Cells.

Figure 20A:
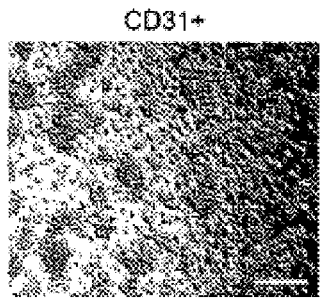
FIG. 20A shows the characteristics of EPC and functional analysis of peripheral blood CD31+ derived cells.
Figure 20B:
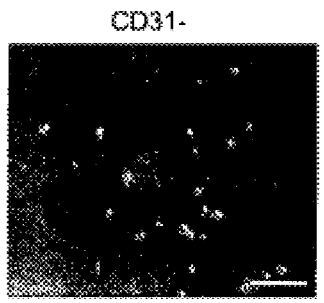
FIG. 20B shows CD31 negative cells.
Figure 20C:
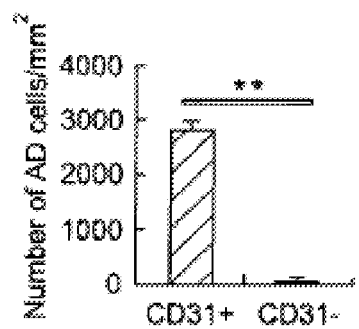
FIG. 20C shows comparison of numbers of adherent (AD) cells and colonies between CD31+ and CD31− cells.
Figure 20D:
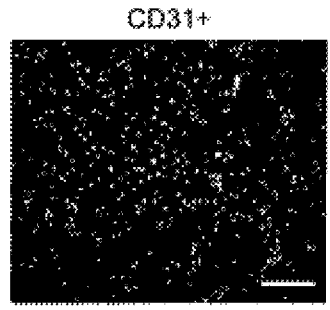
FIG. 20D shows CD positive cells in EPC culture assay.
Figure 20E:
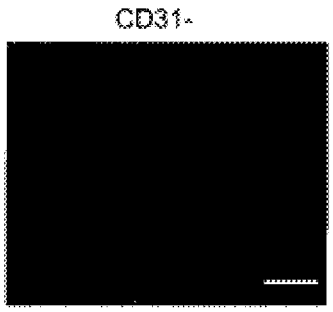
FIG. 20E shows CD negative cells.
Figure 20F:
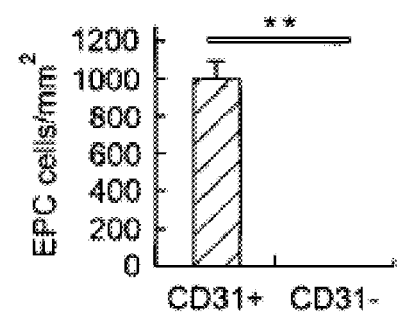
FIG. 20F shows a graph.
Figure 20G:
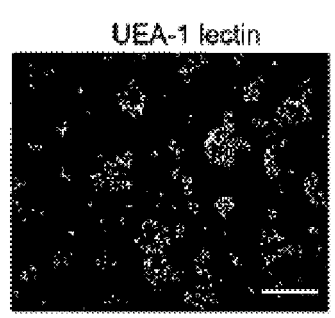
FIG. 20G shows a colony-forming EPCs assay for UEA Lectin.
Figure 20H:
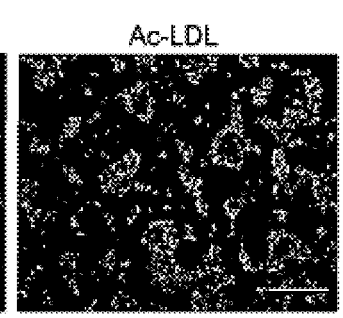
FIG. 20H shows Ac-LDL.
Figure 20I:
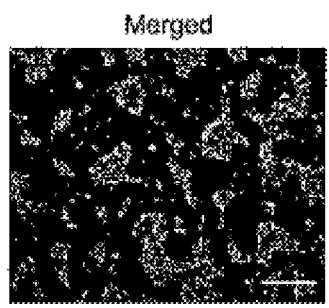
FIG. 20I shows merged.
Figure 20J:
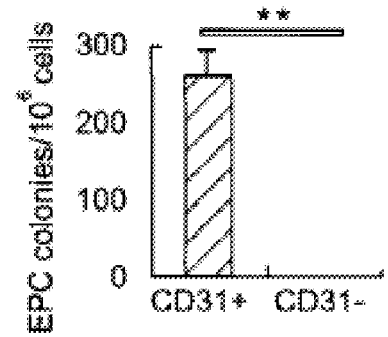
FIG. 20J shows the counts of double-positive colonies grown from CD31+ and CD31− group, respectively (n=3; **P<0.01).
Figures 20K, 20L, 20M, 20N:
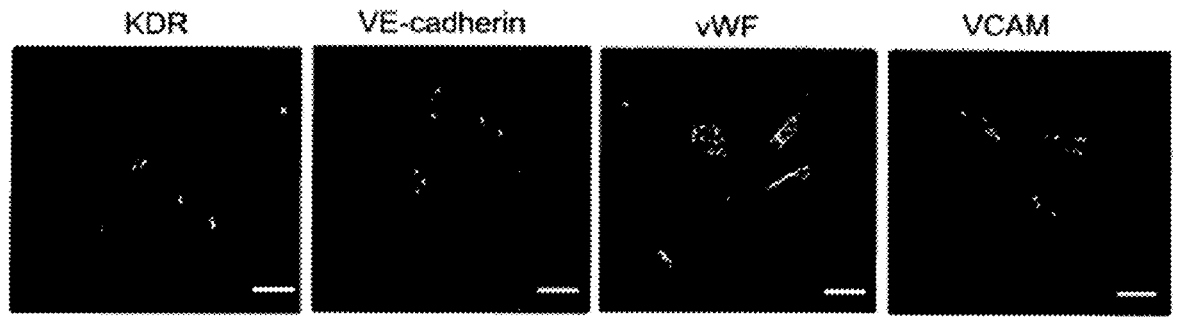
FIG. 20K shows in vitro differentiation of CD31+ cells into endothelial cells for KDR.
FIG. 20L shows VE-cadherin.
FIG. 20M shows vWF.
FIG. 20N shows VCAM.
Figures 20O, 20P, 20Q, 20R:
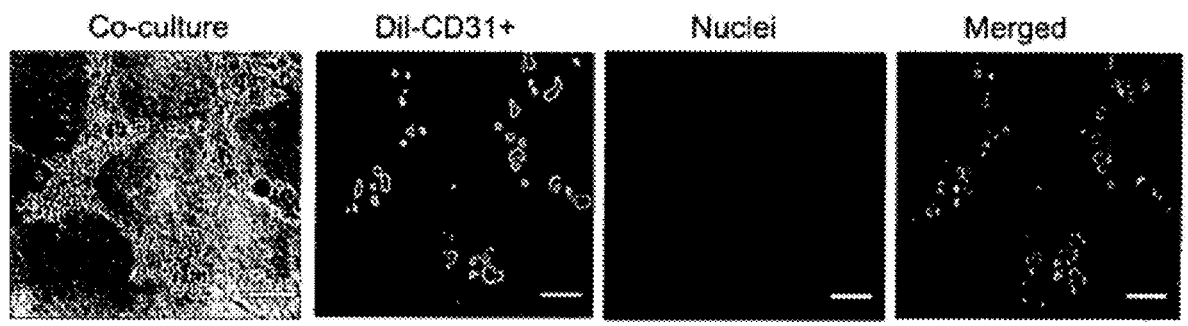
FIG. 20O shows incorporation of CD31+ cells into the HUVEC network co-culture.
FIG. 20P shows DiI-CD31 positive.
FIG. 20Q shows nuclei.
FIG. 20R shows merged.

EPCs were characterized and a functional analysis of peripheral blood CD31 derived cells was performed (FIG. 20A to 20B). The number of adherent (AD) cells and colonies in CD31+ and CD31− cells was compared. Phase-contrast images show significantly greater numbers of adherent cells and colonies in CD31+ cells derived from equivalent numbers of cells examined at 7 days of culture. (n=5, $P<0.01$). An EPC culture assay was performed. FIGS. 20D to 20E shows CD31+ cells were cultured for 4 days then identified as adherent cells double positive for DiI-acLDL uptake and UEA-1 lectin binding. FIG. 20D shows that the CD31+ group demonstrated a significantly greater number of EPC cells compared with CD31− group (n=4, $P<0.01$). FIGS. 20G to 20I shows results of a colony-forming EPC assay that was performed. Colony-forming EPCs were evaluated by performing an endothelial cell differentiation culture with CD31+ or CD31− cells. The upper and lower panel shows a typical colony of EPCs double positive for DiI-acLDL uptake and isolectin B4-FITC binding, appearing on merged images. In FIG. 20F, the right panel shows the counts of double-positive colonies grown from CD31+ and CD31− group, respectively (n=3; **$P<0.01$). FIGS. 20K to 20N in vitro differentiation of CD31+ cells into endothelial cells was examined. Immunofluorescent imaging demonstrated that CD31+ cells expressed EC-specific proteins, such as vWF, VE-cadherin, KDR and CD31. Nuclei were counterstained with DAPI. FIGS. 20O to 20R show the incorporation of CD31+ cells into the HUVEC network was determined. DiI-labeled attaching CD31+ cells were incorporated into the non-labeled HUVEC network on basement matrix gel at 24 hours of coculture.

Colony Forming Unit-Fibroblast (CFU-F) Assay

To evaluate the potential of EPC colony formation, 5×10^6 MACS sorted CD31+ or CD31− cells were cultured in a 6-well plate for 4 days. Cells were incubated with DiI-acLDL (1:500, Biomedical Technologies) for 1 h, then washed with PBS, fixed in 1% paraformaldehyde, and stained with UEA-1 lectin (1:200, sigma). DiI-acLDL uptake and UEA-1 lectin binding double positive cell colonies were counted. CD31+ cells and CD31− cells were cultured in 2-well glass slides at 5×10^6 cells per well and medium was changed between 7 and 10 days. Aggregates of 30 cells or more were scored as CFU-F.

In Vitro Endothelial Cells Differentiation

To induce endothelial lineage differentiation, total hCD31+ cells were cultivated in plastic dishes in DMEM with low (1g) glucose containing 15% of FBS for 2 weeks, supplemented with 25 ng/ml HGF, EGF, FGF, VEGF, IGF-1 and ascorbic acid.

fEndothelial Network Formation on Matrix Gel Culture
Endothelial Network Formation on Matrix Gel Culture After 7 day of culture, peripheral blood CD31$^+$ adherent cells were obtained from culture plates. CD31$^+$ cells were then labeled with DiI and cocultured with unlabeled human umbilical vein endothelial cells (HUVECs) on basement membrane matrix gel (Matrigel™, Becton, Dickinson) at a 1:10 ratio. After 24 hours of incubation, endothelial network formation and incorporation of red fluorescent-labeled CD31$^+$ cells into endothelial networks were examined and representative fields were photographed under fluorescence microscopy.

When human peripheral blood derived hCD31$^+$ cells (n=7) were cultured on plastic dishes, a number of adherent cell and colonies appeared after 4 day of culture. Much greater numbers of adherent cells and colonies developed from hCD31$^+$ (n=7) than from the same amount of hCD3F cells (n=7; P<0.01) (FIGS. 20A to 20B and 20C). We first hypothesized that the majority of isolated hCD31$^+$ cells contain primitive EPCs. To identify whether hCD31$^+$ cells contain primitive EPCs, we used equal numbers of hCD31$^+$ and hCD31$^-$ cells from human peripheral blood, then performed EPC and EPC colony culture assays. The EPCs and EPC colonies were identified by double staining for DiI-acLDL uptake and UEA1-FITC binding (FIGS. 20D to 20J). Significantly greater number of EPC and EPC colonies were generated from the hCD31$^+$ cell population compared with hCD31$^-$ cells population(n=7; P<0.01).

Human peripheral blood hCD31$^+$ cells were isolated (purity 95%-98%) and cultivated under endothelial conditions. To induce endothelial lineage differentiation, total hCD31$^+$ cells were cultivated in plastic dishes in DMEM with low (1 g) glucose containing 15% of FBS, supplemented with 25 ng/ml HGF, EGF, FGF, VEGF, IGF-1 and ascorbic acid. To determine if endothelial cell differentiation had occurred, the expression of a selected set of markers was characterized by flow cytometry after 10-15 days serial culture. Immunofluorescencent cytochemistry assays revealed that hCD31$^+$ cells exhibited the endothelial cell markers such as Ve-Cadherin, KDR, vWF, CD31 fourteen days after culture. (FIGS. 20K to 20N).

The angiovasculogenic function of hCD31$^+$ cells cultivated under endothelial conditions in vitro was examined. To investigate whether hCD31$^+$ cells participated in endothelial network formation, matrigel tube formation assays were performed. hCD31$^+$ cells were collected at day 14 of culture, labeled with the red fluorescent dye CM-DiI (DiI), and co-cultured with HUVECs on basement membrane matrix gel. At 24 hours of co-culture, hCD31$^+$ cells incorporated with HUVEC networks (FIGS. 20 O to 20 R).

Example 22

In Vitro Differentiation of Human CD31+ Cells into Vascular-Like Tube after 4 Weeks in EPC Culture Condition The differentiation of CD31+ cells into vascular tubes was observed.
In Vitro Endothelial Cells Differentiation To induce endothelial lineage differentiation, total hCD31$^+$ cells were cultivated in plastic dishes in DMEM with low (1 g) glucose containing 15% of FBS for 2 weeks, supplemented with 25 ng/ml HGF, EGF, FGF, VEGF, IGF-1 and ascorbic acid.

Cells were incubated with DiI-acLDL (1:500, Biomedical Technologies) for 1 h, then washed with PBS, fixed in 1% paraformaldehyde, and stained with UEA-1 lectin (1:200, sigma) and DAPI (1:5000).

Figure 21:
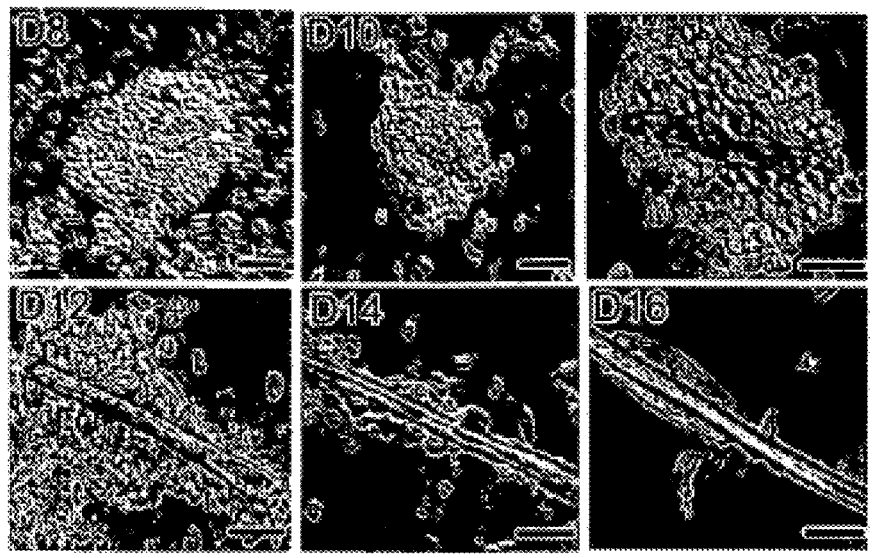
FIG. 21 shows in vitro differentiation of $CD31^+$ cells into vascular-like tubes after 4 weeks in EPC culture condition. Sequential change of differentiated CD31+ endothelial cells into vascular-like tubes. CD31+ cells are capable of forming capillaries in vitro.
Figure 22A:
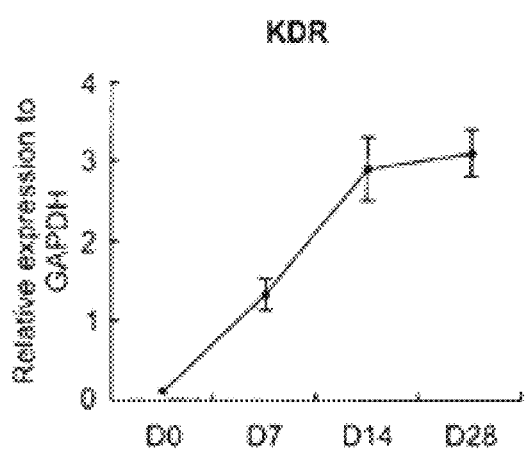
FIG. 22A shows the results of real time PCR analysis of KDR— specific endothelial and inflammatory genesin endothelial cell differentiated CD31+ cells. CD31+ cells were cultured in EPC culture medium for 4 weeks. Non-adherent cells were discarded and only adherent cells were analyzed.
Figure 22B:
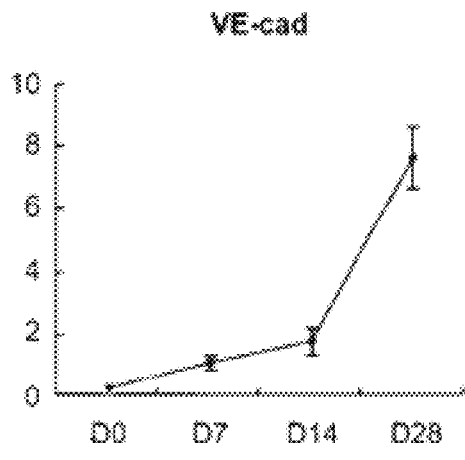
FIG. 22B shows VE-cad.
Figure 22C:
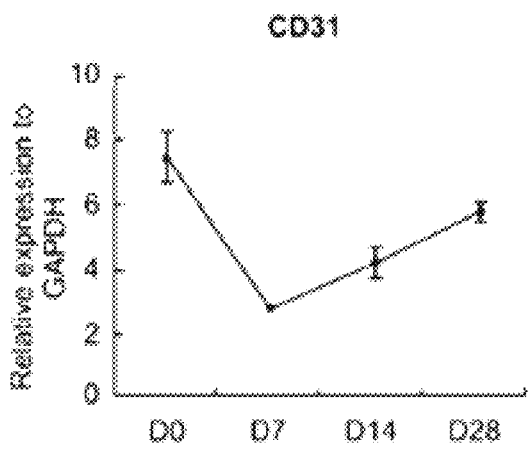
FIG. 22C shows CD31.
Figure 22D:
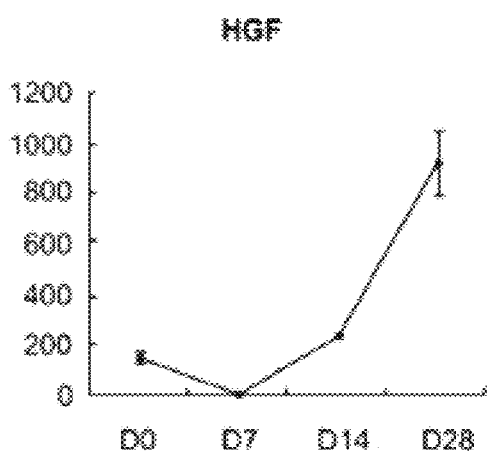
FIG. 22D shows HGF.
Figure 22E:
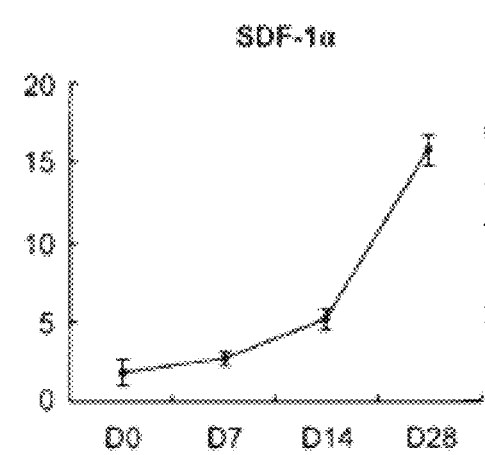
FIG. 22E shows SDF-1alpha.
Figure 22F:
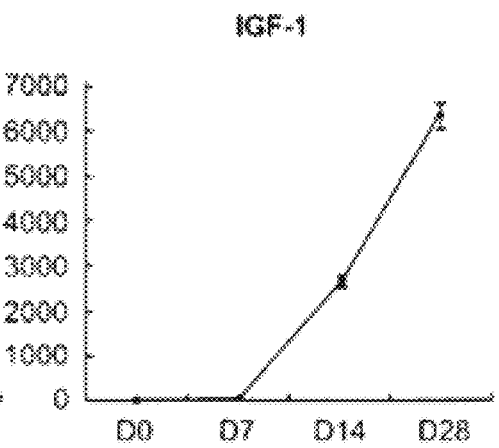
FIG. 22F shows IGF-1.
Figure 22G:
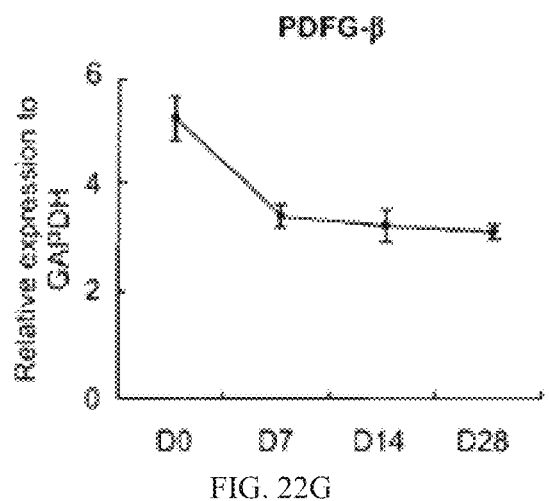
FIG. 22G shows PDFG-beta.
Figure 22H:
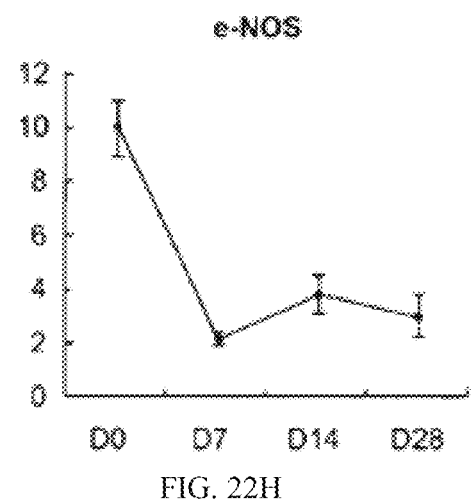
FIG. 22H shows e-NOS.
Figure 22I:
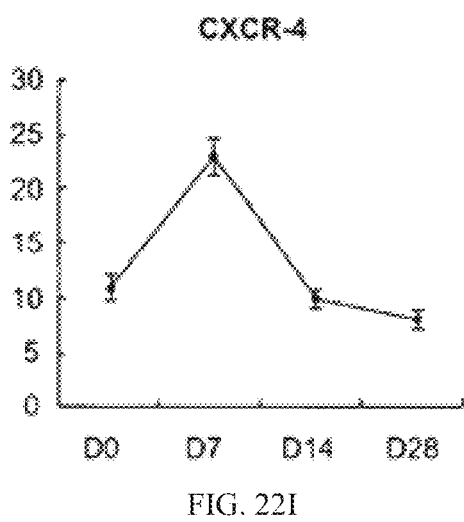
FIG. 22I shows CXCR-4.
Figure 22J:
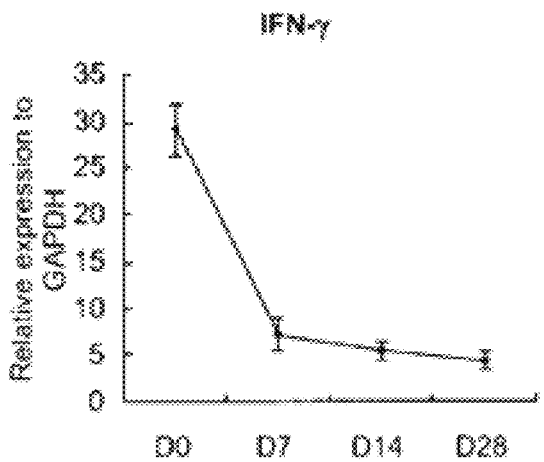
FIG. 22J shows IFN-gamma.
Figure 22K:
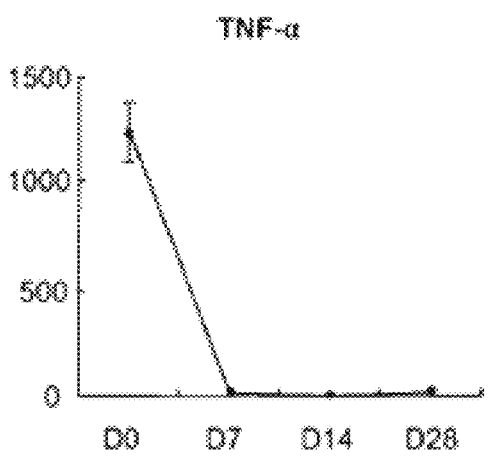
FIG. 22K shows TNF-alpha.
Figure 23A:
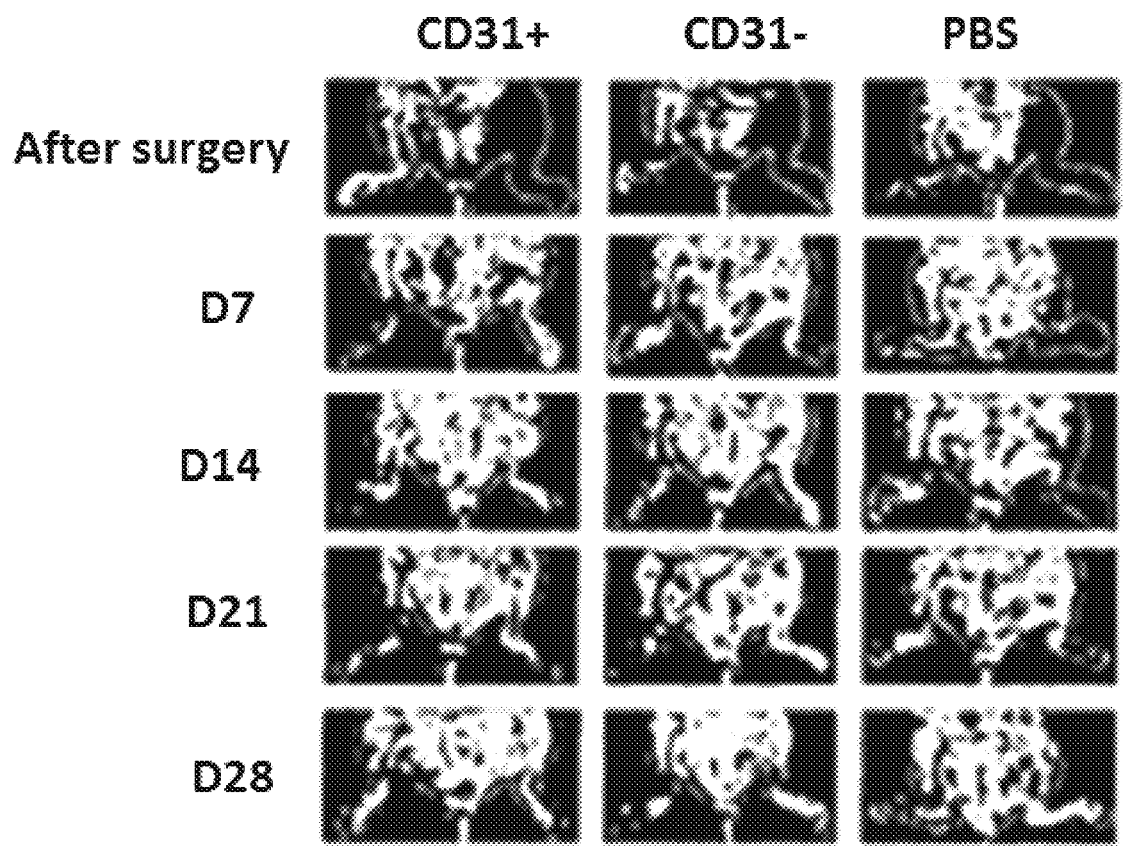
FIG. 23A shows the results of in vivo vasculogenesis of CD31 cells in an ischemic limb of a nude mouse.
Figure 23B:
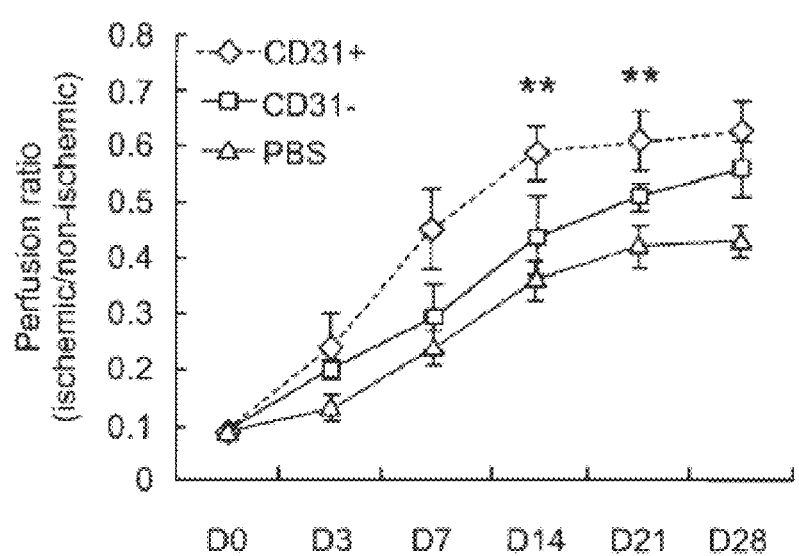
FIG. 23B shows a graph.
Figure 23C:
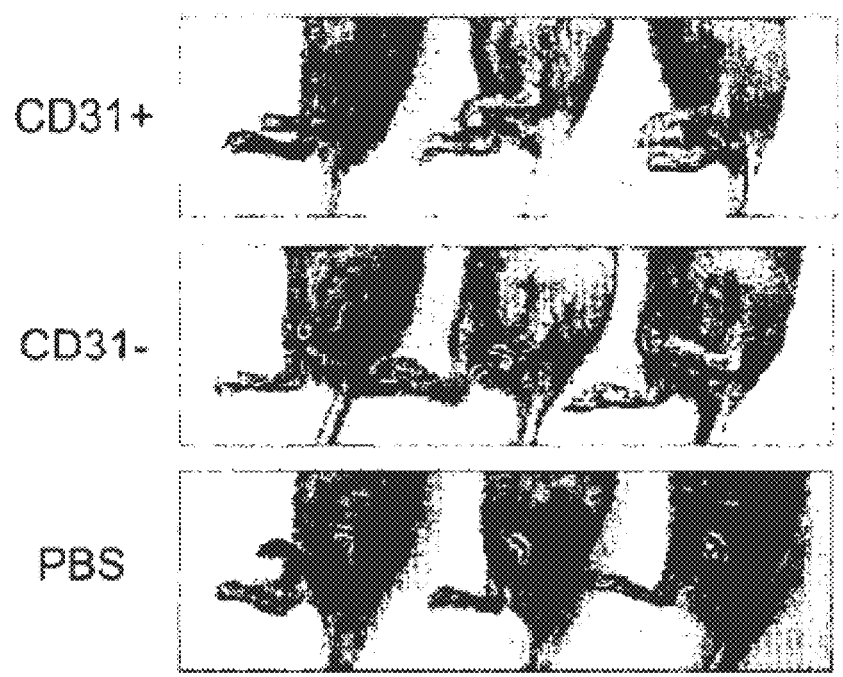
FIG. 23C shows mice.
Figure 23D:
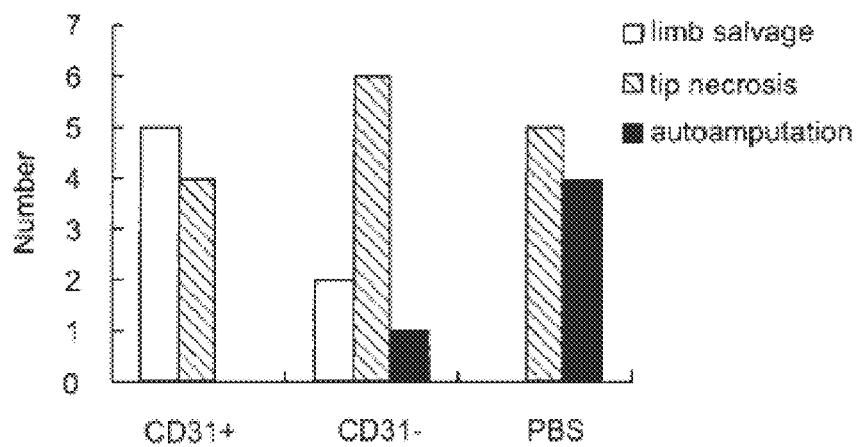
FIG. 23D shows a graph.
Figures 24A, 24B, 24C:
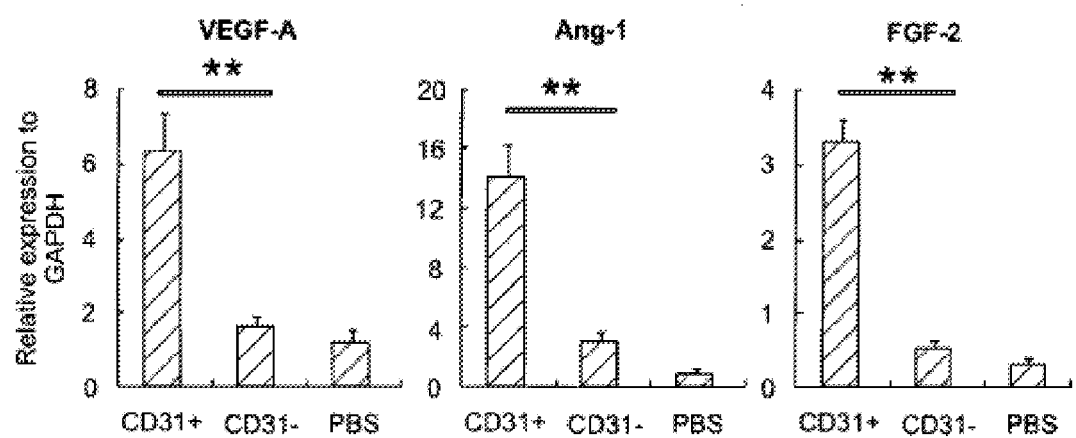
FIG. 24A shows the results of real time PCR analysis of VEGF-A— multiple angiogenic factors following $CD31^+$ transplantation into the ischemic hindlimb of athymic nude mice.
FIG. 24B shows Ang-1.
FIG. 24C shows FGF-2.
Figures 24D, 24E, 24F:
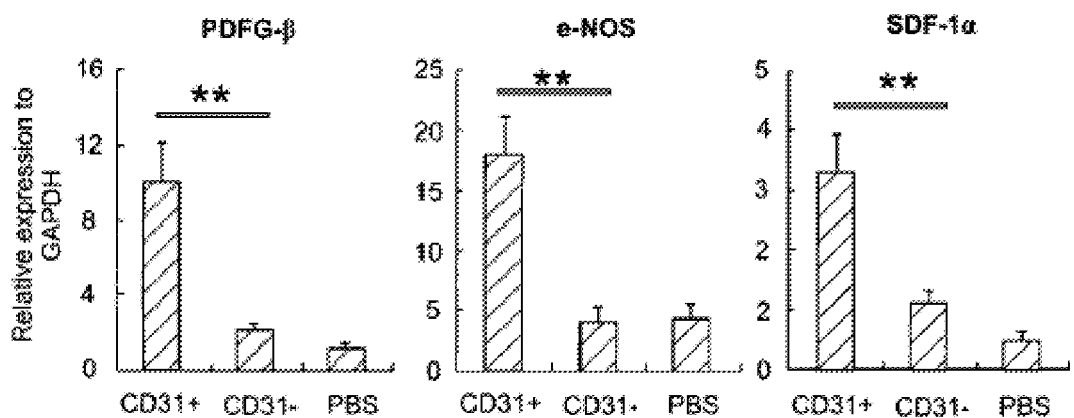
FIG. 24D shows PDFG-beta.
FIG. 24E shows e-NOS.
FIG. 24F shows SDF-1alpha.
Figure 25A:
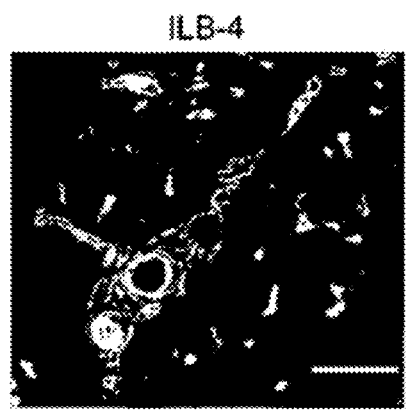
FIG. 25A shows transdifferentiation of CD31+ cells into endothelial cells. Immunofluorescence staining images shows that human peripheral blood CD31 cells are transdifferentiated into endothelial cells lineage. Tissue sections are from hind limb harvested at 2 weeks from animals with hindlimb ischemia followed by the intramuscular injection of DiI-labeled CD31 cells. Sections were stained for ILB-4 which is endothelial cell marker. For nuclei detection, DAPI was counterstained. Bar: 50 um.
Figure 25B:
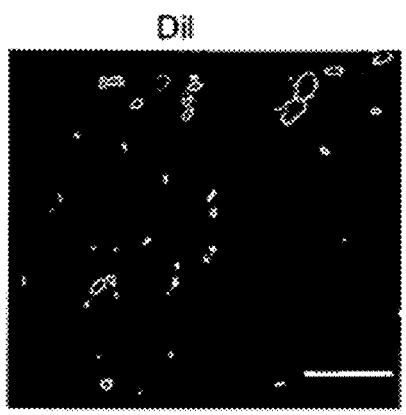
FIG. 25B shows DiI.
Figure 25C:
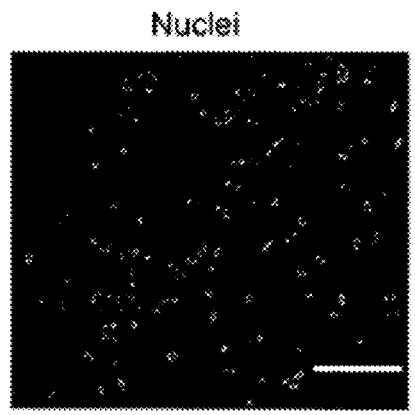
FIG. 25C shows Nuclei.
Figure 25D:
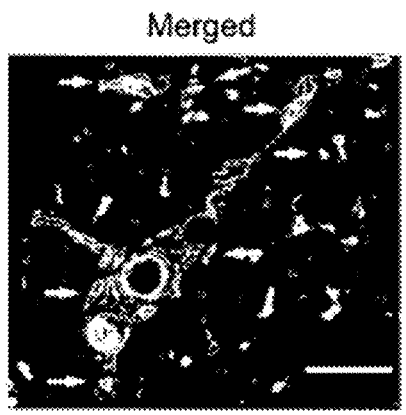
FIG. 25D shows the "merged" panel shows cells double positive for DiI and ILB-4 binding, appearing on merged images.

CD31+ cells formed vascular-like tubes after 4 weeks in EPC culture condition (FIG. 21). CD31+ cells changed sequentially into vascular-like tubes. CD31$^+$ cells are capable of forming capillaries in vitro.

The cells of the vascular-like tube were identified by double staining for DiI-acLDL uptake and UEA1-FITC binding. Immunohistochemistry of CD31$^+$ cell-derived vascular-like tubes shows that they expressed UEA-1 lectin and incorporated DiI-Ac-LDL like tubes grown from endothelial cell lines. Nuclei counterstained with DAPI in blue.

Example 23

Real Time PCR of Specific Endothelial and Inflammatory Genes in Endothelial Cell Differentiated CD31$^+$ Cells Real time PCR of specific endothelial and inflammatory genes was performed in endothelial cell differentiated CD31$^+$ cells.

CD31+ cells were cultured in EPC culture medium for 4 weeks. Non-adherent cells were discarded and only adherent cells were analyzed. Equivalent amounts of RNA were used for all gene comparisons. All of the assays were performed in triplicate.

Total CD31$^+$ cells were cultivated in plastic dishes in DMEM with low (1 g) glucose containing 15% FBS for 4 weeks, supplemented with 25 ng/ml HGF, EGF, FGF, VEGF, IGF-1 and ascorbic acid. All samples were collected every week. RNA was isolated with RNA-stat (Iso-Tex Diagnostics) according to the manufacture's instructions. Subsequently, extracted RNA was reverse-transcribed by use of Taqman Reverse Transcription Reagents (Applied Biosystems) for cDNA synthesis. For real-time reverse transcription-polymerase chain reaction (RT-PCR), we used human-specific primers and probes, respectively (see supplemental table 1). Quantitative assessment of RNA levels was performed by use of an ABI PRISM 7000 Sequence Detection System. The relative expression value of target, normalized to the endogenous control GAPDH (house-keeping) gene and relative to a calibrator, is expressed as the fomular Rel Exp=$2^{-\Delta CT}$ (fold difference), where $\Delta Ct$=(Ct of target genes)−(Ct of endogenous control gene, GAPDH) in experimental samples. The number of PCR cycles was measured using Lightcycler 3.5 software.

Human peripheral blood hCD31$^+$ cells were isolated (purity 95%-98%) and cultivated under endothelial conditions. To induce endothelial lineage differentiation, total hCD31$^+$ cells were cultivated in plastic dishes in DMEM with low (1 g) glucose containing 15% of FBS, supplemented with 25 ng/ml HGF, EGF, FGF, VEGF, IGF-1 and ascorbic acid. Endothelial cell differentiation was analyzed by characterizing the expression of a selected set of markers by real-time PCR after 4 weeks of serial culture (FIG. 22A to 22F, and FIG. 22G to 22K). Endothelial-like cells derived from CD31 cells become positive for SDF-1α, IGF-1 and negative for TNF-α, IFN-γ during differentiation.

Example 24

In Vivo Vasculogenesis of Human CD31 Cells in Ischemic Limb of Nude Mouse

The in vivo vasculogenesis of CD31+ cells in an ischemic limb of a nude mouse was determined. All experimental protocols were approved by Caritas St. Elizabeth's Institutional Animal Care and Use Committee (IACUC). Female athymic nude mice (Charles River Laboratories), 6 to 9 weeks old and 18 to 22 g in weight were used. To induce a hindlimb ischema model, mouse were anesthetized with 120 mg/kg intraperitoneal pentobarbital for operative resection of one femoral artery. Surgery to create hindlimb ischemia was completed by resecting the right femoral arteries. Mice were transplanted with DiI-labeled CD31$^+$, CD31$^-$ cells in EBM medium or PBS intramuscularly into the ischemic hindlimb area after surgery (n=9 for each implantation). To measure serial blood flow in hindlimb for the 4 weeks after operation, Laser Doppler perfusion image analyzer (Moor Instrument, Wilmington, Del.) was used. After 28 days mice in each group were sacrificed.

Therapeutic Effects of Human CD31+ Cells

To investigate the therapeutic potential of CD31$^+$ cells hindlimb ischemia was surgically induced in athymic nude mice. hCD31$^+$(human CD31$^+$) cells, hCD31$^-$ (human CD31$^-$) cells and PBS were injected into the ischemic hindlimbs (n=9, each). The results are presented in FIGS. 23A-23D.

The hCD31$^+$ treated group showed higher limb salvage rate than other groups [total salvage/tip necrosis/amputation; hCD31$^+$ cells 5/4/0, hCD31$^-$ cells 2/5/2, PBS control 0/5/4] (n=9 each group).

LDPI analysis revealed that a greater degree of blood perfusion was observed in the ischemic limb of hCD31$^+$ cells injected mice (59% increase at day 21, P 0.001) compared with hCD31− cell or PBS transplanted control mice on days 7 and 14. Capillary densities were also measured in tissue sections collected at day 14 from the lower abductor of ischemic hindlimb. The overall capillary density of the hCD31$^+$ treated group was also significantly higher than hCD31$^+$ and PBS treated groups. These data suggest implantation of CD31$^+$ cells not only prevents adverse vascular remodeling, but shows angio-vasculogenic potential in vivo.

Example 25

Expression of Angiogenic Factors Following CD31+ Transplantation

The expression of angiogenic factors following CD31+ transplantation was determined as follows.
Quantitative Real-Time PCR Assay Total RNA was isolated from each of CD31$^+$, CD31$^-$ and PBS injected hind-limb tissues after 7 days by the use of RNA-stat (Iso-Tex Diagnostics) according to the manufacture's instructions. Subsequently, extracted RNA was reverse-transcribed with Taqman Reverse Transcription Reagents (Applied Biosystems) for cDNA synthesis. For real-time reverse transcription-polymerase chain reaction (RT-PCR), human-specific primers and probes, respectively (see supplemental table 1) were used. Quantitative assessment of RNA levels were performed by use of an ABI PRISM 7000 Sequence Detection System. The relative expression value of target, normalized to the endogenous control GAPDH (house-keeping) gene and relative to a calibrator, is expressed as the fomular Rel Exp=$2^{-\Delta CT}$ (fold difference), where $\Delta Ct$=(Ct of target genes)−(Ct of endogenous control gene, GAPDH) in experimental samples. The number of PCR cycles was measured using Lightcycler 3.5 software.

Multiple Angiogenic Factors are Upregulated after CD31$^+$ Cells Transplantation To determine the level of expression of various cytokines following cell transplantation into the ischemic hindlimb of athymic nude mice, mice were sacrificed and hindlimb tissues were collected. The expression levels of VEGF-A, FGF-2 (bFGF), Angiopoitin-1, PDGF and e-NOS were significantly increased in the CD31$^+$ cell injected group compared to CD31$^-$ cells and PBS injected group (FIG. 24A to 24F). Overall, the expression of multiple angiogenic, chemoattractant cytokines was greater in the hindlimb of CD31$^+$ injected group compared to CD31$^-$ and PBS injected groups. However, the expressions of inflammatory genes such as IL-1,6,10 and IFN-γ revealed no difference among these three groups (FIG. 24G to 24K).

Example 26

Transdifferentiation of Human CD31+ Cells into Endothelial Cells

The transdifferentiation of CD31+ cells into endothelial cells was analyzed as follows.
Histological Analysis Mice were killed 2 weeks after cells transplantation. For capillary density measurement, four frozen sections of ischemic tissue from the adductor and semimembranous muscles from each group were stained with primary biotinlated isolectin B4 and secondary strepta-avidin Alexafluor 488 (Invitrogen). Five fields from four tissue sections were randomly selected, and the number of capillaries was counted in each field. Pictures were photographed using a fluorescent inverted microscopy or a confocal microscopy. Ten mice were used to define whether administered CD31$^+$ or CD31$^-$ cells differentiated into endothelial cells.
Transdifferentiation of hCD31$^+$ Cells into Endothelial Cells To define the transdifferentiation potential of hCD31$^+$ cells in HLI mice, 1×10$^6$ DiI-labeled hCD31$^+$ cells were transplanted intramuscularly into the ischemic hindlimb of nude mice. Histologic analysis demonstrated that a fraction of injected DiI-labeled hCD31$^+$ cells exhibit endothelial phenotypes during the follow-up period of 2-8 weeks.

FIGS. 25A-D present the results of immunofluorescence analysis of replicate samples of CD31$^+$ cells. Immunofluorescence staining images show that human peripheral blood CD31$^+$ cells were transdifferentiated into endothelial cells lineage. Tissue sections were from hind limb harvested at 2 weeks from animals with hindlimb ischemia followed by the intramuscular injection of DiI-labeled CD31 cells. Sections were stained for ILB-4 which is endothelial cell marker. For nuclei detection, DAPI was used as a countertain. Bar: 50 um Example 27

Evaluation of Apoptosis in CD31+ and CD31− Cells

Quantitative analysis of TUNEL-positive cells was performed as follows.

Figure 26A:
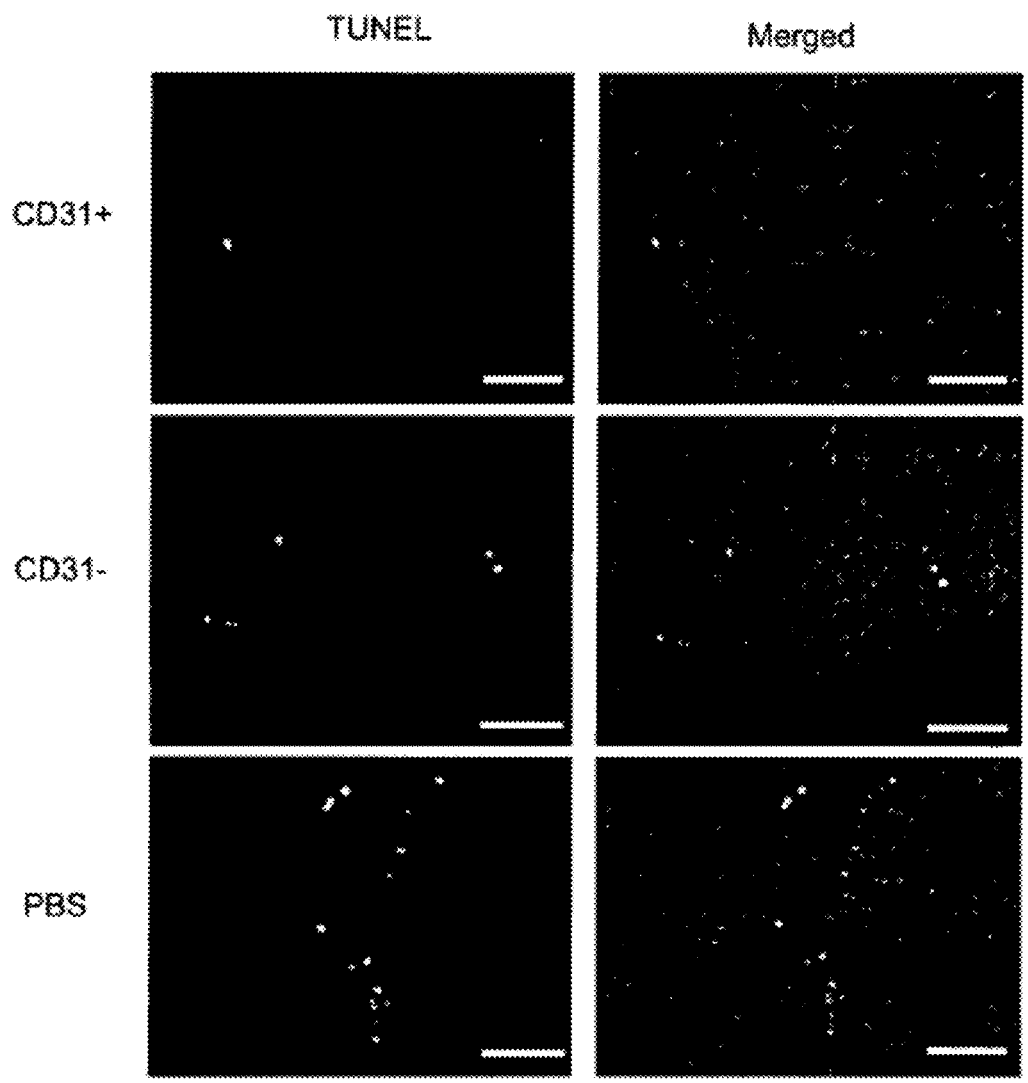
FIG. 26A shows the results of quantitative analysis of TUNEL-positive $CD31^+$ and CD31− cells.
Figure 26B:
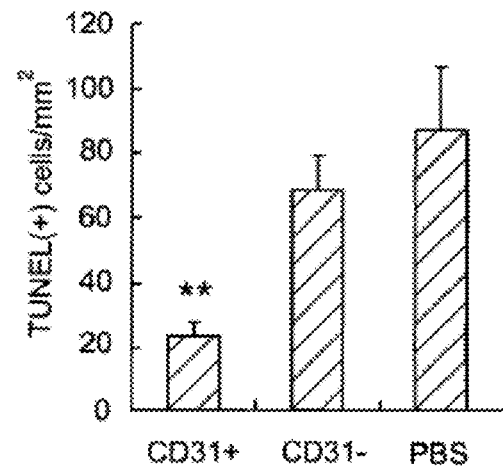
FIG. 26B shows a graph.
Figure 27A:
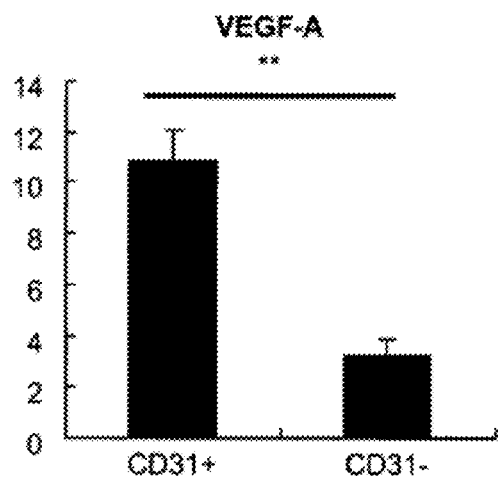
FIG. 27A shows the results of real time PCR analysis of VEGF-A human bone marrow $CD31^+$ cells.
Figure 27B:
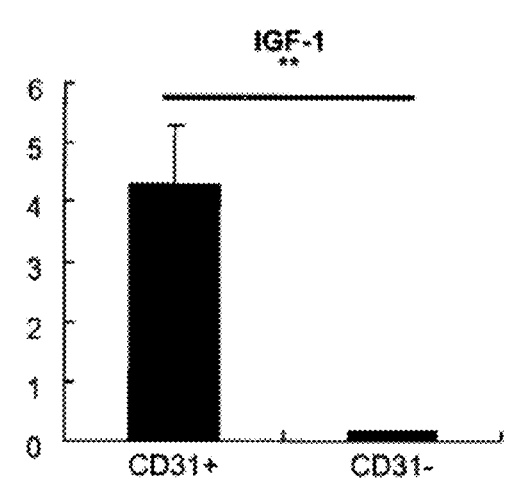
FIG. 27B shows IGF-1.
Figure 27C:
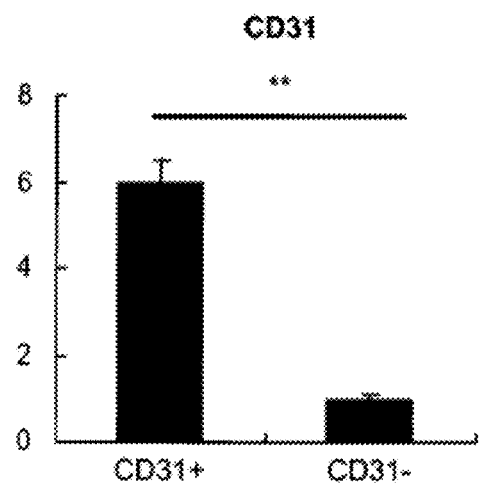
FIG. 27C shows CD31.
Figure 27D:
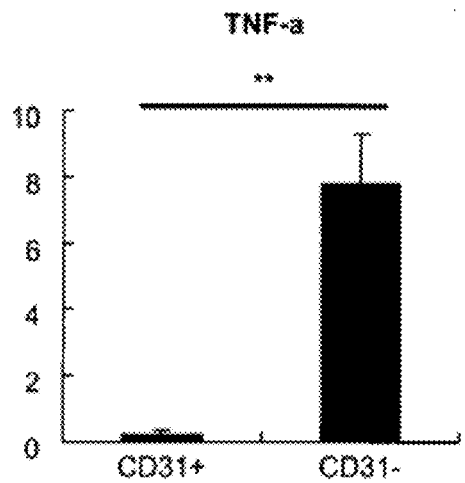
FIG. 27D shows TNF-alpha.
Figure 27E:
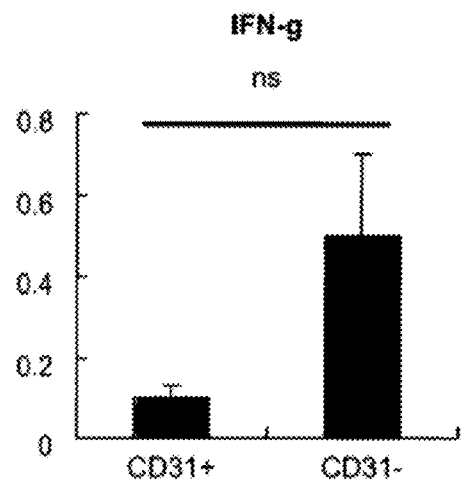
FIG. 27E shows IFN-gama.

To evaluate apoptosis, TdT-mediated dUTP nick-end labeling (TUNEL) reaction was performed by using the fluorescein in situ cell death detection kit (Roche-Molecular).
hCD31$^+$ Cells Transplantation Decreases Apotosis To determine if hCD31$^+$ cell transplantation decreases apoptosis, TUNEL assays with tissue sections harvested from CD31+, CD31− or PBS transplanted hindlimbs at day 7 following transplantation were performed (FIGS. 26A and 26B). The number of TUNEL positive nuclei in the hindlimb ischemia was almost 3 times lower in the CD31$^+$ group than in the PBS group.

Example 29

Real Time PCR Analysis of Human Bone Marrow CD31+ Cells

The expression of multiple angiogenic and inflammatory genes from the bone marrow derived hCD31$^+$ population was investigated as follows.

Total RNA was isolated from human bone marrow derived CD31$^+$ cells and CD31$^-$ cells by the use of RNA-stat (Iso-Tex Diagnostics) according to the manufacture's instructions. Subsequently, extracted RNA was reverse-transcribed by use of Taqman Reverse Transcription Reagents (Applied Biosystems) for cDNA synthesis. For real-time reverse transcription-polymerase chain reaction (RT-PCR), human-specific primers and probes, respectively (see supplemental table 1) were used. Quantitative assessment of RNA levels were performed by use of an ABI PRISM 7000 Sequence Detection System. The relative expression value of a target, normalized to the endogenous control GAPDH (house-keeping) gene and relative to a calibrator, is expressed as the fomular Rel Exp=$2^{-\Delta CT}$ (fold difference), where $\Delta Ct$=(Ct of target genes)-(Ct of endogenous control gene, GAPDH) in experimental samples. The number of PCR cycles was measured using Lightcycler 3.5 software.

To investigate the expression of multiple angiogenic and inflammatory genes from the hCD31$^+$population, mRNA levels were measured using real-time PCR. The expression levels of IGF-1, VEGF-A and CD31 were significantly higher in the CD31+ group and the expression of interferon-$\gamma$ and TNF-$\alpha$ was significantly decreased in the hCD31$^+$ group compared to the hCD31$^-$ group (FIGS. 27A-E).

Example 30

Characterization of BM-Derived Lin– Cells

To determine if BM-derived CD31 expressing cells include multipotent progenitor and stem cells, CD31$^+$ and Lineage-depleted CD31$^+$ (Lin$^-$CD31$^+$) cells were isolated from BM of adult C57BL/6J mice and analyzed for the expression of stem cells markers. Lin$^-$CD31$^+$ cells from mouse BM express very high levels of stem cell markers, including c-kit, Sca1-1 and Flk-1. CD31 expressing subsets, including CD31$^+$, Lin$^-$CD31$^+$ and Lin$^-$CD31$^+$Sca-1$^+$ Lin-CD31+ cells from mouse BM are also highly enriched for hematopoietic clonogenic progenitor cells and can be efficiently expanded when cultured with hematopoietic growth factors. In an in vivo congenic competitive bone marrow transplantation model, lin$^-$CD31$^+$ cells revealed greater potential to repopulate lethally irradiated bone marrow.
BM-Lin$^-$ and -Lin$^-$c-kit$^+$Sca-1$^+$ Cells Express Very High Levels of CD31

Figure 28A:
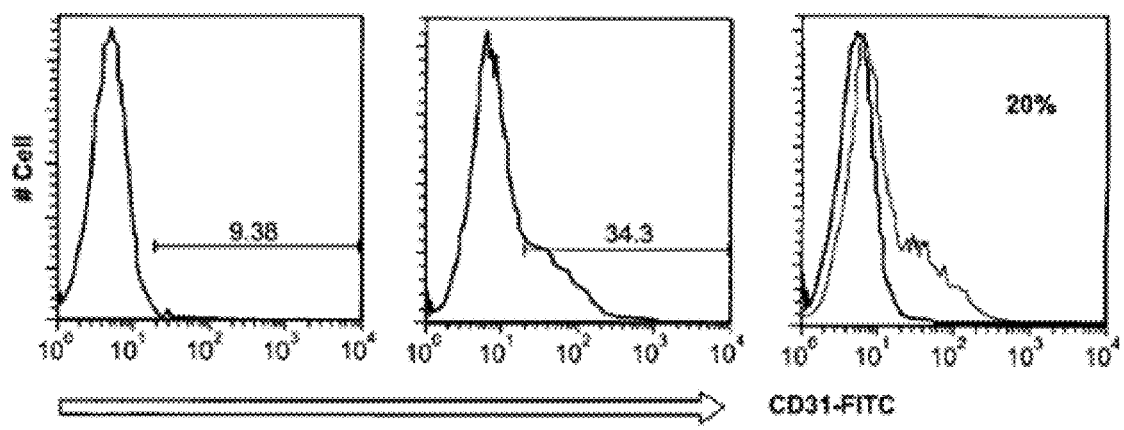
FIG. 28A shows the results of flow cytometry analyses for CD31 expression on BM cells, Lin⁻cells and Lin⁻c-kit+Sca-1+ cells. FACS analysis for CD31 expression on mouse BM cells after red blood cell (RBC) lysis. A line is isotype control. A line is specific mAb.
Figure 28B:
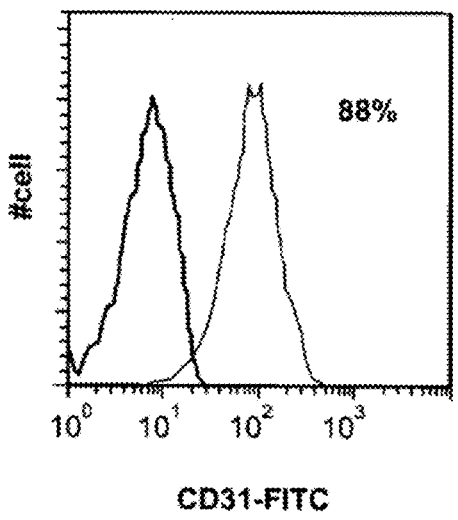
FIG. 28B shows CD31 expression on Lin⁻ cells. A line is isotype control. A line is specific mAbs.
Figure 28C:
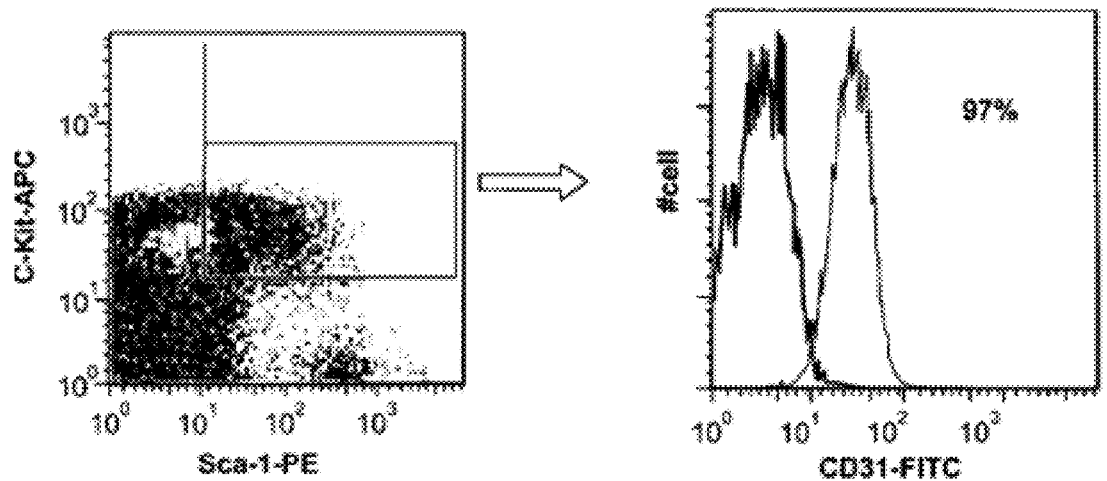
FIG. 28C shows CD31 expression on Lin⁻ c-kit+Sca-1+ cells. A line is isotope control and a line is specific mAb.

BM cells were obtained from BM of C57BL/6J mice and were partially lineage-depleted by staining BM cells with mouse biotinilated lineage mAbs followed by anti-biotin microbeads. Partially depleted Lin$^-$ cells were then incubated with mouse mAbs specific for Sca1-1, c-kit and CD31 and analyzed by flow cytometry (FIGS. 28A-C). These data demonstrate that both Lin$^-$ and Lin$^-$Sca-1$^+$c-kit$^+$ cells express high levels of CD31.

BM-Derived Lin$^-$CD31$^+$ Cells Express Multiple Stem Cell Markers, Such as c-kit, Sca-1 and Flk-1.

Figure 29:
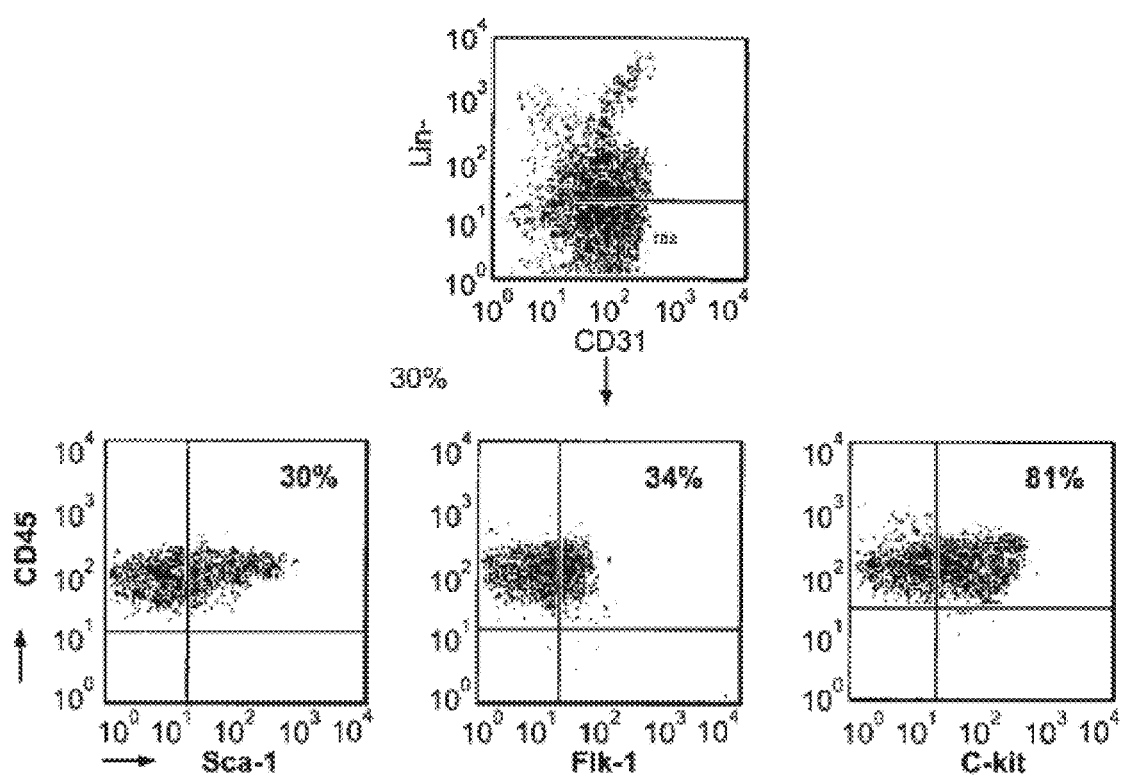
FIG. 29 shows FACS analysis for expression of stem cell markers, including Sca-1, Flk-1 and c-kit. BM cells were partially lineage-depleted by staining of BM cells with mouse biotinalyted lineage mAbs followed by anti-biotin microbeads. Partially depleted Lin⁻ cells were incubated with mouse mAbs, including APC-lineage cocktail, PE-Sca-1, PE-c-kit, PE-Flk-1, FITC-CD31 and CD45, and then analyzed by flow cytometry.

To investigate CD31 as a stem cell marker, BM cells were partially lineage-depleted by staining of BM cells with mouse biotinilated lineage mAbs followed by anti-biotin microbeads. Partially depleted Lin$^-$ cells were incubated with mouse mAbs, including APC-lineage cocktail, PE-Sca1-1, PE-c-kit, PE-Flk-1, FITC-CD31 and CD45, and then analyzed by flow Cytometry (FIG. 29). These data demonstrated that Lin$^-$CD31$^+$ cells express high levels of c-kit, and also Sca1-1 and Flk-1, indicating that Lin$^-$CD31$^+$ cell likely have multipotent stem cell potential.

Example 31

Hematopoietic Clonogenic Potential of CD31 Expressing Cells

Figure 30A:
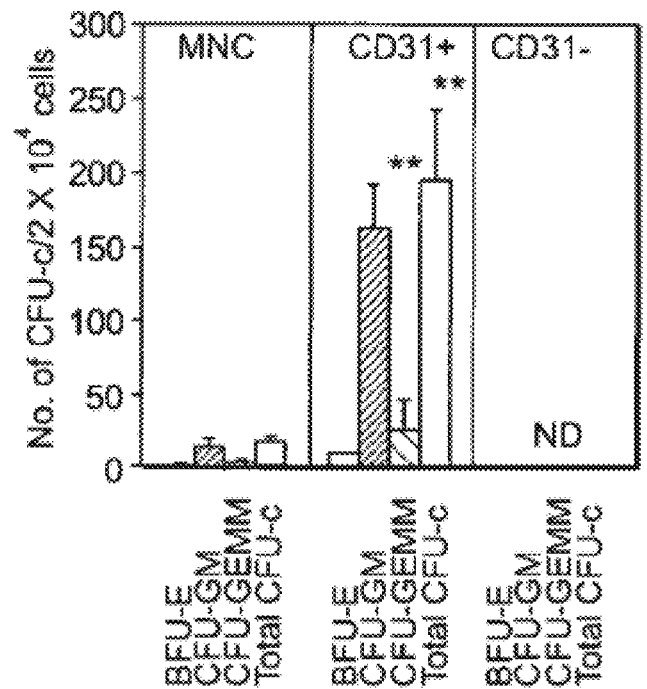
FIG. 30A shows the results of a clonogenic assay of CD31 expressing cells. A: clonogenic assay of $CD31^+$ cells. **, p<0.001, $CD31^+$ vs. BMMNCs, n=6 for each group. ND, not detectable.
Figure 30B:
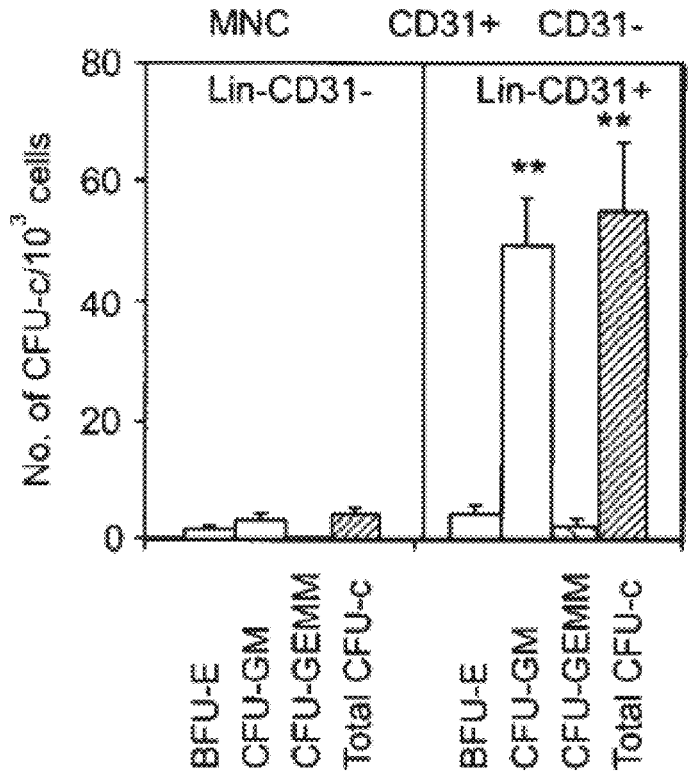
FIG. 30B shows clonogenic assay of Lin⁻$CD31^+$ cells. **, p<0.001, Lin⁻$CD31^+$ vs. Lin⁻ CD31−, n=6 for each group.

Mouse BM-derived CD31 expressing subsets are highly enriched for hematopoietic progenitor cells and possess greater hematopoietic clonogenic ability when compared with CD31$^-$ negative populations of cells. To examine the hematopoetic clonogenic potential of CD31 expressing cells, CD31$^+$ and Lin$^-$CD31$^+$ cells were isolated from MB cells of C57BL/6J mice using magnetic beads (Miltenyi Biotech). The purity of both CD31$^+$ and Lin$^-$CD31$^+$ cells is >95%. $1\times10^4$ of CD31$^+$ or $1\times10^3$ of Lin$^-$CD31$^+$ cells were plated in 35 mm Petri dishes with complete MethoCult Media (Stem Cell Technologies), containing rmCSF (50 ng/ml), rmIL-3 (10 ng/ml), rhIL-6 (10 ng/ml) and rhEPO (3U/ml), and incubated for 5 to 7 days at 37° C., 5% $CO_2$ and ≥95% humidity. Colonies were identified and counted using an inverted microscope (FIGS. 30A and 30B). These data show that CD31$^+$ and Lin$^-$CD31$^+$ cells give rise to significantly more colonies, including CFU-E, CFU-GM and CFU-GEMM, when compared to CD31 nonexpressing cells.

Example 32

Expansion of CD31$^+$ Cells

CD31 expressing cells, including CD31$^+$, Lin$^-$CD31$^+$ and Lin$^-$CD31$^+$Sca-1$^+$ cells, can be efficiently expanded when cultured with hematopoietic growth factors and have multipotent hematopoietic differentiation potential with Lin$^-$CD31$^+$ and Lin$^-$CD31$^+$Sca-1$^+$ cells.

Figure 31A:
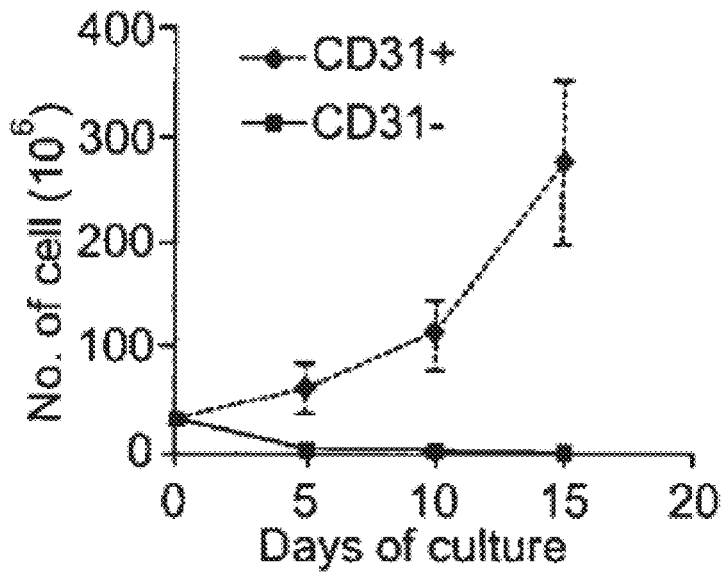
FIG. 31A shows the results of in vivo culture of CD31 expressing cellsculture of CD31+ cells with TPO, FLT3L and SCF.
Figure 31B:
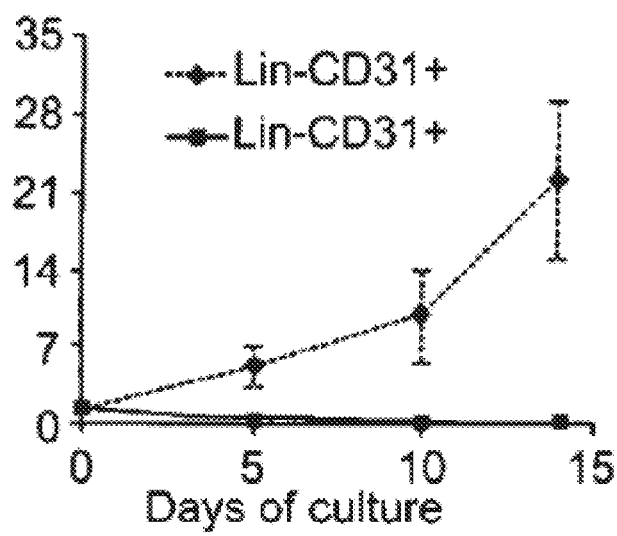
FIG. 31B shows culture of Lin-CD31+ cells with SCF, TPO, FLT3L.
Figure 31C:
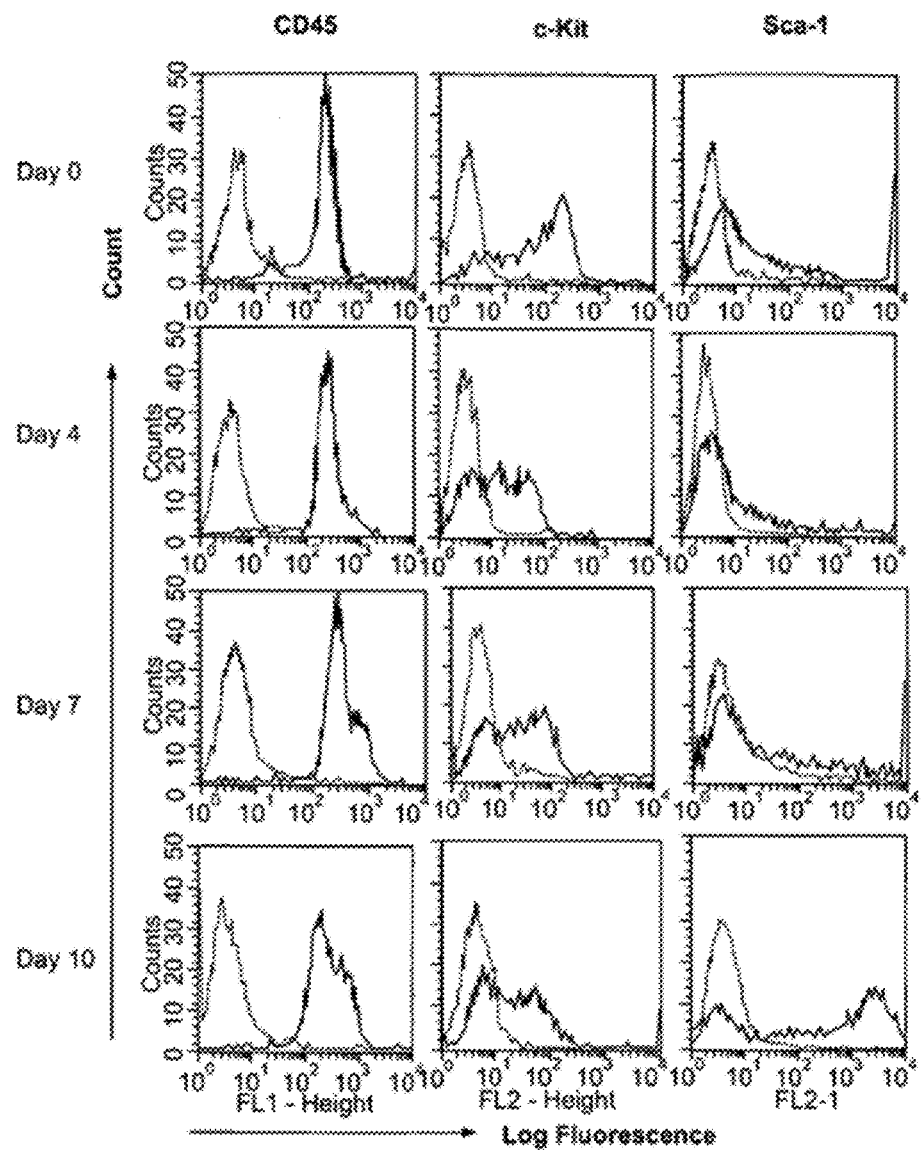
FIG. 31C shows flow cytometry analyses of cultured Lin-CD31+ cells for expression of stem cell markers, indicating that the Lin-CD31+ cells, as a hematopoietic stem and progenitor cells can be expanded efficiently in vitro.
Figure 31D:
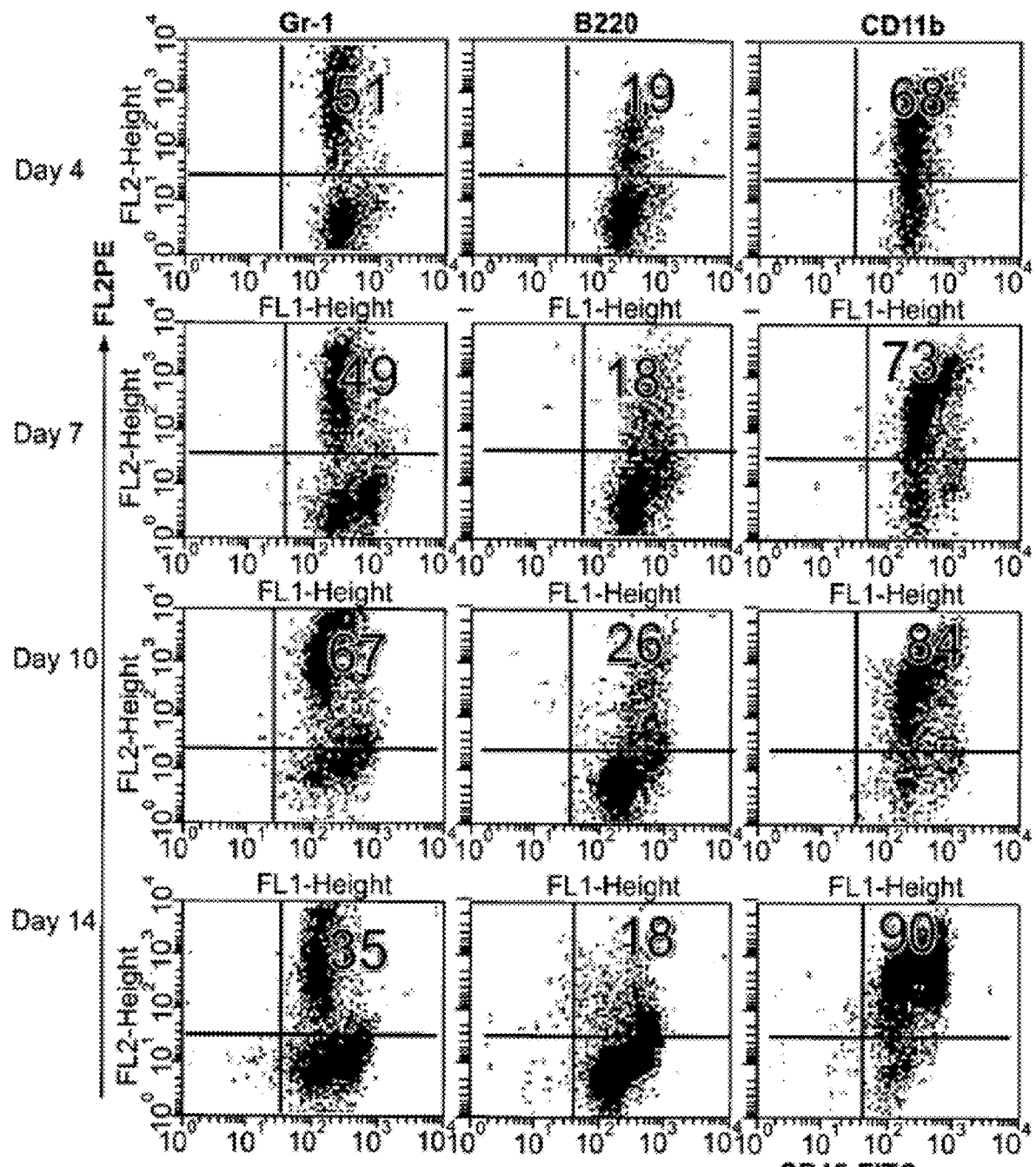
FIG. 31D shows multiple-lineage differentiation of Lin-CD31+ cells.
Figure 31E:
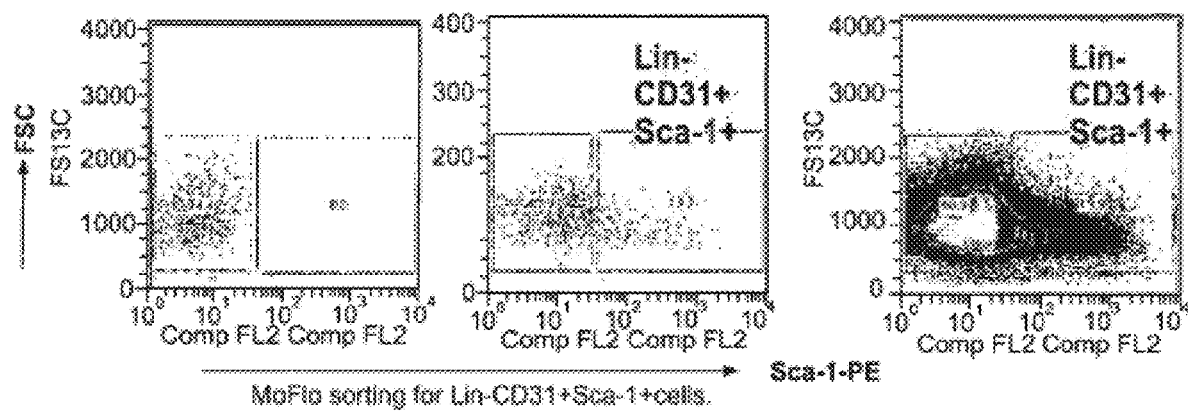
FIG. 31E shows MoFlo sorting for Lin-CD31+ Sca-1+ cells.
Figure 31F:
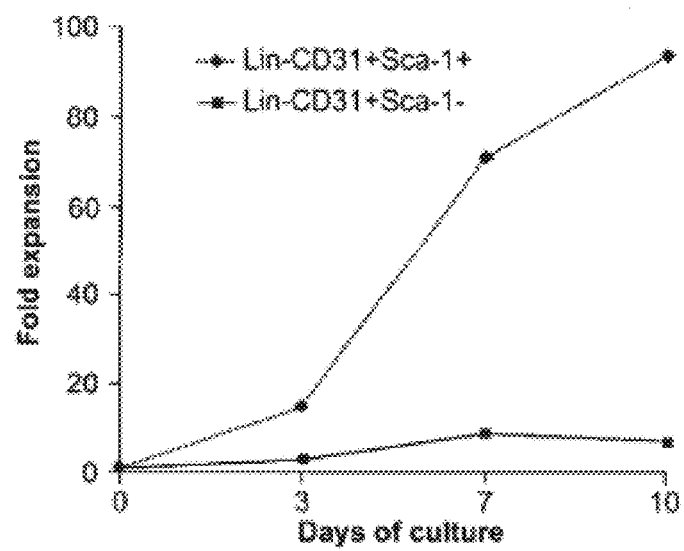
FIG. 31G shows multiple lineage differentiation of Lin-CD31-Sca-1+ cells.
Figure 31G:
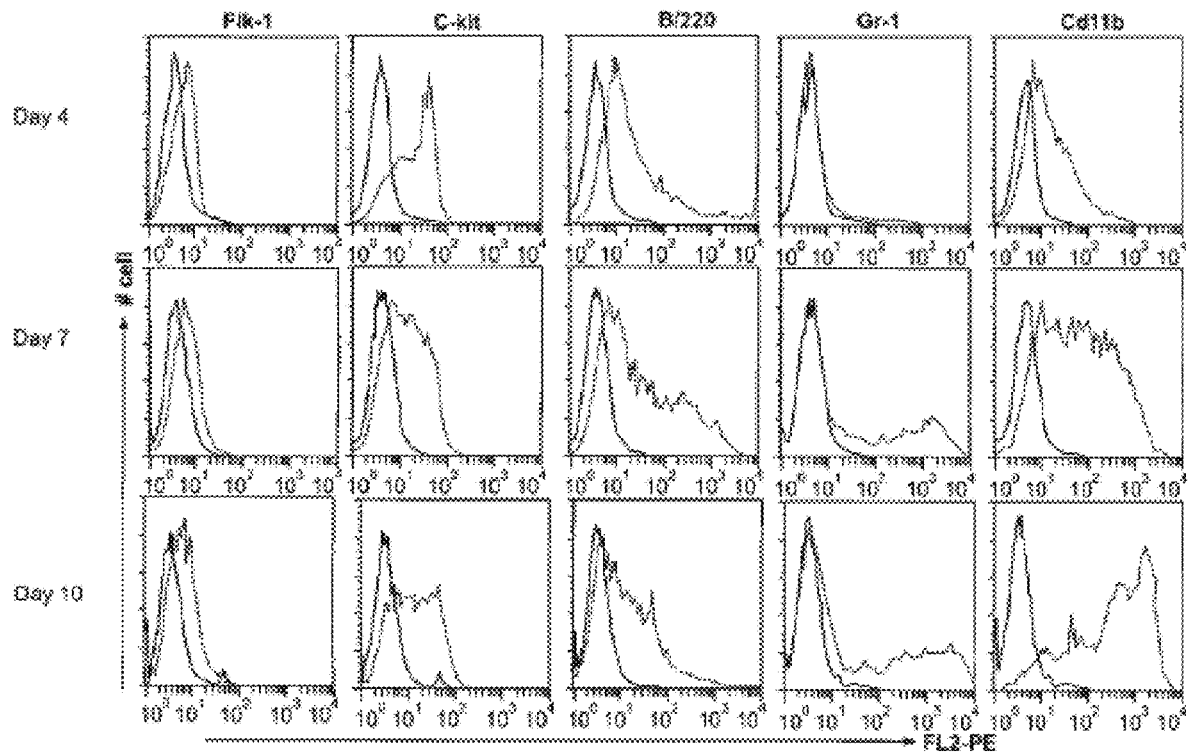

To examine the hematopoietic proliferation potential of CD31 expressing cells, CD31$^+$ and Lin$^-$CD31$^+$ were sorted by MoFlo and cultured with the IMDM medium, containing rmTPO (20 ng/ml), rmSCF (20 ng/ml) and rmFlt3-L (20 ng/ml). At different time points cells were counted and analyzed by Flow cytometry. These results showed that CD31$^+$, Lin$^-$CD31$^+$ grow rapidly under the culture condition with hematopoietic growth factors. However, CD31$^-$, Lin$^-$ CD31$^-$ cells did not proliferate and died in 3 to 5 days (FIG. 31A and 31B).

To further examine whether Lin$^-$CD31$^+$ Sca-1$^+$ cells are enriched for hematopoietic stem cells, Lin$^-$CD31$^+$Sca-1$^+$ cells were sorted by MoFlo and cultured as described above. Flow cytometry analysis showed that Lin$^-$CD31$^+$Sca-1$^+$ cells grow rapidly. However, Lin$^-$CD31$^+$Sca-1$^-$ cells did not grow. In addition, multiple lineage differentiation were also demonstrated when Lin$^-$CD31$^+$ and Lin$^-$CD31$^+$Sca-1$^+$ cells were cultured (FIG. 31C-G).

Example 33

Lin⁻CD31⁺ Cells Have Greater Potential to Repopulate BM of C57BL/6 Mice in Vivo To further text the ability of Lin⁻CD31⁺ cells to repopulate BM in vivo, Lin⁻CD31⁺ were sorted from the BM of C57BL/6J-CD45.2 mice by MoFlo. 0.5 to $5 \times 10^4$ of Lin⁻CD31⁺ cells together with $1 \times 10^5$ fresh BM cells from CD45.1 C57BL/6J mice were transplanted into lethally irradiated C57BL/6J CD45.1 mice intravenously. Mice injected with either $5 \times 10^4$ of Lin⁻ CD31⁺ cells together with $1 \times 10^5$ of fresh BM cells or $1 \times 10^5$ BM cells alone served as control groups.

Figure 32A:
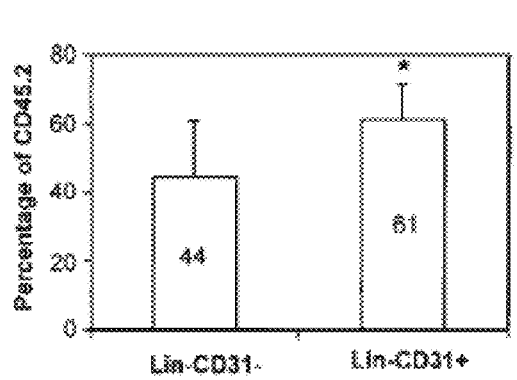
FIG. 32A shows the results of FACS analysis for in vivo BM repopulation: reconstitution of total BM transplantation chimeras 5 weeks after BM transplantation. (*, P<0.05, lin-CD31+ vs. Lin-CD31− cells, n=5 per group).
Figure 32B:
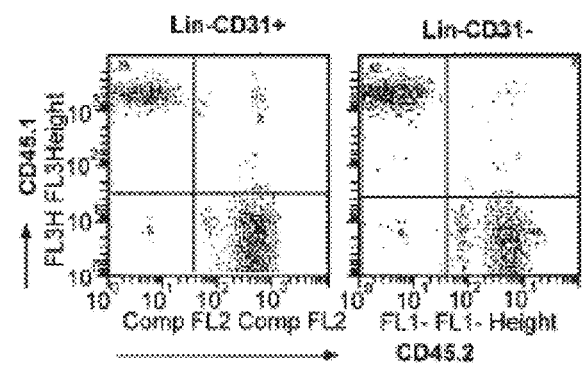
FIG. 32B shows a representative dot blot analysis of C57BL/6J mice transplanted with either Lin-CD31+ or Lin-CD31− showing reconstitutions of total BM transplantation chimeras.

To determine the contribution of the transplanted Lin⁻CD31⁺ or Lin⁻CD31⁻ cells CD45.2 BM cells, to the reconstitution of total BM chimeras, or myeloid and lymphoid compartments of transplantation chimeras, cells were obtained from peripheral blood 5 weeks after transplantation and, after red blood lysis, stained with FITC-conjugated antibody to CD45.2 and PE-conjugated antibodies to CD45.1, Mac-1, GR-1, B-220, TER-119 or CD 90.2, and then analyzed by Flow Cytometry. These data showed that mice injected with Lin⁻CD31⁺ cells obtained higher levels of reconstitution of total BM chimeras than mice injected Lin⁻CD31⁻ cells, 64% and 44% respectively ($P<0.05$) (FIG. 32A) and the reconstitutions are multiple-lineage, including myeloid and lymphoid lineages. FIG. 32B showed a representative dot blot analysis of transplanted mice for reconstitution of total BM chimeras. Our experiments indicate that Lin⁻ CD31⁺ cells have greater multipotent hematopoietic repopulating potential, as compared to Lin– CD31– cells.

Results described herein were obtained using the following methods and materials.

Methods and Materials

Mice ranging from 6-8 weeks of age were used. Bone marrow (BM) cells were isolated from male mice of either GFP-expressing C57BL/6J background or wild type. Isolated cells were used as donors in studies of transplantation or gene expression/cell culture/flow cytometric analysis. Female mice of either C57/BL6J wild type or athymic nude mice received cell transplantation after BM ablating radiation, myocardial infarction or limb ischemia.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What we claim:

1. A method of producing angiogenic progenitor cells comprising:
    sorting only CD31 positive cells from CD31 negative cells in the absence of utilizing other cell markers within bone marrow derived mononuclear cells providing a fraction of CD31 positive cells;
    and
    culturing the fraction of CD31 positive cells providing angiogenic progenitor cells.
2. The method of claim 1, further comprising the step of depleting hematopoietic linage positive cells from the fraction of CD31 positive cells prior to culturing the cells.

* * * * *